(12) United States Patent
Adami et al.

(10) Patent No.: US 9,821,067 B2
(45) Date of Patent: Nov. 21, 2017

(54) LIPOPEPTIDES FOR DELIVERY OF NUCLEIC ACIDS

(71) Applicant: Marina Biotech, Inc., Bothell, WA (US)

(72) Inventors: Roger C. Adami, Bothell, WA (US); Michael E. Houston, Jr., Sammamish, WA (US); Rachel E. Johns, Shoreline, WA (US)

(73) Assignee: Marina Biotech, Inc., City of Industry, CA (US)

( * ) Notice: Subject to any disclaimer, the term of this patent is extended or adjusted under 35 U.S.C. 154(b) by 0 days.

(21) Appl. No.: 14/941,910

(22) Filed: Nov. 16, 2015

(65) Prior Publication Data

US 2016/0058870 A1 Mar. 3, 2016

Related U.S. Application Data

(63) Continuation of application No. 13/715,768, filed on Dec. 14, 2012, now Pat. No. 9,220,785, which is a continuation of application No. 12/750,622, filed on Mar. 30, 2010, now abandoned, which is a continuation of application No. PCT/US2008/078627, filed on Oct. 2, 2008.

(60) Provisional application No. 60/976,894, filed on Oct. 2, 2007.

(51) Int. Cl.
| | | |
|---|---|---|
| A61K 47/42 | (2017.01) | |
| A61K 48/00 | (2006.01) | |
| C07K 7/08 | (2006.01) | |
| C07K 14/00 | (2006.01) | |
| A61K 47/48 | (2006.01) | |
| C12N 15/87 | (2006.01) | |
| A61K 31/713 | (2006.01) | |
| C12N 15/113 | (2010.01) | |

(52) U.S. Cl.
CPC ............ *A61K 47/42* (2013.01); *A61K 31/713* (2013.01); *A61K 47/48046* (2013.01); *A61K 47/48053* (2013.01); *A61K 47/48323* (2013.01); *A61K 48/0033* (2013.01); *A61K 48/0041* (2013.01); *C07K 7/08* (2013.01); *C07K 14/00* (2013.01); *C07K 14/001* (2013.01); *C12N 15/113* (2013.01); *C12N 15/87* (2013.01); *A61K 48/00* (2013.01); *C12N 2310/14* (2013.01)

(58) Field of Classification Search
CPC .... A61K 38/16; A61K 47/42; A61K 48/0033; A61K 48/0041; C07K 14/00; C07K 7/08
See application file for complete search history.

(56) References Cited

U.S. PATENT DOCUMENTS

| | | | | |
|---|---|---|---|---|
| 6,713,078 | B2 * | 3/2004 | Lehrer | C07K 14/4723 424/405 |
| 9,220,785 | B2 * | 12/2015 | Adami | A61K 47/48046 |
| 2006/0272049 | A1 * | 11/2006 | Waterhouse | C07K 14/43563 800/279 |
| 2007/0129305 | A1 * | 6/2007 | Divita | C07K 14/00 514/130 |

FOREIGN PATENT DOCUMENTS

| | | | |
|---|---|---|---|
| WO | WO 0198362 A2 | * | 12/2001 |
| WO | WO 2007099650 A1 | * | 9/2007 |
| WO | WO 2008049078 A1 | * | 4/2008 |

* cited by examiner

*Primary Examiner* — Jeffrey E Russel
(74) *Attorney, Agent, or Firm* — Eckman Law Group

(57) ABSTRACT

Lipopeptide compounds having a central peptide HHHHH-KHHHKKKHKHKKK (SEQ ID NO:15) and a lipophilic group attached to each terminus of the peptide, and salts thereof. The lipopeptides are useful for forming pharmaceutical compositions for delivery of nucleic acid agents, such as siRNA and mdRNA agents, as well as in methods for treating the signs and symptoms of disease.

11 Claims, No Drawings

SEQUENCE LISTING

<160> NUMBER OF SEQ ID NOS: 356

<210> SEQ ID NO 1
<211> LENGTH: 20
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"
<220> FEATURE:
<221> NAME/KEY: misc_feature
<222> LOCATION: (2)..(20)
<223> OTHER INFORMATION: /note="Residues given in the sequence have no preference with respect to those in the annotation for said positions"

<400> SEQUENCE: 1

Arg Arg Arg Arg Arg Arg Arg Arg Arg Arg Arg Arg Arg Arg Arg
1               5                   10                  15

Arg Arg Arg Arg
            20

<210> SEQ ID NO 2
<211> LENGTH: 20
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"
<220> FEATURE:

```
<221> NAME/KEY: misc_feature
<222> LOCATION: (2)..(20)
<223> OTHER INFORMATION: /note="Residues given in the sequence have no
      preference with respect to those in the annotation for said
      positions"

<400> SEQUENCE: 2

Lys Lys Lys Lys Lys Lys Lys Lys Lys Lys Lys Lys Lys Lys Lys Lys
1               5                   10                  15

Lys Lys Lys Lys
            20

<210> SEQ ID NO 3
<211> LENGTH: 40
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (2)..(20)
<223> OTHER INFORMATION: /note="Residues given in the sequence have no
      preference with respect to those in the annotation for said
      positions"
<220> FEATURE:
<221> NAME/KEY: misc_feature
<222> LOCATION: (22)..(40)
<223> OTHER INFORMATION: /note="Residues given in the sequence have no
      preference with respect to those in the annotation for said
      positions"

<400> SEQUENCE: 3

Arg Arg Arg Arg Arg Arg Arg Arg Arg Arg Arg Arg Arg Arg Arg Arg
1               5                   10                  15

Arg Arg Arg Arg Lys Lys Lys Lys Lys Lys Lys Lys Lys Lys Lys Lys
            20                  25                  30

Lys Lys Lys Lys Lys Lys Lys Lys
            35                  40

<210> SEQ ID NO 4
<211> LENGTH: 40
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(40)
<223> OTHER INFORMATION: /note="Residues given in the sequence have no
      preference with respect to those in the annotation for said
      positions"

<400> SEQUENCE: 4

Arg His Arg His Arg His Arg His Arg His Arg His Arg His Arg His
1               5                   10                  15

Arg His Arg His Arg His Arg His Arg His Arg His Arg His Arg His
            20                  25                  30

Arg His Arg His Arg His Arg His
            35                  40

<210> SEQ ID NO 5
<211> LENGTH: 80
<212> TYPE: PRT
<213> ORGANISM: Artificial sequence
```

```
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(40)
<223> OTHER INFORMATION: /note="Residues given in the sequence have no
      preference with respect to those in the annotation for said
      positions"
<220> FEATURE:
<221> NAME/KEY: misc_feature
<222> LOCATION: (43)..(80)
<223> OTHER INFORMATION: /note="Residues given in the sequence have no
      preference with respect to those in the annotation for said
      positions"

<400> SEQUENCE: 5

Arg His Arg His Arg His Arg His Arg His Arg His Arg His Arg His
1               5                   10                  15

Arg His Arg His Arg His Arg His Arg His Arg His Arg His
                20                  25                  30

Arg His Arg His Arg His Arg His His Arg His Arg His Arg
        35                  40                  45

His Arg His Arg His Arg His Arg His Arg His Arg His Arg
        50                  55                  60

His Arg His Arg His Arg His Arg His Arg His Arg His Arg
65                  70                  75                  80

<210> SEQ ID NO 6
<211> LENGTH: 40
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(40)
<223> OTHER INFORMATION: /note="Residues given in the sequence have no
      preference with respect to those in the annotation for said
      positions"

<400> SEQUENCE: 6

Lys His Lys His Lys His Lys His Lys His Lys His Lys His Lys His
1               5                   10                  15

Lys His Lys His Lys His Lys His Lys His Lys His Lys His Lys His
                20                  25                  30

Lys His Lys His Lys His Lys His
        35                  40

<210> SEQ ID NO 7
<211> LENGTH: 80
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(40)
<223> OTHER INFORMATION: /note="Residues given in the sequence have no
      preference with respect to those in the annotation for said
      positions"
<220> FEATURE:
<221> NAME/KEY: misc_feature
<222> LOCATION: (43)..(80)
```

```
<223> OTHER INFORMATION: /note="Residues given in the sequence have no
      preference with respect to those in the annotation for said
      positions"

<400> SEQUENCE: 7

Lys His Lys His Lys His Lys His Lys His Lys His Lys His Lys His
1               5                   10                  15

Lys His Lys His Lys His Lys His Lys His Lys His Lys His Lys His
            20                  25                  30

Lys His Lys His Lys His Lys His Lys His Lys His Lys His Lys
        35                  40                  45

His Lys His Lys His Lys His Lys His Lys His Lys His Lys His Lys
50                  55                  60

His Lys His Lys His Lys His Lys His Lys His Lys His Lys His Lys
65                  70                  75                  80

<210> SEQ ID NO 8
<211> LENGTH: 22
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(21)
<223> OTHER INFORMATION: /note="Residues given in the sequence have no
      preference with respect to those in the annotation for said
      positions"

<400> SEQUENCE: 8

His Lys Lys Lys Lys Lys Lys Lys Lys Lys Lys Lys Lys Lys Lys Lys
1               5                   10                  15

Lys Lys Lys Lys Lys His
            20

<210> SEQ ID NO 9
<211> LENGTH: 22
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(21)
<223> OTHER INFORMATION: /note="Residues given in the sequence have no
      preference with respect to those in the annotation for said
      positions"

<400> SEQUENCE: 9

His Arg Arg Arg Arg Arg Arg Arg Arg Arg Arg Arg Arg Arg Arg Arg
1               5                   10                  15

Arg Arg Arg Arg Arg His
            20

<210> SEQ ID NO 10
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
```

```
<400> SEQUENCE: 10

His His His His His His His His Arg Arg Arg Arg Arg Arg Arg
1               5                   10                  15

<210> SEQ ID NO 11
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 11

His His His His Arg Arg Arg Arg Arg Arg Arg Arg
1               5                   10

<210> SEQ ID NO 12
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 12

His His His His Arg Arg Arg Arg Lys Lys Lys Lys
1               5                   10

<210> SEQ ID NO 13
<211> LENGTH: 25
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 13

His His His His His His His His Arg Arg Arg Arg Arg Arg Arg
1               5                   10                  15

His His His His His His His His Lys
                20                  25

<210> SEQ ID NO 14
<211> LENGTH: 15
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 14

His His His His Arg Arg Arg Arg Arg His His His Lys Lys Lys
1               5                   10                  15

<210> SEQ ID NO 15
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 15
```

```
His His His His His Lys His His Lys Lys Lys His Lys His Lys
1               5                   10                  15

Lys Lys

<210> SEQ ID NO 16
<211> LENGTH: 36
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 16

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
                20                  25                  30

Val Leu Lys Gln
        35

<210> SEQ ID NO 17
<211> LENGTH: 36
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 17

Lys Gly Ser Lys Lys Ala Val Thr Lys Ala Gln Lys Lys Glu Gly Lys
1               5                   10                  15

Lys Arg Lys Arg Ser Arg Lys Glu Ser Tyr Ser Val Tyr Val Tyr Lys
                20                  25                  30

Val Leu Lys Gln
        35

<210> SEQ ID NO 18
<211> LENGTH: 27
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 18

Ala Gln Lys Lys Glu Gly Lys Lys Arg Lys Arg Ser Arg Lys Glu Ser
1               5                   10                  15

Tyr Ser Val Tyr Val Tyr Lys Val Leu Lys Gln
                20                  25

<210> SEQ ID NO 19
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 19

Lys Arg Ser Arg Lys Glu Ser Tyr Ser Val Tyr Val Tyr Lys Val Leu
```

```
1               5                  10                 15
```

Lys Gln

<210> SEQ ID NO 20
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 20

```
Glu Ser Tyr Ser Val Tyr Val Tyr Lys Val Leu Lys Gln
1               5                   10
```

<210> SEQ ID NO 21
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 21

```
Tyr Lys Val Leu Lys Gln
1               5
```

<210> SEQ ID NO 22
<211> LENGTH: 15
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 22

```
Arg Val Ile Arg Trp Phe Gln Asn Lys Arg Ser Lys Asp Lys Lys
1               5                   10                  15
```

<210> SEQ ID NO 23
<211> LENGTH: 27
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 23

```
Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```

<210> SEQ ID NO 24
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 24

Arg Gln Ile Lys Ile Trp Phe Gln Asn Arg Arg Met Lys Trp Lys Lys
1               5                   10                  15

<210> SEQ ID NO 25
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 25

Arg Gln Ile Lys Ile Trp Phe Gln Asn Arg Arg Met Lys Trp Lys Lys
1               5                   10                  15

<210> SEQ ID NO 26
<211> LENGTH: 26
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 26

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 27
<211> LENGTH: 21
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 27

Leu Leu Asn Gln Leu Ala Gly Arg Met Ile Pro Lys Trp Ser Gln Lys
1               5                   10                  15

Ser Lys Arg Lys Val
            20

<210> SEQ ID NO 28
<211> LENGTH: 20
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 28

Thr Leu Asp His Val Leu Asp His Val Gln Thr Trp Ser Gln Lys Ser
1               5                   10                  15

Lys Arg Lys Val
            20

<210> SEQ ID NO 29
<211> LENGTH: 23
<212> TYPE: PRT
<213> ORGANISM: Artificial sequence
<220> FEATURE:
<221> NAME/KEY: source -continued

```
<223> OTHER INFORMATION: /note="Description of artificial sequence:
      Synthetic peptide"

<400> SEQUENCE: 29

Ser Tyr Phe Ile Leu Arg Arg Arg Lys Arg Phe Pro Tyr Phe Phe
1               5                   10                  15

Thr Asp Val Arg Val Ala Ala
            20

<210> SEQ ID NO 30
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 30

Arg Arg Arg Arg Arg Arg Arg Arg Arg Arg
1               5                   10

<210> SEQ ID NO 31
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 31

Arg Arg Arg Arg Arg Arg Arg Arg
1               5

<210> SEQ ID NO 32
<211> LENGTH: 28
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 32

Lys Glu Thr Trp Trp Glu Thr Trp Trp Thr Glu Trp Ser Gln Pro Gly
1               5                   10                  15

Arg Lys Lys Arg Arg Gln Arg Arg Pro Pro Gln
            20                  25

<210> SEQ ID NO 33
<211> LENGTH: 17
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 33

Gly Arg Pro Arg Glu Ser Gly Lys Lys Arg Lys Arg Lys Arg Leu Lys
1               5                   10                  15

Pro

<210> SEQ ID NO 34
<211> LENGTH: 13
```

```
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 34

Lys Ser Tyr Ser Val Tyr Val Tyr Lys Val Leu Lys Gln
1               5                   10

<210> SEQ ID NO 35
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 35

Glu Ser Tyr Ser Val Tyr Val Tyr Arg Val Leu Arg Gln
1               5                   10

<210> SEQ ID NO 36
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 36

Arg Ser Tyr Ser Val Tyr Val Tyr Arg Val Leu Arg Gln
1               5                   10

<210> SEQ ID NO 37
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 37

Gln Lys Leu Val Lys Tyr Val Tyr Val Ser Tyr Ser Glu
1               5                   10

<210> SEQ ID NO 38
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 38

Glu Ser Tyr Ser Val Tyr Val Tyr Lys Val Leu Lys Gln
1               5                   10

<210> SEQ ID NO 39
<211> LENGTH: 13
<212> TYPE: PRT
<213> ORGANISM: Artificial sequence
<220> FEATURE:
<221> NAME/KEY: source
```

```
<223> OTHER INFORMATION: /note="Description of artificial sequence:
      Synthetic peptide"

<400> SEQUENCE: 39

Ala Ser Tyr Ser Val Tyr Val Tyr Ala Val Leu Ala Gln
1               5                   10

<210> SEQ ID NO 40
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 40

Gln Lys Leu Val Lys Tyr Val Tyr Val Ser Tyr Ser Glu
1               5                   10

<210> SEQ ID NO 41
<211> LENGTH: 19
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 41

Arg Arg Arg Arg Arg Arg Glu Ser Tyr Ser Val Tyr Val Tyr Lys Val
1               5                   10                  15

Leu Lys Gln

<210> SEQ ID NO 42
<211> LENGTH: 19
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 42

Glu Ser Tyr Ser Val Tyr Val Tyr Lys Val Leu Lys Gln Arg Arg Arg
1               5                   10                  15

Arg Arg Arg

<210> SEQ ID NO 43
<211> LENGTH: 22
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 43

Arg Arg Arg Arg Arg Arg Arg Gln Ile Lys Ile Trp Phe Gln Asn Arg
1               5                   10                  15

Arg Met Lys Trp Lys Lys
                20

<210> SEQ ID NO 44
<211> LENGTH: 22
<212> TYPE: PRT
```

```
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 44

Arg Gln Ile Lys Ile Trp Phe Gln Asn Arg Arg Met Lys Trp Lys Lys
1               5                   10                  15

Arg Arg Arg Arg Arg Arg
            20

<210> SEQ ID NO 45
<211> LENGTH: 17
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 45

Lys Thr Lys Ile Glu Ser Leu Lys Glu His Gly Arg Arg Arg Arg Arg
1               5                   10                  15

Arg

<210> SEQ ID NO 46
<211> LENGTH: 31
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 46

Met Asp Val Asn Pro Thr Leu Leu Phe Leu Lys Val Pro Ala Gln Asn
1               5                   10                  15

Ala Ile Ser Thr Thr Phe Pro Tyr Thr Arg Arg Arg Arg Arg Arg
            20                  25                  30

<210> SEQ ID NO 47
<211> LENGTH: 26
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 47

Gly Leu Phe Glu Ala Leu Leu Glu Leu Leu Glu Ser Leu Trp Glu Leu
1               5                   10                  15

Leu Leu Glu Ala Arg Arg Arg Arg Arg Arg
            20                  25

<210> SEQ ID NO 48
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 48
```

```
Leu Leu Asn Gln Leu Ala Gly Arg Met Ile Pro Lys Arg Arg Arg Arg
1               5                   10                  15

Arg Arg

<210> SEQ ID NO 49
<211> LENGTH: 17
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 49

Thr Leu Asp His Val Leu Asp His Val Gln Thr Arg Arg Arg Arg Arg
1               5                   10                  15

Arg

<210> SEQ ID NO 50
<211> LENGTH: 26
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 50

Gly Leu Phe Gly Ala Ile Ala Gly Phe Ile Glu Asn Gly Trp Glu Gly
1               5                   10                  15

Met Ile Asp Gly Arg Arg Arg Arg Arg Arg
            20                  25

<210> SEQ ID NO 51
<211> LENGTH: 17
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 51

Lys Glu Thr Trp Trp Glu Thr Trp Trp Thr Glu Arg Arg Arg Arg Arg
1               5                   10                  15

Arg

<210> SEQ ID NO 52
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 52

His His His His His His His His His Arg Arg Arg Arg Arg Arg Arg
1               5                   10                  15

<210> SEQ ID NO 53
<211> LENGTH: 22
<212> TYPE: PRT
<213> ORGANISM: Artificial sequence
<220> FEATURE:
<221> NAME/KEY: source
```

```
<223> OTHER INFORMATION: /note="Description of artificial sequence:
      Synthetic peptide"

<400> SEQUENCE: 53

Ala Ala Val Ala Leu Leu Pro Ala Val Leu Leu Ala Leu Leu Ala Pro
1               5                   10                  15

Arg Arg Arg Arg Arg Arg
            20

<210> SEQ ID NO 54
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 54

Lys Val Leu Lys Gln
1               5

<210> SEQ ID NO 55
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 55

Lys Arg Arg Gln Arg Arg Arg
1               5

<210> SEQ ID NO 56
<211> LENGTH: 34
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 56

Asp Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 57
<211> LENGTH: 15
<212> TYPE: PRT
<213> ORGANISM: Artificial sequence
<220> FEATURE:
<221> NAME/KEY: source
<223> OTHER INFORMATION: /note="Description of artificial sequence:
      Synthetic
      peptide"

<400> SEQUENCE: 57

Val Thr Val Leu Ala Leu Gly Ala Leu Ala Gly Val Gly Val Gly
1               5                   10                  15

<210> SEQ ID NO 58
```

```
<211> LENGTH: 17
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 58

Gly Ala Leu Phe Leu Gly Trp Leu Gly Ala Ala Gly Ser Thr Met Gly
1               5                   10                  15

Ala

<210> SEQ ID NO 59
<211> LENGTH: 17
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 59

Met Gly Leu Gly Leu His Leu Leu Val Leu Ala Ala Ala Leu Gln Gly
1               5                   10                  15

Ala

<210> SEQ ID NO 60
<211> LENGTH: 24
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 60

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 61
<211> LENGTH: 26
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 61

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 62
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 62
```

```
Thr Pro Pro Lys Lys Arg Lys Val Glu Asp Pro Lys Lys Lys
1               5                   10                  15
```

<210> SEQ ID NO 63
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 63

```
Lys Leu Ala Leu Lys Leu Ala Leu Lys Ala Leu Lys Ala Ala Leu Lys
1               5                   10                  15

Leu Ala
```

<210> SEQ ID NO 64
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 64

```
Gly Leu Phe Gly Ala Ile Ala Gly Phe Ile Glu Asn Gly Trp Glu Gly
1               5                   10                  15
```

<210> SEQ ID NO 65
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 65

```
Phe Phe Gly Ala Val Ile Gly Thr Ile Ala Leu Gly Val Ala Thr Ala
1               5                   10                  15
```

<210> SEQ ID NO 66
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 66

```
Phe Leu Gly Phe Leu Leu Gly Val Gly Ser Ala Ile Ala Ser Gly Val
1               5                   10                  15
```

<210> SEQ ID NO 67
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 67

```
Gly Val Phe Val Leu Gly Phe Leu Gly Phe Leu Ala Thr Ala Gly Ser
```

<210> SEQ ID NO 68
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"

<400> SEQUENCE: 68

```
Gly Ala Ala Ile Gly Leu Ala Trp Ile Pro Tyr Phe Gly Pro Ala Ala
1               5                   10                  15
```

<210> SEQ ID NO 69
<211> LENGTH: 56
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"

<400> SEQUENCE: 69

```
Ala Cys Thr Cys Pro Tyr Cys Lys Asp Ser Glu Gly Arg Gly Ser Gly
1               5                   10                  15

Asp Pro Gly Lys Lys Gln His Ile Cys His Ile Gln Gly Cys Gly
            20                  25                  30

Lys Val Tyr Gly Lys Thr Ser His Leu Arg Ala His Leu Arg Trp His
        35                  40                  45

Thr Gly Glu Arg Pro Phe Met Cys
    50                  55
```

<210> SEQ ID NO 70
<211> LENGTH: 54
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"

<400> SEQUENCE: 70

```
Ala Cys Thr Cys Pro Asn Cys Lys Asp Gly Glu Lys Arg Ser Gly Glu
1               5                   10                  15

Gln Gly Lys Lys Lys His Val Cys His Ile Pro Asp Cys Gly Lys Thr
            20                  25                  30

Phe Arg Lys Thr Ser Leu Leu Arg Ala His Val Arg Leu His Thr Gly
        35                  40                  45

Glu Arg Pro Phe Val Cys
    50
```

<210> SEQ ID NO 71
<211> LENGTH: 55
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"

<400> SEQUENCE: 71

```
Ala Cys Thr Cys Pro Asn Cys Lys Glu Gly Gly Gly Arg Gly Thr Asn
1               5                   10                  15
```

Leu Gly Lys Lys Lys Gln His Ile Cys His Ile Pro Gly Cys Gly Lys
            20                  25                  30

Val Tyr Gly Lys Thr Ser His Leu Arg Ala His Leu Arg Trp His Ser
            35                  40                  45

Gly Glu Arg Pro Phe Val Cys
        50                  55

<210> SEQ ID NO 72
<211> LENGTH: 56
<212> TYPE: PRT
<213> ORGANISM: Artificial sequence
<220> FEATURE:
<221> NAME/KEY: source
<223> OTHER INFORMATION: /note="Description of artificial sequence:
    Synthetic peptide"

<400> SEQUENCE: 72

Ala Cys Ser Cys Pro Asn Cys Arg Glu Gly Glu Gly Arg Gly Ser Asn
1               5                   10                  15

Glu Pro Gly Lys Lys Gln His Ile Cys His Ile Glu Gly Cys Gly
            20                  25                  30

Lys Val Tyr Gly Lys Thr Ser His Leu Arg Ala His Leu Arg Trp His
            35                  40                  45

Thr Gly Glu Arg Pro Phe Ile Cys
        50                  55

<210> SEQ ID NO 73
<211> LENGTH: 60
<212> TYPE: PRT
<213> ORGANISM: Artificial sequence
<220> FEATURE:
<221> NAME/KEY: source
<223> OTHER INFORMATION: /note="Description of artificial sequence:
    Synthetic peptide"

<400> SEQUENCE: 73

Arg Cys Thr Cys Pro Asn Cys Thr Asn Glu Met Ser Gly Leu Pro Pro
1               5                   10                  15

Ile Val Gly Pro Asp Glu Arg Gly Arg Lys Gln His Ile Cys His Ile
            20                  25                  30

Pro Gly Cys Glu Arg Leu Tyr Gly Lys Ala Ser His Leu Lys Thr His
            35                  40                  45

Leu Arg Trp His Thr Gly Glu Arg Pro Phe Leu Cys
        50                  55                  60

<210> SEQ ID NO 74
<211> LENGTH: 58
<212> TYPE: PRT
<213> ORGANISM: Artificial sequence
<220> FEATURE:
<221> NAME/KEY: source
<223> OTHER INFORMATION: /note="Description of artificial sequence:
    Synthetic peptide"

<400> SEQUENCE: 74

Thr Cys Asp Cys Pro Asn Cys Gln Glu Ala Glu Arg Leu Gly Pro Ala
1               5                   10                  15

Gly Val His Leu Arg Lys Lys Asn Ile His Ser Cys His Ile Pro Gly
            20                  25                  30

Cys Gly Lys Val Tyr Gly Lys Thr Ser His Leu Lys Ala His Leu Arg
            35                  40                  45

Trp His Thr Gly Glu Arg Pro Phe Val Cys
            50                  55

<210> SEQ ID NO 75
<211> LENGTH: 53
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 75

Arg Cys Thr Cys Pro Asn Cys Lys Ala Ile Lys His Gly Asp Arg Gly
1               5                   10                  15

Ser Gln His Thr His Leu Cys Ser Val Pro Gly Cys Gly Lys Thr Tyr
            20                  25                  30

Lys Lys Thr Ser His Leu Arg Ala His Leu Arg Lys His Thr Gly Asp
        35                  40                  45

Arg Pro Phe Val Cys
    50

<210> SEQ ID NO 76
<211> LENGTH: 56
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 76

Pro Gln Ile Ser Leu Lys Lys Ile Phe Phe Phe Ile Phe Ser Asn
1               5                   10                  15

Phe Arg Gly Asp Gly Lys Ser Arg Ile His Ile Cys His Leu Cys Asn
            20                  25                  30

Lys Thr Tyr Gly Lys Thr Ser His Leu Arg Ala His Leu Arg Gly His
        35                  40                  45

Ala Gly Asn Lys Pro Phe Ala Cys
    50                  55

<210> SEQ ID NO 77
<211> LENGTH: 31
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 77

Trp Trp Glu Thr Trp Lys Pro Phe Gln Cys Arg Ile Cys Met Arg Asn
1               5                   10                  15

Phe Ser Thr Arg Gln Ala Arg Arg Asn His Arg Arg His Arg
            20                  25                  30

<210> SEQ ID NO 78
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 78

Gly Lys Ile Asn Leu Lys Ala Leu Ala Ala Leu Ala Lys Lys Ile Leu
1               5                   10                  15

<210> SEQ ID NO 79
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 79

Arg Val Ile Arg Val Trp Phe Gln Asn Lys Arg Cys Lys Asp Lys Lys
1               5                   10                  15

<210> SEQ ID NO 80
<211> LENGTH: 39
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 80

Gly Arg Lys Lys Arg Arg Gln Arg Arg Pro Pro Gln Gly Arg Lys
1               5                   10                  15

Lys Arg Arg Gln Arg Arg Arg Pro Pro Gln Gly Arg Lys Lys Arg Arg
            20                  25                  30

Gln Arg Arg Arg Pro Pro Gln
        35

<210> SEQ ID NO 81
<211> LENGTH: 22
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 81

Gly Glu Gln Ile Ala Gln Leu Ile Ala Gly Tyr Ile Asp Ile Ile Leu
1               5                   10                  15

Lys Lys Lys Lys Ser Lys
            20

<210> SEQ ID NO 82
<211> LENGTH: 36
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 82

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
            20                  25                  30

Val Leu Lys Gln
        35

<210> SEQ ID NO 83
<211> LENGTH: 36
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 83

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
            20                  25                  30

Val Leu Lys Gln
        35

<210> SEQ ID NO 84
<211> LENGTH: 15
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 84

Arg Lys Glu Ser Tyr Ser Val Tyr Val Tyr Lys Val Leu Lys Gln
1               5                   10                  15

<210> SEQ ID NO 85
<211> LENGTH: 33
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 85

Lys Lys Ala Val Thr Lys Ala Gln Lys Lys Asp Gly Lys Lys Arg Lys
1               5                   10                  15

Arg Ser Arg Lys Glu Ser Tyr Ser Val Tyr Val Tyr Lys Val Leu Lys
            20                  25                  30

Gln

<210> SEQ ID NO 86
<211> LENGTH: 30
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 86

Val Thr Lys Ala Gln Lys Lys Asp Gly Lys Lys Arg Lys Arg Ser Arg
1               5                   10                  15

Lys Glu Ser Tyr Ser Val Tyr Val Tyr Lys Val Leu Lys Gln
            20                  25                  30

<210> SEQ ID NO 87
<211> LENGTH: 27
<212> TYPE: PRT

<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 87

Ala Gln Lys Lys Asp Gly Lys Lys Arg Lys Arg Ser Arg Lys Glu Ser
1               5                   10                  15
Tyr Ser Val Tyr Val Tyr Lys Val Leu Lys Gln
            20                  25

<210> SEQ ID NO 88
<211> LENGTH: 24
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 88

Lys Asp Gly Lys Lys Arg Lys Arg Ser Arg Lys Glu Ser Tyr Ser Val
1               5                   10                  15
Tyr Val Tyr Lys Val Leu Lys Gln
            20

<210> SEQ ID NO 89
<211> LENGTH: 21
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 89

Lys Lys Arg Lys Arg Ser Arg Lys Glu Ser Tyr Ser Val Tyr Val Tyr
1               5                   10                  15
Lys Val Leu Lys Gln
            20

<210> SEQ ID NO 90
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 90

Ser Tyr Ser Val Tyr Val Tyr Lys Val Leu Lys Gln
1               5                   10

<210> SEQ ID NO 91
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 91

Val Tyr Val Tyr Lys Val Leu Lys Gln
1               5

<210> SEQ ID NO 92
<211> LENGTH: 36
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 92

Lys Gly Ser Lys Lys Ala Val Thr Lys Ala Gln Lys Lys Glu Gly Lys
1               5                   10                  15

Lys Arg Lys Arg Ser Arg Lys Glu Ser Tyr Ser Val Tyr Val Tyr Lys
                20                  25                  30

Val Leu Lys Gln
        35

<210> SEQ ID NO 93
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 93

Trp Trp His His Lys Lys Arg Arg Cys
1               5

<210> SEQ ID NO 94
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 94

Trp Trp His His Lys Lys Arg Arg Cys Cys Arg Arg Lys Lys His His
1               5                   10                  15

Trp Trp

<210> SEQ ID NO 95
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 95

Gly Arg Lys Lys Arg Arg Gln Arg Arg Arg Pro Pro Gln
1               5                   10

<210> SEQ ID NO 96
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

```
<400> SEQUENCE: 96

Lys Lys Lys Arg Lys Val
1               5

<210> SEQ ID NO 97
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 97

Lys Lys Lys Arg Lys Val Lys Lys Lys Arg Lys Val
1               5                   10

<210> SEQ ID NO 98
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 98

Gly Arg Lys Lys Arg Arg Cys
1               5

<210> SEQ ID NO 99
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 99

Arg Arg Arg Pro Pro Gln Cys
1               5

<210> SEQ ID NO 100
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 100

Cys Gly Arg Lys Lys Arg Arg
1               5

<210> SEQ ID NO 101
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 101

Cys Arg Arg Arg Pro Pro Gln
1               5
```

```
<210> SEQ ID NO 102
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 102

Trp Lys Lys Lys Lys Cys
1               5

<210> SEQ ID NO 103
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 103

Cys Trp Lys Lys Lys Lys
1               5

<210> SEQ ID NO 104
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 104

Cys Arg Arg Arg Pro Pro Gln His
1               5

<210> SEQ ID NO 105
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 105

Cys Arg Arg Arg Pro Pro Gln
1               5

<210> SEQ ID NO 106
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 106

Cys Lys Lys Arg Arg Gln His
1               5

<210> SEQ ID NO 107
<211> LENGTH: 3
```

```
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 107

Cys Arg Arg
1

<210> SEQ ID NO 108
<211> LENGTH: 4
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 108

Cys Arg Arg Arg
1

<210> SEQ ID NO 109
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 109

Cys Arg Arg Arg Arg
1               5

<210> SEQ ID NO 110
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 110

Cys Arg Arg Arg Arg Arg
1               5

<210> SEQ ID NO 111
<211> LENGTH: 3
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 111

Cys Lys Lys
1

<210> SEQ ID NO 112
<211> LENGTH: 4
<212> TYPE: PRT
<213> ORGANISM: Artificial sequence
<220> FEATURE:
<221> NAME/KEY: source
```

```
<223> OTHER INFORMATION: /note="Description of artificial sequence:
      Synthetic peptide"

<400> SEQUENCE: 112

Cys Lys Lys Lys
1

<210> SEQ ID NO 113
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 113

Cys Lys Lys Lys Lys
1               5

<210> SEQ ID NO 114
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 114

Cys Lys Lys Lys Lys Lys
1               5

<210> SEQ ID NO 115
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 115

Cys Arg Arg Arg Arg Trp Trp
1               5

<210> SEQ ID NO 116
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 116

Cys Arg Arg Arg Trp Trp
1               5

<210> SEQ ID NO 117
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 117
```

```
Cys Arg Arg Trp Trp
1               5

<210> SEQ ID NO 118
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 118

Cys Lys Lys Trp Trp
1               5

<210> SEQ ID NO 119
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 119

Cys Lys Lys Lys Trp Trp
1               5

<210> SEQ ID NO 120
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 120

Cys Lys Lys Lys Lys Trp Trp
1               5

<210> SEQ ID NO 121
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 121

Cys Trp His His Arg Arg Lys Lys
1               5

<210> SEQ ID NO 122
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 122

Cys Arg Arg Lys Lys His His Trp Trp
1               5
```

```
<210> SEQ ID NO 123
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 123

Cys Lys Lys Arg Arg Trp
1               5

<210> SEQ ID NO 124
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 124

Cys Lys Lys Arg Arg His Trp
1               5

<210> SEQ ID NO 125
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 125

Cys Lys Lys Arg Arg His His Trp
1               5

<210> SEQ ID NO 126
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 126

Cys Lys Lys Arg Arg Gln
1               5

<210> SEQ ID NO 127
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 127

Lys Lys Arg Arg Gln Cys
1               5

<210> SEQ ID NO 128
<211> LENGTH: 7
<212> TYPE: PRT
```

```
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 128

Cys Gly Arg Lys Lys Arg Arg
1               5

<210> SEQ ID NO 129
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 129

Gly Arg Lys Lys Arg Arg Cys
1               5

<210> SEQ ID NO 130
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 130

Cys Gly Arg Lys Lys Arg Arg Gln
1               5

<210> SEQ ID NO 131
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 131

Gln Gly Arg Lys Lys Arg Arg Cys
1               5

<210> SEQ ID NO 132
<211> LENGTH: 4
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 132

Cys Arg Arg His
1

<210> SEQ ID NO 133
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
```

Synthetic peptide"

<400> SEQUENCE: 133

Cys Arg Arg Arg His
1               5

<210> SEQ ID NO 134
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 134

Cys Arg Arg Arg Arg His
1               5

<210> SEQ ID NO 135
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 135

Cys Arg Arg Arg Arg Arg His
1               5

<210> SEQ ID NO 136
<211> LENGTH: 4
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 136

Cys Lys Lys His
1

<210> SEQ ID NO 137
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 137

Cys Lys Lys Lys His
1               5

<210> SEQ ID NO 138
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 138

Cys Lys Lys Lys Lys His
1               5

<210> SEQ ID NO 139
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 139

Cys Lys Lys Lys Lys Lys His
1               5

<210> SEQ ID NO 140
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 140

His Trp Lys Lys Arg Arg Cys
1               5

<210> SEQ ID NO 141
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 141

Cys His Trp Lys Lys Arg Arg
1               5

<210> SEQ ID NO 142
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 142

Pro Pro His Arg Arg Arg Cys
1               5

<210> SEQ ID NO 143
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 143

Cys Pro Pro His Arg Arg Arg
1               5

```
<210> SEQ ID NO 144
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 144

Gly Arg Lys Lys Arg Arg Val Arg Arg Arg Pro Pro Gln
1               5                   10

<210> SEQ ID NO 145
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 145

Gly Arg Lys Lys Arg Arg Val Arg Arg Lys Lys Arg Gly
1               5                   10

<210> SEQ ID NO 146
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 146

Arg Arg Arg Pro Pro Gln Val Arg Pro Pro Arg Arg
1               5                   10

<210> SEQ ID NO 147
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 147

Arg Arg Lys Lys Arg Gly Val Arg Gly Arg Lys Lys Arg Arg
1               5                   10

<210> SEQ ID NO 148
<211> LENGTH: 14
<212> TYPE: PRT
```

```
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 148

Gln Pro Pro Arg Arg Val Arg Arg Arg Pro Pro Gln
1               5                   10

<210> SEQ ID NO 149
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 149

Trp Lys Lys Lys Lys Val Arg Lys Lys Lys Lys Trp
1               5                   10

<210> SEQ ID NO 150
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 150

Lys Lys Lys Lys Trp Val Arg Trp Lys Lys Lys Lys
1               5                   10

<210> SEQ ID NO 151
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (9)..(9)
<223> OTHER INFORMATION: Ornithine

<400> SEQUENCE: 151

His Gln Pro Pro Arg Arg Arg Val Arg Arg Arg Pro Pro Gln His
1               5                   10                  15

<210> SEQ ID NO 152
<211> LENGTH: 14
<212> TYPE: PRT
<213> ORGANISM: Artificial sequence
<220> FEATURE:
<221> NAME/KEY: source
```

```
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 152

Gln Pro Pro Arg Arg Val Arg Arg Arg Pro Pro Gln
1               5                   10

<210> SEQ ID NO 153
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 153

His Gln Arg Arg Lys Lys Val Arg Lys Lys Arg Arg Gln His
1               5                   10

<210> SEQ ID NO 154
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (4)..(4)
<223> OTHER INFORMATION: Ornithine

<400> SEQUENCE: 154

Arg Arg Val Arg Arg Arg
1               5

<210> SEQ ID NO 155
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (5)..(5)
<223> OTHER INFORMATION: Ornithine

<400> SEQUENCE: 155

Arg Arg Arg Val Arg Arg Arg Arg
1               5

<210> SEQ ID NO 156
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
```

```
<221> NAME/KEY: MOD_RES
<222> LOCATION: (6)..(6)
<223> OTHER INFORMATION: Ornithine

<400> SEQUENCE: 156

Arg Arg Arg Arg Val Arg Arg Arg Arg
1               5                   10

<210> SEQ ID NO 157
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 157

Arg Arg Arg Arg Arg Val Arg Arg Arg Arg Arg
1               5                   10

<210> SEQ ID NO 158
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (4)..(4)
<223> OTHER INFORMATION: Ornithine

<400> SEQUENCE: 158

Lys Lys Val Arg Lys Lys
1               5

<210> SEQ ID NO 159
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (5)..(5)
<223> OTHER INFORMATION: Ornithine

<400> SEQUENCE: 159

Lys Lys Lys Val Arg Lys Lys Lys
1               5

<210> SEQ ID NO 160
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (6)..(6)
<223> OTHER INFORMATION: Ornithine
```

<400> SEQUENCE: 160

Lys Lys Lys Lys Val Arg Lys Lys Lys
1               5

<210> SEQ ID NO 161
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 161

Lys Lys Lys Lys Lys Val Arg Lys Lys Lys Lys
1               5                   10

<210> SEQ ID NO 162
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 162

Trp Trp Arg Arg Arg Arg Val Arg Arg Arg Arg Trp Trp
1               5                   10

<210> SEQ ID NO 163
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 163

Trp Trp Arg Arg Arg Val Arg Arg Arg Trp Trp
1               5                   10

<210> SEQ ID NO 164
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (6)..(6)
<223> OTHER INFORMATION: Ornithine

<400> SEQUENCE: 164

```
Trp Trp Arg Arg Val Arg Arg Trp Trp
1               5                   10
```

<210> SEQ ID NO 165
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (6)..(6)
<223> OTHER INFORMATION: Ornithine

<400> SEQUENCE: 165

```
Trp Trp Lys Lys Val Arg Lys Lys Trp Trp
1               5                   10
```

<210> SEQ ID NO 166
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 166

```
Trp Trp Lys Lys Lys Val Arg Lys Lys Lys Trp Trp
1               5                   10
```

<210> SEQ ID NO 167
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 167

```
Trp Trp Lys Lys Lys Lys Val Arg Lys Lys Lys Lys Trp Trp
1               5                   10
```

<210> SEQ ID NO 168
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (9)..(9)
<223> OTHER INFORMATION: Ornithine

<400> SEQUENCE: 168

```
Lys Lys Arg Arg His His Trp Val Arg Trp His His Arg Arg Lys Lys
1               5                   10                  15
```

```
<210> SEQ ID NO 169
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (10)..(10)
<223> OTHER INFORMATION: Ornithine

<400> SEQUENCE: 169

Trp Trp His His Lys Lys Arg Arg Val Arg Arg Lys Lys His His
1               5                   10                  15

Trp Trp

<210> SEQ ID NO 170
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 170

Trp Arg Arg Lys Lys Val Arg Lys Lys Arg Arg Trp
1               5                   10

<210> SEQ ID NO 171
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 171

Trp His Arg Arg Lys Lys Val Arg Lys Lys Arg Arg His Trp
1               5                   10

<210> SEQ ID NO 172
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (9)..(9)
<223> OTHER INFORMATION: Ornithine

<400> SEQUENCE: 172

Trp His His Arg Arg Lys Lys Val Arg Lys Lys Arg Arg His His Trp
1               5                   10                  15
```

-continued

```
<210> SEQ ID NO 173
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 173

Gln Arg Arg Lys Lys Val Arg Lys Lys Arg Arg Gln
1               5                   10

<210> SEQ ID NO 174
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 174

Lys Lys Arg Arg Gln Val Arg Gln Arg Arg Lys Lys
1               5                   10

<210> SEQ ID NO 175
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 175

Arg Arg Lys Lys Arg Gly Val Arg Gly Arg Lys Lys Arg Arg
1               5                   10

<210> SEQ ID NO 176
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 176

Gly Arg Lys Lys Arg Arg Val Arg Arg Arg Lys Lys Arg Gly
1               5                   10

<210> SEQ ID NO 177
<211> LENGTH: 16
<212> TYPE: PRT
```

```
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (9)..(9)
<223> OTHER INFORMATION: Ornithine

<400> SEQUENCE: 177

Gln Arg Arg Lys Lys Arg Gly Val Arg Gly Arg Lys Lys Arg Arg Gln
1               5                   10                  15

<210> SEQ ID NO 178
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (9)..(9)
<223> OTHER INFORMATION: Ornithine

<400> SEQUENCE: 178

Gln Gly Arg Lys Lys Arg Arg Val Arg Arg Lys Lys Arg Gly Gln
1               5                   10                  15

<210> SEQ ID NO 179
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (5)..(5)
<223> OTHER INFORMATION: Ornithine

<400> SEQUENCE: 179

His Arg Arg Val Arg Arg Arg His
1               5

<210> SEQ ID NO 180
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (6)..(6)
<223> OTHER INFORMATION: Ornithine

<400> SEQUENCE: 180

His Arg Arg Arg Val Arg Arg Arg Arg His
1               5                   10

<210> SEQ ID NO 181
<211> LENGTH: 12
<212> TYPE: PRT
<213> ORGANISM: Artificial sequence
<220> FEATURE:
<221> NAME/KEY: source
```

```
<223> OTHER INFORMATION: /note="Description of artificial sequence:
      Synthetic peptide"
<220> FEATURE:
<221> NAME/KEY: MOD_RES
<222> LOCATION: (7)..(7)
<223> OTHER INFORMATION: Ornithine

<400> SEQUENCE: 181

His Arg Arg Arg Arg Val Arg Arg Arg Arg His
1               5                   10

<210> SEQ ID NO 182
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 182

His Arg Arg Arg Arg Val Arg Arg Arg Arg Arg His
1               5                   10

<210> SEQ ID NO 183
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (5)..(5)
<223> OTHER INFORMATION: Ornithine

<400> SEQUENCE: 183

His Lys Lys Val Arg Lys Lys His
1               5

<210> SEQ ID NO 184
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (6)..(6)
<223> OTHER INFORMATION: Ornithine

<400> SEQUENCE: 184

His Lys Lys Lys Val Arg Lys Lys Lys His
1               5                   10

<210> SEQ ID NO 185
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
```

```
<221> NAME/KEY: MOD_RES
<222> LOCATION: (7)..(7)
<223> OTHER INFORMATION: Ornithine

<400> SEQUENCE: 185

His Lys Lys Lys Lys Val Arg Lys Lys Lys Lys His
1               5                   10

<210> SEQ ID NO 186
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 186

His Lys Lys Lys Lys Lys Val Arg Lys Lys Lys Lys His
1               5                   10

<210> SEQ ID NO 187
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 187

His Trp Lys Lys Arg Arg Val Arg Arg Arg Lys Lys Trp His
1               5                   10

<210> SEQ ID NO 188
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 188

Arg Arg Lys Lys Trp His Val Arg His Trp Lys Lys Arg Arg
1               5                   10

<210> SEQ ID NO 189
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine
```

```
<400> SEQUENCE: 189

Pro Pro His Arg Arg Val Arg Arg Arg His Pro Pro
1               5                   10

<210> SEQ ID NO 190
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (8)..(8)
<223> OTHER INFORMATION: Ornithine

<400> SEQUENCE: 190

Arg Arg Arg His Pro Pro Val Arg Pro Pro His Arg Arg Arg
1               5                   10

<210> SEQ ID NO 191
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 191

Trp Trp His His Lys Lys Arg Arg Gly Gly Arg Arg Lys Lys His His
1               5                   10                  15

Trp Trp

<210> SEQ ID NO 192
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 192

Trp Trp His His Lys Lys Arg Arg
1               5

<210> SEQ ID NO 193
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 193

Tyr Tyr His His Lys Lys Arg Arg
1               5

<210> SEQ ID NO 194
<211> LENGTH: 8
<212> TYPE: PRT
<213> ORGANISM: Artificial sequence
<220> FEATURE:
<221> NAME/KEY: source
```

-continued

<223> OTHER INFORMATION: /note="Description of artificial sequence:
       Synthetic peptide"

<400> SEQUENCE: 194

Arg Arg Lys Lys His His Tyr Tyr
1               5

<210> SEQ ID NO 195
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence:
       Synthetic peptide"

<400> SEQUENCE: 195

Tyr Tyr His His Lys Lys Arg Arg Cys Cys Arg Arg Lys Lys His His
1               5                   10                  15

Tyr Tyr

<210> SEQ ID NO 196
<211> LENGTH: 17
<212> TYPE: PRT
<213> ORGANISM: Artificial sequence
<220> FEATURE:
<221> NAME/KEY: source
<223> OTHER INFORMATION: /note="Description of artificial sequence:
       Synthetic peptide"

<400> SEQUENCE: 196

Tyr Tyr His His Lys Lys Arg Arg Val Arg Arg Lys Lys His His Tyr
1               5                   10                  15

Tyr

<210> SEQ ID NO 197
<211> LENGTH: 4
<212> TYPE: PRT
<213> ORGANISM: Artificial sequence
<220> FEATURE:
<221> NAME/KEY: source
<223> OTHER INFORMATION: /note="Description of artificial sequence:
       Synthetic peptide"

<400> SEQUENCE: 197

Trp Trp Arg Arg
1

<210> SEQ ID NO 198
<211> LENGTH: 4
<212> TYPE: PRT
<213> ORGANISM: Artificial sequence
<220> FEATURE:
<221> NAME/KEY: source
<223> OTHER INFORMATION: /note="Description of artificial sequence:
       Synthetic peptide"

<400> SEQUENCE: 198

Arg Arg Trp Trp
1

<210> SEQ ID NO 199
<211> LENGTH: 7
<212> TYPE: PRT
<213> ORGANISM: Artificial sequence
<220> FEATURE:
<221> NAME/KEY: source

```
<223> OTHER INFORMATION: /note="Description of artificial sequence:
      Synthetic peptide"

<400> SEQUENCE: 199

Cys Trp Arg Arg Arg Trp Cys
1               5

<210> SEQ ID NO 200
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 200

Cys Trp Trp Arg Arg Arg Trp Trp Cys
1               5

<210> SEQ ID NO 201
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 201

Cys Trp Arg Arg Arg Arg Trp Cys
1               5

<210> SEQ ID NO 202
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 202

Cys Trp Arg Arg His His Arg Arg Trp Cys
1               5                   10

<210> SEQ ID NO 203
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 203

Cys Trp Trp Arg Arg Arg Arg Trp Trp Cys
1               5                   10

<210> SEQ ID NO 204
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 204
```

```
Cys Trp Trp Arg Arg His His Arg Arg Trp Trp Cys
1               5                   10
```

<210> SEQ ID NO 205
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 205

```
Cys Trp Arg Arg Arg Arg Arg Trp Cys
1               5
```

<210> SEQ ID NO 206
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 206

```
Val Gln Ala Ala Ile Asp Tyr Ile Asn Gly
1               5                   10
```

<210> SEQ ID NO 207
<211> LENGTH: 11
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 207

```
Cys Trp Trp Arg Arg Arg Arg Arg Trp Trp Cys
1               5                   10
```

<210> SEQ ID NO 208
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 208

```
Trp Trp Arg Arg Cys Cys Arg Arg Trp Trp
1               5                   10
```

<210> SEQ ID NO 209
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 209

```
Trp Trp Arg Arg Val Arg Arg Trp Trp
1               5
```

```
<210> SEQ ID NO 210
<211> LENGTH: 4
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 210

Tyr Tyr Arg Arg
1

<210> SEQ ID NO 211
<211> LENGTH: 4
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 211

Arg Arg Tyr Tyr
1

<210> SEQ ID NO 212
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 212

Cys Tyr Arg Arg Arg Tyr Cys
1               5

<210> SEQ ID NO 213
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 213

Cys Tyr Tyr Arg Arg Arg Tyr Tyr Cys
1               5

<210> SEQ ID NO 214
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 214

Cys Tyr Arg Arg Arg Arg Tyr Cys
1               5

<210> SEQ ID NO 215
<211> LENGTH: 10
<212> TYPE: PRT
```

```
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 215

Cys Tyr Arg Arg His His Arg Arg Tyr Cys
1               5                   10

<210> SEQ ID NO 216
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 216

Cys Tyr Tyr Arg Arg Arg Arg Tyr Tyr Cys
1               5                   10

<210> SEQ ID NO 217
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 217

Cys Tyr Tyr Arg Arg His His Arg Arg Tyr Tyr Cys
1               5                   10

<210> SEQ ID NO 218
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 218

Cys Tyr Arg Arg Arg Arg Arg Tyr Cys
1               5

<210> SEQ ID NO 219
<211> LENGTH: 11
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 219

Cys Tyr Tyr Arg Arg Arg Arg Arg Tyr Tyr Cys
1               5                   10

<210> SEQ ID NO 220
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
```

```
                        Synthetic peptide"

<400> SEQUENCE: 220

Cys Tyr Tyr Arg Arg Arg Arg Tyr Tyr Cys
1               5                   10

<210> SEQ ID NO 221
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 221

Tyr Tyr Arg Arg Cys Cys Arg Arg Tyr Tyr
1               5                   10

<210> SEQ ID NO 222
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 222

Tyr Tyr Arg Arg Val Arg Arg Tyr Tyr
1               5

<210> SEQ ID NO 223
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 223

Trp Trp Arg Arg His His
1               5

<210> SEQ ID NO 224
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 224

His His Arg Arg Trp Trp
1               5

<210> SEQ ID NO 225
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 225
```

```
Trp Trp Arg Arg His His Cys Cys His His Arg Arg Trp Trp
1               5                   10
```

<210> SEQ ID NO 226
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 226

```
Trp Trp Arg Arg His His Val His His Arg Arg Trp Trp
1               5                   10
```

<210> SEQ ID NO 227
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 227

```
Tyr Tyr Arg Arg His His
1               5
```

<210> SEQ ID NO 228
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 228

```
His His Arg Arg Tyr Tyr
1               5
```

<210> SEQ ID NO 229
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 229

```
Tyr Tyr Arg Arg His His Cys Cys Arg Arg His His Tyr Tyr
1               5                   10
```

<210> SEQ ID NO 230
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 230

```
Tyr Tyr Arg Arg His His Val Arg Arg His His Tyr Tyr
1               5                   10
```

```
<210> SEQ ID NO 231
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 231

Trp Trp Arg Arg Arg
1               5

<210> SEQ ID NO 232
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 232

Arg Arg Arg Trp Trp
1               5

<210> SEQ ID NO 233
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 233

Trp Trp Arg Arg Arg Cys Cys Arg Arg Arg Trp Trp
1               5                   10

<210> SEQ ID NO 234
<211> LENGTH: 11
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 234

Trp Trp Arg Arg Arg Val Arg Arg Arg Trp Trp
1               5                   10

<210> SEQ ID NO 235
<211> LENGTH: 5
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 235

Tyr Tyr Arg Arg Arg
1               5

<210> SEQ ID NO 236
<211> LENGTH: 5
<212> TYPE: PRT
<213> ORGANISM: Artificial sequence
```

```
<220> FEATURE:
<221> NAME/KEY: source
<223> OTHER INFORMATION: /note="Description of artificial sequence:
      Synthetic peptide"

<400> SEQUENCE: 236

Arg Arg Arg Tyr Tyr
1               5

<210> SEQ ID NO 237
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 237

Tyr Tyr Arg Arg Arg Cys Cys Arg Arg Arg Tyr Tyr
1               5                   10

<210> SEQ ID NO 238
<211> LENGTH: 11
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 238

Tyr Tyr Arg Arg Arg Val Arg Arg Arg Tyr Tyr
1               5                   10

<210> SEQ ID NO 239
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 239

Trp Trp Arg Arg Arg His His
1               5

<210> SEQ ID NO 240
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 240

His His Arg Arg Arg Trp Trp
1               5

<210> SEQ ID NO 241
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
```

```
<400> SEQUENCE: 241

Trp Trp Arg Arg Arg His His Cys Cys His His Arg Arg Arg Trp Trp
1               5                   10                  15

<210> SEQ ID NO 242
<211> LENGTH: 15
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 242

Trp Trp Arg Arg Arg His His Val His His Arg Arg Arg Trp Trp
1               5                   10                  15

<210> SEQ ID NO 243
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 243

Tyr Tyr Arg Arg Arg His His
1               5

<210> SEQ ID NO 244
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 244

His His Arg Arg Arg Tyr Tyr
1               5

<210> SEQ ID NO 245
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 245

Tyr Tyr Arg Arg Arg His His Cys Cys Arg Arg Arg His His Tyr Tyr
1               5                   10                  15

<210> SEQ ID NO 246
<211> LENGTH: 15
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 246

Tyr Tyr Arg Arg Arg His His Val Arg Arg Arg His His Tyr Tyr
```

<210> SEQ ID NO 247
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 247

Trp Trp Arg Arg Arg Arg
1               5

<210> SEQ ID NO 248
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 248

Arg Arg Arg Arg Trp Trp
1               5

<210> SEQ ID NO 249
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 249

Trp Trp Arg Arg Arg Arg Cys Cys Arg Arg Arg Arg Trp Trp
1               5                   10

<210> SEQ ID NO 250
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 250

Trp Trp Arg Arg Arg Arg Val Arg Arg Arg Arg Trp Trp
1               5                   10

<210> SEQ ID NO 251
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 251

Tyr Tyr Arg Arg Arg Arg
1               5

<210> SEQ ID NO 252

```
<211> LENGTH: 6
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 252

Arg Arg Arg Arg Tyr Tyr
1               5

<210> SEQ ID NO 253
<211> LENGTH: 14
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 253

Tyr Tyr Arg Arg Arg Arg Cys Cys Arg Arg Arg Arg Tyr Tyr
1               5                   10

<210> SEQ ID NO 254
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 254

Tyr Tyr Arg Arg Arg Arg Val Arg Arg Arg Arg Tyr Tyr
1               5                   10

<210> SEQ ID NO 255
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 255

Trp Trp Arg Arg Arg Arg His His
1               5

<210> SEQ ID NO 256
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 256

His His Arg Arg Arg Arg Trp Trp
1               5

<210> SEQ ID NO 257
<211> LENGTH: 18
<212> TYPE: PRT
<213> ORGANISM: Artificial sequence
<220> FEATURE:
```

<221> NAME/KEY: source
<223> OTHER INFORMATION: /note="Description of artificial sequence: Synthetic peptide"

<400> SEQUENCE: 257

Trp Trp Arg Arg Arg Arg His His Cys Cys His His Arg Arg Arg
1               5                   10                  15

Trp Trp

<210> SEQ ID NO 258
<211> LENGTH: 17
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"

<400> SEQUENCE: 258

Trp Trp Arg Arg Arg Arg His His Val His His Arg Arg Arg Trp
1               5                   10                  15

Trp

<210> SEQ ID NO 259
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"

<400> SEQUENCE: 259

Tyr Tyr Arg Arg Arg Arg His His
1               5

<210> SEQ ID NO 260
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"

<400> SEQUENCE: 260

His His Arg Arg Arg Arg Tyr Tyr
1               5

<210> SEQ ID NO 261
<211> LENGTH: 18
<212> TYPE: PRT
<213> ORGANISM: Artificial sequence
<220> FEATURE:
<221> NAME/KEY: source
<223> OTHER INFORMATION: /note="Description of artificial sequence: Synthetic peptide"

<400> SEQUENCE: 261

Tyr Tyr Arg Arg Arg Arg His His Cys Cys Arg Arg Arg Arg His His
1               5                   10                  15

Tyr Tyr

<210> SEQ ID NO 262
<211> LENGTH: 17
<212> TYPE: PRT

```
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 262

Tyr Tyr Arg Arg Arg Arg His His Val Arg Arg Arg Arg His His Tyr
1               5                   10                  15

Tyr

<210> SEQ ID NO 263
<211> LENGTH: 19
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 263

Trp Trp His His Lys Lys Arg Arg Trp Val Trp Arg Arg Lys Lys His
1               5                   10                  15

His Trp Trp

<210> SEQ ID NO 264
<211> LENGTH: 7
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 264

Trp Trp His His Arg Arg Cys
1               5

<210> SEQ ID NO 265
<211> LENGTH: 13
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 265

Trp Trp His His Arg Arg Val Arg Arg His His Trp Trp
1               5                   10

<210> SEQ ID NO 266
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 266

Trp Trp His His His Arg Arg Arg Cys
1               5

<210> SEQ ID NO 267
<211> LENGTH: 10
<212> TYPE: PRT
```

<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 267

Cys Trp Trp His His His Arg Arg Arg Cys
1               5                   10

<210> SEQ ID NO 268
<211> LENGTH: 11
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 268

Cys Trp Trp Trp His His His His Arg Arg Arg
1               5                   10

<210> SEQ ID NO 269
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 269

Cys Trp Trp Trp Lys Lys Arg Arg Arg
1               5

<210> SEQ ID NO 270
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 270

Cys Lys Lys Lys Trp Arg Arg Trp
1               5

<210> SEQ ID NO 271
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 271

Cys Trp Arg Arg Arg Trp Arg Arg
1               5

<210> SEQ ID NO 272
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:

Synthetic peptide"

<400> SEQUENCE: 272

Cys Trp Trp His His Lys Lys Arg Arg Cys
1               5                   10

<210> SEQ ID NO 273
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 273

Trp Trp Cys His His Lys Lys Cys Arg Arg
1               5                   10

<210> SEQ ID NO 274
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 274

Trp Trp His His Cys Lys Lys Arg Arg Cys
1               5                   10

<210> SEQ ID NO 275
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 275

Cys Trp Trp His His Lys Lys Cys Arg Arg
1               5                   10

<210> SEQ ID NO 276
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 276

Trp Trp His His Cys Cys Lys Lys Arg Arg
1               5                   10

<210> SEQ ID NO 277
<211> LENGTH: 9
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 277

```
Arg Arg Trp Trp Lys Lys His His Cys
1               5
```

<210> SEQ ID NO 278
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 278

```
Cys Trp Trp His His Lys Lys Lys Lys Cys
1               5                   10
```

<210> SEQ ID NO 279
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 279

```
Cys Trp Trp His His Arg Arg Arg Arg Cys
1               5                   10
```

<210> SEQ ID NO 280
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 280

```
Cys Arg Arg Arg Arg His His Cys
1               5
```

<210> SEQ ID NO 281
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 281

```
Cys His His Lys Lys Lys Lys Cys
1               5
```

<210> SEQ ID NO 282
<211> LENGTH: 8
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 282

```
Cys His His Arg Arg Arg Arg Cys
1               5
```

```
<210> SEQ ID NO 283
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 283

Cys Tyr Tyr Arg Arg Arg Arg His His Cys
1               5                   10

<210> SEQ ID NO 284
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 284

Cys Tyr Tyr Lys Lys Lys Lys His His Cys
1               5                   10

<210> SEQ ID NO 285
<211> LENGTH: 23
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (4)..(22)
<223> OTHER INFORMATION: /note="Residues given in the sequence have no
      preference with respect to those in the annotation for said
      positions"

<400> SEQUENCE: 285

Cys Trp Lys Lys Lys Lys Lys Lys Lys Lys Lys Lys Lys Lys Lys
1               5                   10                  15

Lys Lys Lys Lys Lys Lys Cys
                20

<210> SEQ ID NO 286
<211> LENGTH: 24
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (5)..(23)
<223> OTHER INFORMATION: /note="Residues given in the sequence have no
      preference with respect to those in the annotation for said
      positions"

<400> SEQUENCE: 286

Cys His Trp Lys Lys Lys Lys Lys Lys Lys Lys Lys Lys Lys Lys
1               5                   10                  15

Lys Lys Lys Lys Lys Lys Lys Cys
                20

<210> SEQ ID NO 287
```

```
<211> LENGTH: 16
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(13)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 287

Ala Ala Ala Asx Xaa Tyr Xaa Gln Trp Leu Xaa Xaa Xaa Gly Pro Xaa
1               5                   10                  15

<210> SEQ ID NO 288
<211> LENGTH: 22
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(21)
<223> OTHER INFORMATION: /note="Residues given in the sequence have no
      preference with respect to those in the annotation for said
      positions"

<400> SEQUENCE: 288

Cys Lys Lys Lys Lys Lys Lys Lys Lys Lys Lys Lys Lys Lys Lys Lys
1               5                   10                  15

Lys Lys Lys Lys Lys Cys
            20

<210> SEQ ID NO 289
<211> LENGTH: 24
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (4)..(22)
<223> OTHER INFORMATION: /note="Residues given in the sequence have no
      preference with respect to those in the annotation for said
      positions"

<400> SEQUENCE: 289

Cys His Lys Lys Lys Lys Lys Lys Lys Lys Lys Lys Lys Lys Lys Lys
1               5                   10                  15

Lys Lys Lys Lys Lys Lys His Cys
            20

<210> SEQ ID NO 290
```

```
<211> LENGTH: 27
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 290

Gly Ala Leu Phe Leu Ala Phe Leu Ala Ala Ala Leu Ser Leu Met Gly
1               5                   10                  15

Leu Trp Ser Gln Pro Lys Lys Lys Arg Lys Val
            20                  25

<210> SEQ ID NO 291
<211> LENGTH: 27
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: VARIANT
<222> LOCATION: (13)..(13)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (13)..(13)
<223> OTHER INFORMATION: /note="Residues given in the sequence have no
      preference with respect to those in the annotation for said
      positions"
<220> FEATURE:
<221> NAME/KEY: VARIANT
<222> LOCATION: (19)..(19)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (19)..(19)
<223> OTHER INFORMATION: /note="Residues given in the sequence have no
      preference with respect to those in the annotation for said
      positions"
<220> FEATURE:
<221> NAME/KEY: VARIANT
<222> LOCATION: (21)..(21)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (21)..(21)
<223> OTHER INFORMATION: /note="Residues given in the sequence have no
      preference with respect to those in the annotation for said
      positions"

<400> SEQUENCE: 291

Gly Ala Leu Phe Leu Ala Phe Leu Ala Ala Ala Leu Leu Leu Met Gly
1               5                   10                  15

Leu Trp Leu Gln Leu Lys Lys Lys Arg Lys Val
            20                  25

<210> SEQ ID NO 292
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 292
```

Trp Ser Gln Pro Lys Lys Lys Arg Lys Val
1               5                   10

<210> SEQ ID NO 293
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (1)..(1)
<223> OTHER INFORMATION: /note="Residues given in the sequence have no
      preference with respect to those in the annotation for said
      positions"
<220> FEATURE:
<221> NAME/KEY: VARIANT
<222> LOCATION: (12)..(12)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (12)..(12)
<223> OTHER INFORMATION: /note="Residues given in the sequence have no
      preference with respect to those in the annotation for said
      positions"

<400> SEQUENCE: 293

Leu Trp Ser Gln Pro Lys Lys Lys Arg Lys Val Leu
1               5                   10

<210> SEQ ID NO 294
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: VARIANT
<222> LOCATION: (2)..(2)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (2)..(2)
<223> OTHER INFORMATION: /note="Residues given in the sequence have no
      preference with respect to those in the annotation for said
      positions"
<220> FEATURE:
<221> NAME/KEY: VARIANT
<222> LOCATION: (10)..(10)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (10)..(10)
<223> OTHER INFORMATION: /note="Residues given in the sequence have no
      preference with respect to those in the annotation for said
      positions"

<400> SEQUENCE: 294

Trp Leu Gln Pro Lys Lys Lys Arg Lys Leu
1               5                   10

<210> SEQ ID NO 295

```
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: VARIANT
<222> LOCATION: (1)..(2)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (1)..(2)
<223> OTHER INFORMATION: /note="Residues given in the sequence have no
      preference with respect to those in the annotation for said
      positions"

<400> SEQUENCE: 295

Leu Leu Gln Pro Lys Lys Lys Arg Lys Val
1               5                   10

<210> SEQ ID NO 296
<211> LENGTH: 23
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 296

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 297
<211> LENGTH: 23
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: VARIANT
<222> LOCATION: (6)..(6)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (6)..(6)
<223> OTHER INFORMATION: /note="Residues given in the sequence have no
      preference with respect to those in the annotation for said
      positions"
<220> FEATURE:
<221> NAME/KEY: VARIANT
<222> LOCATION: (15)..(15)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (15)..(15)
<223> OTHER INFORMATION: /note="Residues given in the sequence have no
      preference with respect to those in the annotation for said
      positions"

<400> SEQUENCE: 297

Leu Ile Arg Leu Trp Leu His Leu Ile His Ile Trp Phe Gln Leu Arg
1               5                   10                  15
```

```
Arg Leu Lys Trp Lys Lys Lys
            20
```

<210> SEQ ID NO 298
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"

<400> SEQUENCE: 298

```
Gln Asn Arg Arg Leu Lys Trp Lys Lys Lys
1               5                   10
```

<210> SEQ ID NO 299
<211> LENGTH: 12
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: VARIANT
<222> LOCATION: (1)..(1)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (1)..(1)
<223> OTHER INFORMATION: /note="Residues given in the sequence have no
      preference with respect to those in the annotation for said
      positions"
<220> FEATURE:
<221> NAME/KEY: VARIANT
<222> LOCATION: (12)..(12)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (12)..(12)
<223> OTHER INFORMATION: /note="Residues given in the sequence have no
      preference with respect to those in the annotation for said
      positions"

<400> SEQUENCE: 299

```
Leu Gln Asn Arg Arg Leu Lys Trp Lys Lys Lys Leu
1               5                   10
```

<210> SEQ ID NO 300
<211> LENGTH: 10
<212> TYPE: PRT
<213> ORGANISM: Artificial sequence
<220> FEATURE:
<221> NAME/KEY: source
<223> OTHER INFORMATION: /note="Description of artificial sequence:
      Synthetic peptide"
<220> FEATURE:
<221> NAME/KEY: VARIANT
<222> LOCATION: (2)..(2)
<223> OTHER INFORMATION: /replace="Ala" or "Gln" or "His" or "Glu"
      or "Arg" or "Lys"
<220> FEATURE:
<221> NAME/KEY: misc_feature
<222> LOCATION: (2)..(2)
<223> OTHER INFORMATION: /note="Residues given in the sequence have no
      preference with respect to those in the annotation for said
      positions"

<400> SEQUENCE: 300

```
Gln Leu Arg Arg Leu Lys Trp Lys Lys Lys
```

<210> SEQ ID NO 301
<211> LENGTH: 21
<212> TYPE: DNA
<213> ORGANISM: Artificial sequence
<220> FEATURE:
<221> NAME/KEY: source
<223> OTHER INFORMATION: /note="Description of combined DNA/RNA
      molecule: Synthetic primer"
<220> FEATURE:
<221> NAME/KEY: source
<223> OTHER INFORMATION: /note="Description of artificial sequence:
      Synthetic primer"

<400> SEQUENCE: 301
ccgucagccg auuugcuaut t                                              21

<210> SEQ ID NO 302
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic primer"
<220> FEATURE:
<221> NAME/KEY: source
<223> OTHER INFORMATION: /note="Description of artificial sequence:
      Synthetic primer"

<400> SEQUENCE: 302
auagcaaauc ggcugacggt t                                              21

<210> SEQ ID NO 303
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic primer"
<220> FEATURE:
<221> NAME/KEY: source
<223> OTHER INFORMATION: /note="Description of artificial sequence:
      Synthetic primer"

<400> SEQUENCE: 303
gggucggaac ccaagcuuat t                                              21

<210> SEQ ID NO 304
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic primer"
<220> FEATURE:
<221> NAME/KEY: source
<223> OTHER INFORMATION: /note="Description of artificial sequence:
      Synthetic primer"

<400> SEQUENCE: 304
uaagcuuggg uuccgaccct a                                              21

<210> SEQ ID NO 305
<211> LENGTH: 21
<212> TYPE: DNA
<213> ORGANISM: Artificial Sequence

```
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 305
cuacacaaau cagcgauuut t                                           21

<210> SEQ ID NO 306
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 306
aaaucgcuga uuuguguagt c                                           21

<210> SEQ ID NO 307
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 307
cgggacucua gcauacuuat t                                           21

<210> SEQ ID NO 308
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 308
uaaguaugcu agagucccgt t                                           21

<210> SEQ ID NO 309
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
```

-continued

Synthetic oligonucleotide"

<400> SEQUENCE: 309
acugacagcc agacagcgat t                                        21

<210> SEQ ID NO 310
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 310
ucgcugucug gcugucagut t                                        21

<210> SEQ ID NO 311
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 311
agacagcgac caaaagaaut t                                        21

<210> SEQ ID NO 312
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 312
auucuuuugg ucgcugucut t                                        21

<210> SEQ ID NO 313
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 313
augaagaucu guuccaccat t                                        21

```
<210> SEQ ID NO 314
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 314
ugguggaaca gaucuucaut t                                              21

<210> SEQ ID NO 315
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 315
gaucuguucc accauugaat t                                              21

<210> SEQ ID NO 316
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 316
uucaauggug gaacagauct t                                              21

<210> SEQ ID NO 317
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
      molecule: Synthetic oligonucleotide"
<220> FEATURE:
<221> NAME/KEY: source
<223> OTHER INFORMATION: /note="Description of artificial sequence:
      Synthetic oligonucleotide"

<400> SEQUENCE: 317
gcaauugagg agugccugat t                                              21

<210> SEQ ID NO 318
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
```

-continued

```
       molecule: Synthetic oligonucleotide"
<220> FEATURE:
<221> NAME/KEY: source
<223> OTHER INFORMATION: /note="Description of artificial sequence:
       Synthetic oligonucleotide"

<400> SEQUENCE: 318
ucaggcacuc cucaauugct t                                              21

<210> SEQ ID NO 319
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
       molecule: Synthetic oligonucleotide"
<220> FEATURE:
<221> NAME/KEY: source
<223> OTHER INFORMATION: /note="Description of artificial sequence:
       Synthetic oligonucleotide"

<400> SEQUENCE: 319
uugaggagug ccugauuaat t                                              21

<210> SEQ ID NO 320
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
       molecule: Synthetic oligonucleotide"
<220> FEATURE:
<221> NAME/KEY: source
<223> OTHER INFORMATION: /note="Description of artificial sequence:
       Synthetic oligonucleotide"

<400> SEQUENCE: 320
uuaaucaggc acuccucaat t                                              21

<210> SEQ ID NO 321
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
       molecule: Synthetic oligonucleotide"
<220> FEATURE:
<221> NAME/KEY: source
<223> OTHER INFORMATION: /note="Description of artificial sequence:
       Synthetic oligonucleotide"

<400> SEQUENCE: 321
ggaucuuauu ucuucggagt t                                              21

<210> SEQ ID NO 322
<211> LENGTH: 21
<212> TYPE: DNA
<213> ORGANISM: Artificial Sequence
<220> FEATURE:
<221> NAME/KEY: source
<223> OTHER INFORMATION: /note="Description of combined DNA/RNA
       molecule: Synthetic oligonucleotide"
<220> FEATURE:
<221> NAME/KEY: source
<223> OTHER INFORMATION: /note="Description of artificial sequence:
       Synthetic oligonucleotide"

<400> SEQUENCE: 322
```
cuccgaagaa auaagauccu u                                        21

<210> SEQ ID NO 323
<211> LENGTH: 20
<212> TYPE: DNA
<213> ORGANISM: Artificial Sequence
<220> FEATURE:
<221> NAME/KEY: source
<223> OTHER INFORMATION: /note="Description of artificial sequence:
      Synthetic primer"

<400> SEQUENCE: 323
ggctcccagt tcttcatcac                                          20

<210> SEQ ID NO 324
<211> LENGTH: 16
<212> TYPE: DNA
<213> ORGANISM: Artificial Sequence
<220> FEATURE:
<221> NAME/KEY: source
<223> OTHER INFORMATION: /note="Description of artificial sequence:
      Synthetic primer"

<400> SEQUENCE: 324
ccttccgcac cacctc                                              16

<210> SEQ ID NO 325
<211> LENGTH: 26
<212> TYPE: DNA
<213> ORGANISM: Artificial Sequence
<220> FEATURE:
<221> NAME/KEY: source
<223> OTHER INFORMATION: /note="Description of artificial sequence:
      Synthetic probe"

<400> SEQUENCE: 325
ctagatggca agcatgtggt gtttgg                                   26

<210> SEQ ID NO 326
<211> LENGTH: 24
<212> TYPE: DNA
<213> ORGANISM: Artificial Sequence
<220> FEATURE:
<221> NAME/KEY: source
<223> OTHER INFORMATION: /note="Description of artificial sequence:
      Synthetic primer"

<400> SEQUENCE: 326
tctatcatca acgggtacaa acga                                     24

<210> SEQ ID NO 327
<211> LENGTH: 22
<212> TYPE: DNA
<213> ORGANISM: Artificial Sequence
<220> FEATURE:
<221> NAME/KEY: source
<223> OTHER INFORMATION: /note="Description of artificial sequence:
      Synthetic primer"

<400> SEQUENCE: 327
cttttcagca agtgggaagg tg                                       22

<210> SEQ ID NO 328
<211> LENGTH: 27
<212> TYPE: DNA
<213> ORGANISM: Artificial Sequence
<220> FEATURE:

<221> NAME/KEY: source
<223> OTHER INFORMATION: /note="Description of artificial sequence:
       Synthetic probe"

<400> SEQUENCE: 328
cctggccttg tctgtggaga cggatta                                           27

<210> SEQ ID NO 329
<211> LENGTH: 25
<212> TYPE: DNA
<213> ORGANISM: Artificial Sequence
<220> FEATURE:
<223> OTHER INFORMATION: Description of Combined DNA/RNA Molecule:
       Synthetic oligonucleotide
<220> FEATURE:
<221> NAME/KEY: source
<223> OTHER INFORMATION: /note="Description of artificial sequence:
       Synthetic oligonucleotide"

<400> SEQUENCE: 329
ggaucuuauu ucuucggaga caatg                                             25

<210> SEQ ID NO 330
<211> LENGTH: 27
<212> TYPE: RNA
<213> ORGANISM: Artificial Sequence
<220> FEATURE:
<221> NAME/KEY: source
<223> OTHER INFORMATION: /note="Description of artificial sequence:
       Synthetic oligonucleotide"

<400> SEQUENCE: 330
cauugucucc gaagaaauaa gauccuu                                           27

<210> SEQ ID NO 331
<211> LENGTH: 21
<212> TYPE: DNA
<213> ORGANISM: Artificial Sequence
<220> FEATURE:
<223> OTHER INFORMATION: Description of Combined DNA/RNA Molecule:
       Synthetic oligonucleotide
<220> FEATURE:
<221> NAME/KEY: source
<223> OTHER INFORMATION: /note="Description of artificial sequence:
       Synthetic oligonucleotide"

<400> SEQUENCE: 331
uucuccgaac gugucacgut t                                                 21

<210> SEQ ID NO 332
<211> LENGTH: 21
<212> TYPE: DNA
<213> ORGANISM: Artificial Sequence
<220> FEATURE:
<223> OTHER INFORMATION: Description of Combined DNA/RNA Molecule:
       Synthetic oligonucleotide
<220> FEATURE:
<221> NAME/KEY: source
<223> OTHER INFORMATION: /note="Description of artificial sequence:
       Synthetic oligonucleotide"

<400> SEQUENCE: 332
acgugacacg uucggagaat t                                                 21

<210> SEQ ID NO 333
<211> LENGTH: 21
<212> TYPE: DNA
<213> ORGANISM: Artificial Sequence
<220> FEATURE:

```
<223> OTHER INFORMATION: Description of Combined DNA/RNA Molecule:
      Synthetic oligonucleotide
<220> FEATURE:
<221> NAME/KEY: source
<223> OTHER INFORMATION: /note="Description of artificial sequence:
      Synthetic oligonucleotide"

<400> SEQUENCE: 333
cuacacaaau cagcgauuut t                                              21

<210> SEQ ID NO 334
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: source
<223> OTHER INFORMATION: /note="Description of artificial sequence:
      Synthetic oligonucleotide"

<400> SEQUENCE: 334
aaaucgcuga uuuguguagt c                                              21

<210> SEQ ID NO 335
<211> LENGTH: 21
<212> TYPE: RNA
<213> ORGANISM: Artificial Sequence
<220> FEATURE:
<221> NAME/KEY: source
<223> OTHER INFORMATION: /note="Description of artificial sequence:
      Synthetic oligonucleotide"

<400> SEQUENCE: 335
ggaaagacug uuccaaaaau u                                              21

<210> SEQ ID NO 336
<211> LENGTH: 21
<212> TYPE: RNA
<213> ORGANISM: Artificial Sequence
<220> FEATURE:
<221> NAME/KEY: source
<223> OTHER INFORMATION: /note="Description of artificial sequence:
      Synthetic oligonucleotide"

<400> SEQUENCE: 336
uuuuuggaac agucuuuccu u                                              21

<210> SEQ ID NO 337
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: source
<223> OTHER INFORMATION: /note="Description of artificial sequence:
      Synthetic oligonucleotide"

<400> SEQUENCE: 337
ggaucuuauu ucuucggagt t                                              21

<210> SEQ ID NO 338
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<221> NAME/KEY: source
<223> OTHER INFORMATION: /note="Description of artificial sequence:
      Synthetic oligonucleotide"

<400> SEQUENCE: 338
cuccgaagaa auaagaucct t                                          21

<210> SEQ ID NO 339
<211> LENGTH: 21
<212> TYPE: DNA
<213> ORGANISM: Artificial Sequence
<220> FEATURE:
<221> NAME/KEY: source
<223> OTHER INFORMATION: /note="Description of artificial sequence:
      Synthetic oligonucleotide"

<400> SEQUENCE: 339
ccgtcagccg atttgctatt t                                          21

<210> SEQ ID NO 340
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<221> NAME/KEY: source
<223> OTHER INFORMATION: /note="Description of artificial sequence:
      Synthetic oligonucleotide"

<400> SEQUENCE: 340
auagcaaauc ggctgacggt t                                          21

<210> SEQ ID NO 341
<211> LENGTH: 100
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"
<220> FEATURE:
<221> NAME/KEY: misc_feature
<222> LOCATION: (3)..(100)
<223> OTHER INFORMATION: /note="Residues given in the sequence have no
      preference with respect to those in the annotation for said
      positions"

<400> SEQUENCE: 341

Arg Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg Arg
            20                  25                  30

Arg Arg Arg Arg Arg Arg Arg Arg Arg Arg Arg Arg Arg Arg Arg Arg
        35                  40                  45

Arg Arg Arg Arg Arg Arg Arg Arg Arg Arg Arg Arg Arg Arg Arg Arg
    50                  55                  60

Arg Arg Arg Arg Arg Arg Arg Arg Arg Arg Arg Arg Arg Arg Arg Arg
65                  70                  75                  80

Arg Arg Arg Arg Arg Arg Arg Arg Arg Arg Arg Arg Arg Arg Arg Arg
                85                  90                  95

Arg Arg Arg Arg
```

100

<210> SEQ ID NO 342
<211> LENGTH: 100
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"
<220> FEATURE:
<221> NAME/KEY: misc_feature
<222> LOCATION: (3)..(100)
<223> OTHER INFORMATION: /note="Residues given in the sequence have no
      preference with respect to those in the annotation for said
      positions"

<400> SEQUENCE: 342

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys Lys
50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
                85                  90                  95

Lys Lys Lys Lys
            100

<210> SEQ ID NO 343
<211> LENGTH: 100
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"
<220> FEATURE:
<221> NAME/KEY: misc_feature
<222> LOCATION: (3)..(100)
<223> OTHER INFORMATION: /note="Residues given in the sequence have no
      preference with respect to those in the annotation for said
      positions"

<400> SEQUENCE: 343

His His His His His His His His His His His His His His His His
1               5                   10                  15

His His His His His His His His His His His His His His His His
            20                  25                  30

His His His His His His His His His His His His His His His His
        35                  40                  45

His His His His His His His His His His His His His His His His
50                  55                  60

His His His His His His His His His His His His His His His His
65                  70                  75                  80

His His His His His His His His His His His His His His His His
                85                  90                  95

His His His His
            100

```
<210> SEQ ID NO 344
<211> LENGTH: 102
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"
<220> FEATURE:
<221> NAME/KEY: misc_feature
<222> LOCATION: (4)..(101)
<223> OTHER INFORMATION: /note="Residues given in the sequence have no
      preference with respect to those in the annotation for said
      positions"

<400> SEQUENCE: 344

His Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg Arg
            20                  25                  30

Arg Arg Arg Arg Arg Arg Arg Arg Arg Arg Arg Arg Arg Arg Arg Arg
        35                  40                  45

Arg Arg Arg Arg Arg Arg Arg Arg Arg Arg Arg Arg Arg Arg Arg Arg
    50                  55                  60

Arg Arg Arg Arg Arg Arg Arg Arg Arg Arg Arg Arg Arg Arg Arg Arg
65                  70                  75                  80

Arg Arg Arg Arg Arg Arg Arg Arg Arg Arg Arg Arg Arg Arg Arg Arg
                85                  90                  95

Arg Arg Arg Arg Arg His
            100

<210> SEQ ID NO 345
<211> LENGTH: 102
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"
<220> FEATURE:
<221> NAME/KEY: misc_feature
<222> LOCATION: (4)..(101)
<223> OTHER INFORMATION: /note="Residues given in the sequence have no
      preference with respect to those in the annotation for said
      positions"

<400> SEQUENCE: 345

His Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
                85                  90                  95

Lys Lys Lys Lys Lys His
            100
```

```
<210> SEQ ID NO 346
<211> LENGTH: 300
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"
<220> FEATURE:
<221> NAME/KEY: misc_feature
<222> LOCATION: (3)..(100)
<223> OTHER INFORMATION: /note="Residues given in the sequence have no
      preference with respect to those in the annotation for said
      positions"
<220> FEATURE:
<221> NAME/KEY: misc_feature
<222> LOCATION: (103)..(200)
<223> OTHER INFORMATION: /note="Residues given in the sequence have no
      preference with respect to those in the annotation for said
      positions"
<220> FEATURE:
<221> NAME/KEY: misc_feature
<222> LOCATION: (203)..(300)
<223> OTHER INFORMATION: /note="Residues given in the sequence have no
      preference with respect to those in the annotation for said
      positions"

<400> SEQUENCE: 346

His His His His His His His His His His His His His His His His
1               5                   10                  15

His His His His His His His His His His His His His His
                20                  25                  30

His His His His His His His His His His His His His His His
                35                  40                  45

His His His His His His His His His His His His His His
50                  55                  60

His His His His His His His His His His His His His His His His
65                  70                  75                  80

His His His His His His His His His His His His His
                85                  90                  95

His His His His Arg Arg Arg Arg Arg Arg Arg Arg Arg Arg Arg
                100                 105                 110

Arg Arg Arg Arg Arg Arg Arg Arg Arg Arg Arg Arg Arg Arg
        115                 120                 125

Arg Arg Arg Arg Arg Arg Arg Arg Arg Arg Arg Arg Arg Arg
        130                 135                 140

Arg Arg Arg Arg Arg Arg Arg Arg Arg Arg Arg Arg Arg Arg Arg Arg
145                 150                 155                 160

Arg Arg Arg Arg Arg Arg Arg Arg Arg Arg Arg Arg Arg Arg Arg
                165                 170                 175

Arg Arg Arg Arg Arg Arg Arg Arg Arg Arg Arg Arg Arg Arg Arg
                180                 185                 190

Arg Arg Arg Arg Arg Arg Arg Arg His His His His His His His
            195                 200                 205

His His His His His His His His His His His His His His His
        210                 215                 220

His His His His His His His His His His His His His His His His
225                 230                 235                 240

His His His His His His His His His His His His His His His
                245                 250                 255

His His His His His His His His His His His His His His His
```

His His His His His His His His His His His His His His
              275                 280                 285

His His His His His His His His His His His
              290                 295                 300

<210> SEQ ID NO 347
<211> LENGTH: 300
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"
<220> FEATURE:
<221> NAME/KEY: misc_feature
<222> LOCATION: (3)..(100)
<223> OTHER INFORMATION: /note="Residues given in the sequence have no
      preference with respect to those in the annotation for said
      positions"
<220> FEATURE:
<221> NAME/KEY: misc_feature
<222> LOCATION: (103)..(200)
<223> OTHER INFORMATION: /note="Residues given in the sequence have no
      preference with respect to those in the annotation for said
      positions"
<220> FEATURE:
<221> NAME/KEY: misc_feature
<222> LOCATION: (203)..(300)
<223> OTHER INFORMATION: /note="Residues given in the sequence have no
      preference with respect to those in the annotation for said
      positions"

<400> SEQUENCE: 347

His His His His His His His His His His His His His His His
1               5                   10                  15

His His His His His His His His His His His His His His His
                20                  25                  30

His His His His His His His His His His His His His His His
                35                  40                  45

His His His His His His His His His His His His His His His
                50                  55                  60

His His His His His His His His His His His His His His His
65              70                  75                  80

His His His His His His His His His His His His His His His
                85                  90                  95

His His His His Lys Lys Lys Lys Lys Lys Lys Lys Lys Lys Lys
                100                 105                 110

Lys Lys Lys Lys Lys Lys Lys Lys Lys Lys Lys Lys Lys Lys Lys
              115                 120                 125

Lys Lys Lys Lys Lys Lys Lys Lys Lys Lys Lys Lys Lys Lys Lys
    130                 135                 140

Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys
              165                 170                 175

Lys Lys Lys Lys Lys Lys Lys Lys Lys Lys Lys Lys Lys Lys Lys
              180                 185                 190

Lys Lys Lys Lys Lys Lys Lys Lys His His His His His His His
              195                 200                 205

His His His His His His His His His His His His His His His
    210                 215                 220

-continued

```
His His His His His His His His His His His His His His His His
225                 230                 235                 240

His His His His His His His His His His His His His His His
                245                 250                 255

His His His His His His His His His His His His His His His
                260                 265                 270

His His His His His His His His His His His His His His His
    275                 280                 285

His His His His His His His His His His His
    290                 295                 300

<210> SEQ ID NO 348
<211> LENGTH: 40
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(40)
<223> OTHER INFORMATION: /note="Residues given in the sequence have no
      preference with respect to those in the annotation for said
      positions"

<400> SEQUENCE: 348

His Arg His Arg His Arg His Arg His Arg His Arg His Arg His Arg
1               5                   10                  15

His Arg His Arg His Arg His Arg His Arg His Arg His Arg His Arg
            20                  25                  30

His Arg His Arg His Arg His Arg
        35                  40

<210> SEQ ID NO 349
<211> LENGTH: 40
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"
<220> FEATURE:
<221> NAME/KEY: misc_feature
<222> LOCATION: (3)..(40)
<223> OTHER INFORMATION: /note="Residues given in the sequence have no
      preference with respect to those in the annotation for said
      positions"

<400> SEQUENCE: 349

His Lys His Lys His Lys His Lys His Lys His Lys His Lys His Lys
1               5                   10                  15

His Lys His Lys His Lys His Lys His Lys His Lys His Lys His Lys
            20                  25                  30

His Lys His Lys His Lys His Lys
        35                  40

<210> SEQ ID NO 350
<211> LENGTH: 13
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"
```

```
<220> FEATURE:
<221> NAME/KEY: MOD_RES
<222> LOCATION: (13)..(13)
<223> OTHER INFORMATION: Cysteamide

<400> SEQUENCE: 350

His His His His Arg Arg Arg Arg Arg Arg Arg Arg Xaa
1               5                   10

<210> SEQ ID NO 351
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

His His His His His His His His Arg Arg Arg Arg Arg Arg Arg Arg
1               5                   10                  15

<210> SEQ ID NO 352
<211> LENGTH: 28
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (28)..(28)
<223> OTHER INFORMATION: Cysteamide

<400> SEQUENCE: 352

Gly Ala Leu Phe Leu Ala Phe Leu Ala Ala Ala Leu Ser Leu Met Gly
1               5                   10                  15

Leu Trp Ser Gln Pro Lys Lys Lys Arg Lys Val Xaa
            20                  25

<210> SEQ ID NO 353
<211> LENGTH: 28
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (28)..(28)
<223> OTHER INFORMATION: Cysteamide

<400> SEQUENCE: 353

Gly Ala Leu Phe Leu Ala Phe Leu Ala Ala Ala Leu Ser Leu Met Gly
1               5                   10                  15

Leu Trp Ser Gln Pro Lys Ser Lys Arg Lys Val Xaa
            20                  25

<210> SEQ ID NO 354
<211> LENGTH: 19
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
```

```
<222> LOCATION: (19)..(19)
<223> OTHER INFORMATION: Cysteamide

<400> SEQUENCE: 354

His His His His His Lys His His Lys Lys Lys His Lys His Lys
1               5                   10                  15

Lys Lys Xaa

<210> SEQ ID NO 355
<211> LENGTH: 19
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"
<220> FEATURE:
<221> NAME/KEY: MOD_RES
<222> LOCATION: (19)..(19)
<223> OTHER INFORMATION: Cysteamide

<400> SEQUENCE: 355

His His His His His Lys His His Lys Lys Lys His Lys His Lys
1               5                   10                  15

Lys Lys Xaa

<210> SEQ ID NO 356
<211> LENGTH: 27
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 356

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
                20                  25
```

LIPOPEPTIDES FOR DELIVERY OF NUCLEIC ACIDS

SEQUENCE LISTING

This application includes a Sequence Listing submitted herewith via EFS-Web as an ASCII file created on Nov. 15, 2015, named MAR281US_SeqListcorr.txt, which is 130,076 bytes in size, and is hereby incorporated by reference in its entirety.

BACKGROUND

The delivery of a therapeutic compound to a subject can be impeded by limited ability of the compound to reach a target cell or tissue, or by restricted entry or trafficking of the compound within cells. Delivery of a therapeutic material is in general restricted by membranes of cells. These barriers and restrictions to delivery can result in the need to use much higher concentrations of a compound than is desirable to achieve a result, which brings the risk of toxic effects and side effects.

One strategy for delivery is to improve transport of a compound into cells using lipid or polymeric carrier molecules. These materials can take advantage of mechanisms that exist for selective entry into a cell, while still excluding exogenous molecules such as nucleic acids and proteins. For example, a cationic lipid may interact with a drug agent and provide contact with a cell membrane. Lipid molecules can also be organized into liposomes or particles as carriers for drug agents. Liposomal drug carriers can protect a drug molecule from degradation while improving its uptake by cells. Also, liposomal drug carriers can encapsulate or bind certain compounds by electrostatic and other interactions, and may interact with negatively charged cell membranes to initiate transport across a membrane.

The understanding of regulatory RNA and the development of RNA interference (RNAi), RNAi therapy, RNA based drugs, antisense therapy, and gene therapy, among others, has increased the need for effective means of introducing active nucleic acid agents into cells. In general, nucleic acids are stable for only limited times in cells or plasma. However, nucleic acid-based agents can be stabilized in compositions and formulations which may then be dispersed for cellular delivery.

What is needed are compositions and formulations for intracellular and in vivo delivery of a nucleic acid agent for use, ultimately, as a therapeutic, which maintain cytoprotection and relatively low toxicity. Furthermore, there is a need for compositions and methods to deliver double-stranded RNA to cells to produce the response of RNA interference. Moreover, there is a need for compositions and methods for delivery of interfering RNAs to selected cells, tissues, or compartments to modulate gene expression in a manner that will alter a phenotype or disease state.

BRIEF SUMMARY

This invention relates to novel drug delivery enhancing agents including lipids that are useful for delivering various molecules to cells. This invention provides a range of compounds, compositions, formulations, methods and uses of such agents directed ultimately toward drug delivery, therapeutics, and the diagnosis and treatment of diseases and conditions, including those that respond to modulation of gene expression or activity in a subject. More specifically, this invention relates to compounds, liposomes, lamellar vesicles, emulsions, micelles, suspensions, particles, solutions and other forms of delivery enhancing compositions and formulations, as well as therapeutic methods and uses for these delivery materials.

This invention satisfies these needs and fulfills additional objects and advantages by providing a range of novel compounds, compositions, formulations and methods that employ an interfering nucleic acid or precursor thereof in combination with various components including lipopeptides, lipids, and natural or synthetic polymers.

In some embodiments, this invention includes a peptide having 2 to 100 amino acid residues and a lipophilic group attached to at least one terminus of the peptide, or to at least one amino acid residue, and salts and uses thereof. The lipophilic group may be attached to the N-terminus, C-terminus or both termini of the peptide. The lipophilic group may be attached to at least one internal amino acid residue (i.e., an amino acid residue that is not the N-terminus or the C-terminus amino acid residue of the peptide). The lipophilic group may be attached to either termini or both and at least one internal amino acid residue.

This summary, taken along with the detailed description of the invention, as well as the appended examples and claims as a whole encompasses the disclosure.

DETAILED DESCRIPTION

This invention relates generally to the fields of RNA interference, delivery of RNA therapeutics, and to the chemistry of lipids. More particularly, this invention relates to compositions and formulations for ribonucleic acids, and their uses for medicaments and for delivery as therapeutics. This invention relates generally to methods of using ribonucleic acids in RNA interference for gene-specific inhibition of gene expression in mammals.

This invention provides a range of compositions, formulations and methods which include an interfering nucleic acid or a precursor thereof in combination with various components including lipopeptides, lipids, lipid moieties, and natural or synthetic polymers.

In some aspects, this invention provides novel compositions to facilitate the delivery of nucleic acids including RNAi-inducing agents, antisense RNA agents, or DNA to cells, tissues, organs, and in living animals, for example, mammals and humans.

Lipopeptides

This invention provides a range of lipopeptides for delivery and administration of interfering-RNA agents or antisense RNAs. The lipopeptides can be cationic, or non-cationic. As used herein, non-cationic includes neutral and anionic. Cationic lipopeptides may have one or more cationic sites.

Lipopeptides of this disclosure may be formed by substituting an nucleic acid delivery-enhancing or lipoid group at the N-terminus or the C-terminus of a peptide, or both termini of the peptide. In some aspects, the nucleic acid delivery or lipid group may be linked to the alpha-carbon of one or more an amino acid residues of the peptide or to one or more amine groups, each amine group being adjacent to the alpha-carbon of an amino acid residue of the peptide, or a combination of the N-terminus, C-terminus, alpha-carbon of one or more an amino acid residues of the peptide or to one or more amine groups, each amine group being adjacent to the alpha-carbon of an amino acid residue of the peptide. In some embodiments, the peptide core may include two or more sequential amino acids, or a peptide of 2 to 100 amino acid residues (or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues).

In some aspects, this invention provides a range of lipopeptide structures as shown in Formula I:

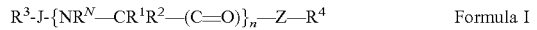   Formula I wherein
$R^1$ is independently, for each occurrence, a non-hydrogen side chain of an amino acid;
$\{NR^N-CR^1R^2-(C=O)\}_n$ is a central peptide;
$R^2$ and $R^N$ are independently of one another hydrogen, or an organic group consisting of carbon, oxygen, nitrogen, sulfur, and hydrogen atoms, and having from 1 to 20 carbon atoms, or C(1-22)alkyl, (6-12)cycloalkyl, (6-12)cycloalkylalkyl, C(3-18)alkenyl, C(3-18)alkynyl, C(1-5)alkanoyl, C(1-5)alkanoyloxy, C(1-5)alkoxy, C(1-5)alkoxy-C(1-5)alkyl, C(1-5)alkoxy-C(1-5)alkoxy, C(1-5)alkyl-amino-C(1-5)alkyl-, C(1-5)dialkyl-amino-C(1-5)alkyl-, nitro-C(1-5)alkyl, cyano-C(1-5)alkyl, aryl-C(1-5)alkyl, 4-biphenyl-C(1-5)alkyl, carboxyl, or hydroxyl;
$R^3$ and $R^4$ are independently of one another, a lipophilic tail derived from a naturally-occurring or synthetic lipid, phospholipid, glycolipid, triacylglycerol, glycerophospholipid, sphingolipid, ceramide, sphingomyelin, cerebroside, or ganglioside, wherein the tail may contain a steroid, or an organic group consisting of carbon, oxygen, nitrogen, sulfur, and hydrogen atoms, and having from 1 to 20 carbon atoms, or a substituted or unsubstituted C(1-22)alkyl, C(6-12)cycloalkyl, C(6-12)cycloalkyl-alkyl, C(3-18)alkenyl, C(3-18)alkynyl, C(1-5)alkoxy-C(1-5)alkyl, or a sphinganine, (2R,3R)-2-amino-1,3-octadecanediol, icosasphinganine, sphingosine, phytosphingosine, cis-4-sphingenine, or a ceramide;
Z is NH, O, or a linker comprising a maleimido, thioether, amide, cysteamide, cysteine, thiol, or a disulfide group, or a polyethyleneoxide or polypropyleneoxide group comprising 1-400 atoms, or a linker comprising 1-200 atoms selected from the group of C, H, F, Cl, Br, N, O, S, Si, and P;
J is (C=O), O, or a linker comprising a maleimido, thioether, amide, cysteamide, cysteine, thiol, or disulfide group, or a polyethyleneoxide or polypropyleneoxide group comprising 1-400 atoms, or a linker comprising 1-200 atoms selected from the group of C, H, F, Cl, Br, N, O, S, Si, and P; and
n is from 2 to 100.

Lipopeptides of this disclosure can be prepared where, for example, the central peptide is capable of binding nucleic acids.

Lipopeptides of this disclosure can be prepared where, for example, the central peptide may be an amphipathic amino acid sequence. For example, the peptide may have a plurality of non-polar or hydrophobic amino acid residues that form a hydrophobic sequence domain or motif which may be linked to a plurality of charged amino acid residues that form a charged sequence domain or motif, yielding an amphipathic peptide.

Lipopeptides of this disclosure can be prepared where, for example, the central peptide may be Poly-Lys-Trp, 4:1, $M_W$ 20,000-50,000; Poly-Orn-Trp, 4:1, $M_W$ 20,000-50,000; fragments or variants of mellitin protein, and fragments or variants of a histone protein, e.g., histone H1, histone H2A, histone H2B, histone H3 or histone H4.

Lipopeptides of this disclosure can be prepared where, for example, the central peptide has multiple cationic sites or multiple positively-charged residues.

The central peptides may comprise from about 2 to about 45 positively-charged residues; from about 3 to about 45 positively-charged residues; from about 4 to about 45 positively-charged residues; from about 5 to about 45 positively-charged residues; from about 10 to about 45 positively-charged residues; from about 15 to about 45 positively-charged residues; from about 20 to about 45 positively-charged residues; from about 25 to about 45 positively-charged residues; from about 30 to about 45 positively-charged residues; from about 35 to about 45 positively-charged residues; from about 40 to about 45 positively-charged residues.

The peptides may be thiolylated substantially polylysine peptides. They may comprise at least 3, 4, 5, 6, 7, 8 or so thiol groups or may have only two thiol groups.

Lipopeptides of this disclosure can be prepared where, for example, the central peptide is arginine $(Arg)_n$ (SEQ ID NO: 341), homoarginine $(homoArg)_n$ (side chain $-(CH_2)_4NH(C=NH)NH_2$), norarginine $(norArg)_n$ (side chain $-(CH_2)_2NH(C=NH)NH_2$), nor-norarginine $(nornorArg)_n$ (side chain $-(CH_2)NH(C=NH)NH_2$), ornithine $(Orn)_n$, lysine $(Lys)_n$, (SEQ ID NO: 342), histidine (His)n (SEQ ID NO: 343), where n is 2 to 100.

Lipopeptides of this disclosure can be prepared where, for example, the central peptide is $(Arg,His)_n$, $(Lys,His)_n$, $(Arg, Lys)_n$, His-$(Arg)_n$-His (SEQ ID NO: 344), His-$(Lys)_n$-His (SEQ ID NO: 345), $(His)_n$-$(Arg)_n$-$(His)_n$ (SEQ ID NO: 346), or $(His)_n$-$(Lys)_n$-$(His)_n$ (SEQ ID NO: 347), where n is 2 to 100.

A compound may have a functional group linked to a side chain of the central peptide, the functional group selected from the group consisting of 3,5-diiodo-tyrosine, 1-methylhistidine, 2-methylbutanoic acid, 2-o-anisylpropanoic acid, meso-tartaric acid, 4,6-dimethylpyrimidinamine, p-phthalic acid, creatinine, butanoic acid, N,N-dimethyl-1-naphthylamine, pentanoic acid, 4-methylpentanoic acid, N-methylaniline, 1,10-phenanthroline, 3-pyridinecarboxylic acid, hexanoic acid, propanoic acid, 4-animobenzoic acid, 2-methylpropanoic acid, heptanoic acid, octanoic acid, cyclohexanecarboxylic acid, quinoline, 3-quinolinamine, 2-aminobenzoic acid, 4-pyridinecarboxylic acid, nonanoic acid, melamine, 8-quinolinol, trimethylacetic acid, 6-methoxyquinoline, 4-(methylamino)benzoic acid, p-methylaniline, 3-(methylamino)benzoic acid, malic acid, N-ethylaniline, 2-benzylpyridine, 3,6-dinitrophenol, N,N-dimethylaniline, 2,5-dimethylpiperazine, p-phenetidine, 5-methylquinoline, 2-phenylbenzimidazole, pyridine, picolinic acid, p-anisidine, 2-(methylamino)benzoic acid, 2-thiazolamine, glutaric acid, adipic acid, isoquinoline, itaconic acid, o-phthalic acid, benzimidazole, piperazine, heptanedioic acid, acridine, phenanthridine, succinic acid, methyl succinic acid, 4-methylquinoline, 3-methylpyridine, 7-isoquinolinol, malonic acid, methylmalonic acid, 2-methylquinoline, 2-ethylpyridine, 2-methylpyridine, 4-methylpyridine, histamine, histidine, maleic acid, cis-1,2-cyclohexanediamine, 3,5-dimethylpyridine, 2-ethylbenzimidazole, 2-methylbenzimidazole, cacodylic acid, perimidine, citric acid, isocitric acid, 2,5-dimethylpyridine, papaverine, 6-hydroxy-4-methylpteridine, L-thyroxine, 3,4-dimethylpyridine, methoxypyridine, trans-1,2-cyclohexanediamine, 2,5-pyridinediamine, 1-1-methylhistidine, 1-3-methylhistidine, 2,3-dimethylpyridine, xanthopterin, 1,2-propanediamine, N,N-diethylaniline, alloxanic acid, 2,6-dimethylpyridine, L-carnosine, 2-pyridinamine, N-b-alanylhistidine, pilocarpine, 1-methylimidazol, 1H-imidazole, 2,4-dimethylpyridine, 4-nitrophenol, 2-nitrophenol, tyrosineamide, 5-hydoxyquinazoline, 1,1-cyclopropanedicarboxylic acid, 2,4,6-trimethylpyridine, 2,3-dichlorophenol, 1,2-ethanediamine, 1-isoquinolinamine, and combinations thereof.

Examples of the central peptide of lipopeptides of this disclosure include those shown in Table 1.

TABLE 1

Peptide Structures for Lipopeptides

| AMINO ACID SEQUENCE | SEQ ID NO: |
|---|---|
| $(R)_n$ where n = 1-20 | 1 |
| $(K)_n$ where n = 1-20 | 2 |
| $(R)_n(K)_n$ where n and m are independently for each occurrence 1-20 | 3 |
| $(RH)_n$ or $(HR)_n$ where n = 1-20 | 4 & 348 |
| $[(RH)_n(HR)_m]$ where n and m are independently for each occurrence 1-20 | 5 |
| $(KH)_n$ or $(HK)_n$ where n = 1-20 | 6 & 349 |
| $[(KH)_n(HK)_m]$ where n and m are independently for each occurrence 1-20 | 7 |
| $H(K)_nH$ where n = 1-20 | 8 |
| $H(R)_nH$ where n = 1-20 | 9 |
| $(H)_8(R)_8$ | 10 |
| $(H)_4(R)_8$ | 11 |
| $(H)_4(R)_4(K)_4$ | 12 |
| $(H)_8(R)_8(H)_8(K)$ | 13 |
| $(H)_4(R)_5(H)_3(K)_3$ | 14 |
| HHHHHKHHHKKKHKHKKK | 15 |
| KGSKKAVTKAQKKDGKKRKRSRKESYSVYVYKVLKQ | 16 |
| KGSKKAVTKAQKKEGKKRKRSRKESYSVYVYKVLKQ | 17 |
| AQKKEGKKRKRSRKESYSVYVYKVLKQ | 18 |
| KRSRKESYSVYVYKVLKQ | 19 |
| ESYSVYVYKVLKQ | 20 |
| YKVLKQ | 21 |
| RVIRWFQNKRSKDKK | 22 |
| GALFLGFLGAAGSTMGAWSQPKSKRKV | 23 |
| RQIKIWFQNRRMKWKK | 24 |
| RQIKIWFQNRRMKWKK (ALL D-AMINO ACIDS) | 25 |
| GWTLNSAGYLLKINLKALAALAKKIL | 26 |
| LLNQLAGRMIPKWSQKSKRKV | 27 |
| TLDHVLDHVQTWSQKSKRKV | 28 |

TABLE 1-continued

Peptide Structures for Lipopeptides

| AMINO ACID SEQUENCE | SEQ ID NO: |
|---|---|
| SYFILRRRRKRFPYFFTDVRVAA | 29 |
| RRRRRRRRR | 30 |
| RRRRRRRR (all D-amino acids) | 31 |
| KETWWETWWTEWSQPGRKKRRQRRRPPQ | 32 |
| GRPRESGKKRKRKRLKP | 33 |
| KSYSVYVYKVLKQ | 34 |
| ESYSVYVYRVLRQ | 35 |
| RSYSVYVYRVLRQ | 36 |
| QKLVKYVYVSYSE | 37 |
| ESYSVYVYKVLKQ (all D-amino acids) | 38 |
| ASYSVYVYAVLAQ | 39 |
| QKLVKYVYVSYSE (all D-amino acids) | 40 |
| RRRRRRESYSVYVYKVLKQ | 41 |
| ESYSVYVYKVLKQRRRRRR | 42 |
| RRRRRRRQIKIWFQNRRMKWKK | 43 |
| RQIKIWFQNRRMKWKKRRRRRR | 44 |
| KTKIESLKEHGRRRRRR | 45 |
| MDVNPTLLFLKVPAQNAISTTFPYTRRRRRR | 46 |
| GLFEALLELLESLWELLLEARRRRRR | 47 |
| LLNQLAGRMIPKRRRRRR | 48 |
| TLDHVLDHVQTRRRRRR | 49 |
| GLFGAIAGFIENGWEGMIDGRRRRRR | 50 |
| KETWWETWWTERRRRRR | 51 |
| HHHHHHHHHHRRRRRR | 52 |
| AAVALLPAVLLALLAPRRRRRR | 53 |
| KVLKQ | 54 |
| KRRQRRR | 55 |
| DAATATRGRSAASRPTERPRAPARSASRPRRPVD | 56 |
| VTVLALGALAGVGVG | 57 |
| GALFLGWLGAAGSTMGA | 58 |
| MGLGLHLLVLAAALQGA | 59 |
| LGTYTQDFNKFHTFPQTAIGVGAP | 60 |
| GWTLNSAGYLLKINLKALAALAKKIL | 61 |
| TPPKKKRKVEDPKKKK | 62 |
| KLALKLALKALKAALKLA | 63 |
| GLFGAIAGFIENGWEG | 64 |
| FFGAVIGTIALGVATA | 65 |

TABLE 1-continued

Peptide Structures for Lipopeptides

| AMINO ACID SEQUENCE | SEQ ID NO: |
|---|---|
| FLGFLLGVGSAIASGV | 66 |
| GVFVLGFLGFLATAGS | 67 |
| GAAIGLAWIPYFGPAA | 68 |
| ACTCPYCKDSEGRGSGDPGKKKQHICHIQGCGKVYGKTSHLRAHLRWHTGERPFMC | 69 |
| ACTCPNCKDGEKRSGEQGKKKHVCHIPDCGKTFRKTSLLRAHVRLHTGERPFVC | 70 |
| ACTCPNCKEGGGRGTNLGKKKQHICHIPGCGKVYGKTSHLRAHLRWHSGERPFVC | 71 |
| ACSCPNCREGEGRGSNEPGKKKQHICHIEGCGKVYGKTSHLRAHLRWHTGERPFIC | 72 |
| RCTCPNCTNEMSGLPPIVGPDERGRKQHICHIPGCERLYGKASHLKTHLRWHTGERPFLC | 73 |
| TCDCPNCQEAERLGPAGVHLRKKNIHSCHIPGCGKVYGKTSHLKAHLRWHTGERPFVC | 74 |
| RCTCPNCKAIKHGDRGSQHTHLCSVPGCGKTYKKTSHLRAHLRKHTGDRPFVC | 75 |
| PQISLKKKIFFFIFSNFRGDGKSRIHICHLCNKTYGKTSHLRAHLRGHAGNKPFAC | 76 |
| WWETWKPFQCRICMRNFSTRQARRNHRRRHR | 77 |
| GKINLKALAALAKKIL | 78 |
| RVIRVWFQNKRCKDKK | 79 |
| GRKKRRQRRRPPQGRKKRRQRRRPPQGRKKRRQRRRPPQ | 80 |
| GEQIAQLIAGYIDIILKKKKSK | 81 |
| KGSKKAVTKAQKKDGKKRKRSRKESYSVYVYKVLKQ | 82 |
| KGSKKAVTKAQKKDGKKRKRSRKESYSVYVYKVLKQ | 83 |
| RKESYSVYVYKVLKQ | 84 |
| KKAVTKAQKKDGKKRKRSRKESYSVYVYKVLKQ | 85 |
| VTKAQKKDGKKRKRSRKESYSVYVYKVLKQ | 86 |
| AQKKDGKKRKRSRKESYSVYVYKVLKQ | 87 |
| KDGKKRKRSRKESYSVYVYKVLKQ | 88 |
| KKRKRSRKESYSVYVYKVLKQ | 89 |
| SYSVYVYKVLKQ | 90 |
| VYVYKVLKQ | 91 |
| KGSKKAVTKAQKKEGKKRKRSRKESYSVYVYKVLKQ | 92 |
| WWHHKKRRC | 93 |
| WWHHKKRRCCRRKKHHWW | 94 |
| GRKKRRQRRRPPQ | 95 |
| KKKRKV | 96 |
| KKKRKVKKKRKV | 97 |
| GRKKRRC | 98 |
| RRRPPQC | 99 |
| CGRKKRR | 100 |
| CRRRPPQ | 101 |
| WKKKKC | 102 |
| CWKKKK | 103 |
| CRRRPPQH | 104 |
| CRRRPPQ | 105 |
| CKKRRQH | 106 |
| CRR | 107 |
| CRRR | 108 |
| CRRRR | 109 |
| CRRRRR | 110 |
| CKK | 111 |
| CKKK | 112 |
| CKKKK | 113 |
| CKKKKK | 114 |
| CRRRRWW | 115 |
| CRRRWW | 116 |
| CRRWW | 117 |
| CKKWW | 118 |
| CKKKWW | 119 |
| CKKKKWW | 120 |
| CWHHRRKK | 121 |
| CRRKKHHWW | 122 |
| CKKRRW | 123 |
| CKKRRHW | 124 |
| CKKRRHHW | 125 |
| CKKRRQ | 126 |
| KKRRQC | 127 |
| CGRKKRR | 128 |
| GRKKRRC | 129 |
| CGRKKRRQ | 130 |
| QGRKKRRC | 131 |
| CRRH | 132 |
| CRRRH | 133 |
| CRRRRH | 134 |
| CRRRRRH | 135 |

TABLE 1-continued

Peptide Structures for Lipopeptides

| AMINO ACID SEQUENCE | SEQ ID NO: |
|---|---|
| CKKH | 136 |
| CKKKH | 137 |
| CKKKKH | 138 |
| CKKKKKH | 139 |
| HWKKRRC | 140 |
| CHWKKRR | 141 |
| PPHRRRC | 142 |
| CPPHRRR | 143 |
| GRKKRRVURRRPPQ | 144 |
| GRKKRRVURRKKRG | 145 |
| RRRPPQVUPPRRR | 146 |
| RRKKRGVUGRKKRR | 147 |
| QPPRRRVURRRPPQ | 148 |
| WKKKKVUKKKKW | 149 |
| KKKKWVUWKKKK | 150 |
| HQPPRRRVURRRPPQH | 151 |
| QPPRRRVURRRPPQ | 152 |
| HQRRKKVUKKRRQH | 153 |
| RRVURR | 154 |
| RRRVURRR | 155 |
| RRRRVURRRR | 156 |
| RRRRRVURRRRR | 157 |
| KKVUKK | 158 |
| KKKVUKKK | 159 |
| KKKKVUKKKK | 160 |
| KKKKKVUKKKKK | 161 |
| WWRRRRVURRRRWW | 162 |
| WWRRRVURRRWW | 163 |
| WWRRVURRWW | 164 |
| WWKKVUKKWW | 165 |
| WWKKKVUKKKWW | 166 |
| WWKKKKVUKKKKWW | 167 |
| KKRRHHWVUWHHRRKK | 168 |
| WWHHKKRRVURRKKHHWW | 169 |
| WRKKKVUKKRRW | 170 |
| WHRRKKVUKKRRHW | 171 |
| WHHRRKKVUKKRRHHW | 172 |
| QRRKKVUKKRRQ | 173 |
| KKRRQVUQRRKK | 174 |
| RRKKRGVUGRKKRR | 175 |
| GRKKRRVURRKKRG | 176 |
| QRRKKRGVUGRKKRRQ | 177 |
| QGRKKRRVURRKKRGQ | 178 |
| HRRVURRH | 179 |
| HRRRVURRRH | 180 |
| HRRRRVURRRRH | 181 |
| HRRRRRVURRRRRH | 182 |
| HKKVUKKH | 183 |
| HKKKVUKKKH | 184 |
| HKKKKVUKKKKH | 185 |
| HKKKKKVUKKKKKH | 186 |
| HWKKRRVURRKKWH | 187 |
| RRKKWHVUHWKKRR | 188 |
| PPHRRRVURRRHPP | 189 |
| RRRHPPVUPPHRRR | 190 |
| WWHHKKRRGGRRKKHHWW | 191 |
| WWHHKKRR | 192 |
| YYHHKKRR | 193 |
| RRKKHHYY | 194 |
| YYHHKKRRCCRRKKHHYY | 195 |
| YYHHKKRRVRRKKHHYY | 196 |
| WWRR | 197 |
| RRWW | 198 |
| CWRRRWC | 199 |
| CWWRRRWWC | 200 |
| CWRRRRWC | 201 |
| CWRRHHRRWC | 202 |
| CWWRRRRWWC | 203 |
| CWRRHHRRWWC | 204 |
| CWRRRRRWC | 205 |
| VQAAIDYING | 206 |
| CWWRRRRRWWC | 207 |
| WWRRCCRRWW | 208 |
| WWRRVRRWW | 209 |

TABLE 1-continued

Peptide Structures for Lipopeptides

| AMINO ACID SEQUENCE | SEQ ID NO: |
|---|---|
| YYRR | 210 |
| RRYY | 211 |
| CYRRRYC | 212 |
| CYYRRRYYC | 213 |
| CYRRRRYC | 214 |
| CYRRHHRRYC | 215 |
| CYYRRRRYYC | 216 |
| CYYRRHHRRYYC | 217 |
| CYRRRRRYC | 218 |
| CYYRRRRRYYC | 219 |
| CYYRRRRRYYC | 220 |
| YYRRCCRRYY | 221 |
| YYRRVRRYY | 222 |
| WWRRHH | 223 |
| HHRRWW | 224 |
| WWRRHHCCHHRRWW | 225 |
| WWRRHHVHHRRWW | 226 |
| YYRRHH | 227 |
| HHRRYY | 228 |
| YYRRHHCCRRHHYY | 229 |
| YYRRHHVRRHHYY | 230 |
| WWRRR | 231 |
| RRRWW | 232 |
| WWRRRCCRRRWW | 233 |
| WWRRRVRRRWW | 234 |
| YYRRR | 235 |
| RRRYY | 236 |
| YYRRRCCRRRYY | 237 |
| YYRRRVRRRYY | 238 |
| WWRRRHH | 239 |
| HHRRRWW | 240 |
| WWRRRHHCCHHRRRWW | 241 |
| WWRRRHHVHHRRRWW | 242 |
| YYRRRHH | 243 |
| HHRRRYY | 244 |
| YYRRRHHCCRRRHHYY | 245 |
| YYRRRHHVRRRHHYY | 246 |
| WWRRRR | 247 |
| RRRRWW | 248 |
| WWRRRRCCRRRRWW | 249 |
| WWRRRRVRRRRWW | 250 |
| YYRRRR | 251 |
| RRRRYY | 252 |
| YYRRRRCCRRRRYY | 253 |
| YYRRRRVRRRRYY | 254 |
| WWRRRRHH | 255 |
| HHRRRRWW | 256 |
| WWRRRRHHCCHHRRRRWW | 257 |
| WWRRRRHHVHHRRRRWW | 258 |
| YYRRRRHH | 259 |
| HHRRRRYY | 260 |
| YYRRRRHHCCRRRRHHYY | 261 |
| YYRRRRHHVRRRRHHYY | 262 |
| WWHHKKRRWVWRRKKHHWW | 263 |
| WWHHRRC | 264 |
| WWHHRRVRRHHWW | 265 |
| WWHHHRRRC | 266 |
| CWWHHHRRRC | 267 |
| CWWWHHHHRRR | 268 |
| CWWWKKRRR | 269 |
| CKKKWRRW | 270 |
| CWRRRWRR | 271 |
| CWWHHKKRRC | 272 |
| WWCHHKKCRR | 273 |
| WWHHCKKRRC | 274 |
| CWWHHKKRR | 275 |
| WWHHCCKKRR | 276 |
| RRWWKKHHC | 277 |
| CWWHHKKKKC | 278 |
| CWWHHRRRRC | 279 |
| CRRRHHC | 280 |
| CHHKKKKC | 281 |
| CHHRRRRC | 282 |
| CYYRRRRHHC | 283 |

TABLE 1-continued

Peptide Structures for Lipopeptides

| AMINO ACID SEQUENCE | SEQ ID NO: |
|---|---|
| CYYKKKKHHC | 284 |
| CWK$_n$C where n is from 1-20 | 285 |
| CHWK$_n$C where n is from 1-20 | 286 |
| AAABX$_{aa}$YX$_{aa}$QWLX$_{aa}$X$_{aa}$X$_{aa}$GPX$_{aa}$ where X$_{aa}$ is any amino acid | 287 |
| CK$_n$C where n is from 1-20 | 288 |
| CHK$_n$HC where n is from 1-20 | 289 |

Examples of the central peptide of lipopeptides of this disclosure include those shown in Table 2.

TABLE 2

Peptide Structures for Lipopeptides

| AMINO ACID SEQUENCE | SEQ ID NO: |
|---|---|
| GALFLAFLAAALSLMGLWSQPKKKRKV | 290 |
| GALFLAFLAAALX$_{aa}$LMGLWX$_{aa}$QX$_{aa}$KKKRKV | 291 |
| WSQPKKKRKV | 292 |
| X$_{aa}$WSQPKKKRKVX$_{aa}$ | 293 |
| WX$_{aa}$QPKKKRKX$_{aa}$ | 294 |
| X$_{aa}$X$_{aa}$QPKKKRKV | 295 |
| LIRLWSHLIHIWFQNRRLKWKKK | 296 |
| LIRLWX$_{aa}$HLIHIWFQX$_{aa}$RRLKWKKK | 297 |
| QNRRLKWKKK | 298 |
| X$_{aa}$QNRRLKWKKKX$_{aa}$ | 299 |
| QX$_{aa}$RRLKWKKK | 300 | where X$_{aa}$ in Table 2 is independently, for each occurrence, L, A, Q, H, E, R, or K.

The amino acid residues of this disclosure may be D- or L-stereocenters.

Non-cationic lipopeptides can be prepared where, for example, the central peptide contains only leucine, valine, alanine, serine, or combinations thereof.

Lipopeptides of this disclosure can be prepared where, for example, the central peptide may be cell or tissue specific targeting peptide. For example, the peptide may be a ligand or fragment thereof that interacts with a cell surface receptor or a peptide the selectively binds to lipids, peptides, sugars and combinations thereof on the cell surface of a particular cell or tissue type. The central peptide may target one or more of the following cell types: hepatocytes, endothelial, neuronal, cardiomyocytes, skeletal muscle cells (myoblast or myotube), smooth muscle cells, fibroblasts, erythrocytes, T-cells, B-cells, leukocytes, osteoblasts, chondrocytes, adult stem cells, embryonic stem cells, and tumor cells.

Lipopeptides of this disclosure can be prepared where, for example, the central peptide may be a fusogenic peptide or fragment thereof.

Lipopeptides of this disclosure can be prepared where, for example, the central peptide may be a SNARE (soluble NSF attachment receptor) peptide or fragment thereof. For example, the central peptide may be a v-SNARE or t-SNARE. The central peptide may be a NSF (N-ethylmaleimide-sensitive factor) or SNAP (soluble NSF attachment protein).

In some embodiments, a range of lipopeptides corresponding to Formula I are represented by Structure 1

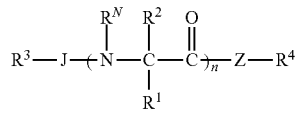

Structure 1 where $R^1$, $R^2$, $R^N$, J, Z, $R^3$, $R^4$, and n are defined as above.

In some embodiments, $R^2$, $R^N$, $R^3$ and $R^4$ may independently, for each occurrence, be C14alkyl, C16alkyl, C18alkyl, or (C18:1)alkenyl.

In some embodiments, $R^2$, $R^N$, $R^3$ and $R^4$ may independently, for each occurrence, be lipoid groups.

In some embodiments, $R^2$, $R^N$, $R^3$ and $R^4$ may independently, for each occurrence, selected lipid-like tails which impart sufficient lipophilic character or lipophilicity, such as defined by water/octanol partitioning, to provide delivery across a membrane or uptake by a cell. In some embodiments, $R^2$, $R^N$, $R^3$ and $R^4$ may independently, for each occurrence, selected lipid-like tails which impart sufficient lipophilic character or lipophilicity to provide cell membrane anchoring. These tails provide, when used in an amino acid lipid structure, an amphipathic molecule. Lipid-like tails may be derived from phospholipids, glycolipids, triacylglycerols, glycerophospholipids, sphingolipids, ceramides, sphingomyelins, cerebrosides, or gangliosides, among others, and may contain a steroid.

In certain embodiments, $R^2$, $R^N$, $R^3$ and $R^4$ may independently, for each occurrence, be a lipid-like tail having a glycerol backbone.

In some embodiments, $R^2$, $R^N$, $R^3$ and $R^4$ may independently, for each occurrence, be C3alkyl, C4alkyl, C5alkyl, C6alkyl, C7alkyl, C8alkyl, C9alkyl, C10alkyl, C11alkyl, C12alkyl, C13 alkyl, C14alkyl, C15 alkyl, C16alkyl, C17alkyl, C18alkyl, C19alkyl, C20alkyl, C21alkyl, or C22alkyl.

In some embodiments, $R^2$, $R^N$, $R^3$ and $R^4$ may independently, for each occurrence, be lipophilic tails having one of the following structures:

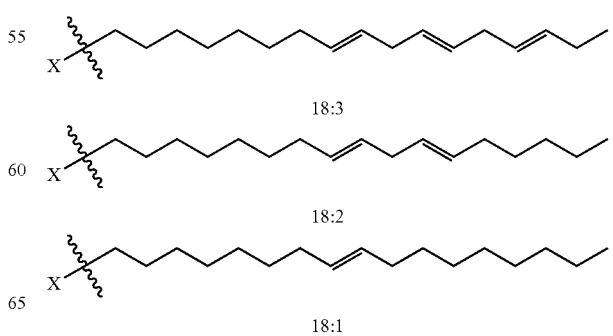

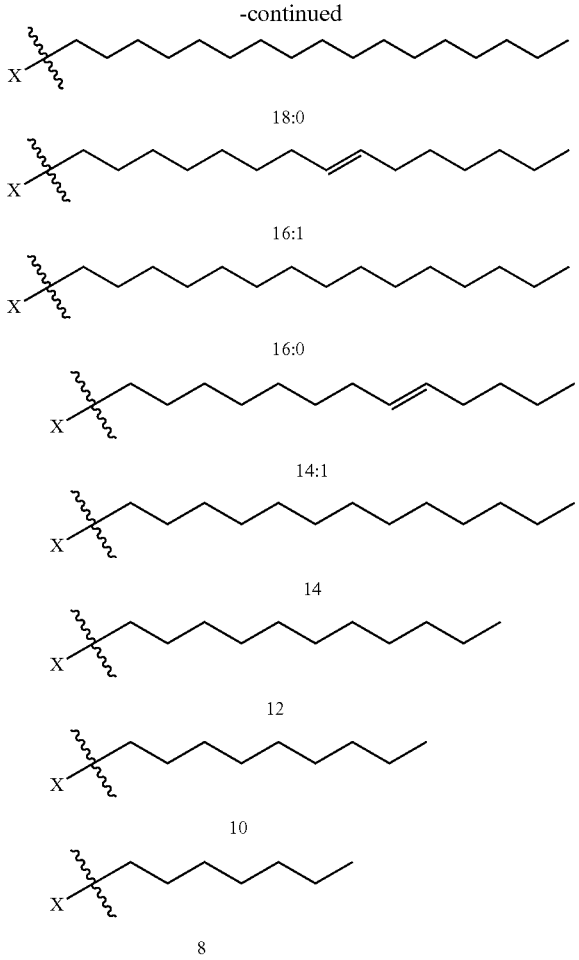

In the structures above, X represents Z, J, N, or the alpha-carbon of Structure I above, and is counted as one of the atoms in the numerical designation, for example, "18:3." In some embodiments, X may be a carbon, nitrogen, or oxygen atom.

In some embodiments, $R^2$, $R^N$, $R^3$ and $R^4$ may independently, for each occurrence, be lipophilic tails having one of the following structures:

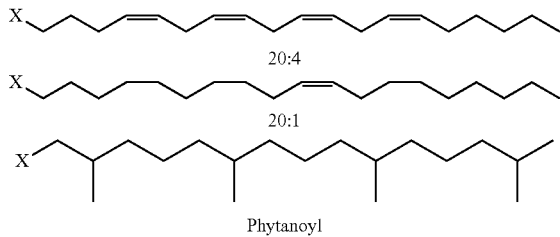

where X is as defined above.

In some embodiments, $R^2$, $R^N$, $R^3$ and $R^4$ may independently, for each occurrence, be selected lipid-like tails which may contain a cholesterol, a sterol, or a steroid such as gonanes, estranes, androstanes, pregnanes, cholanes, cholestanes, ergostanes, campestanes, poriferastanes, stigmastanes, gorgostanes, lanostanes, cycloartanes, as well as sterol or zoosterol derivatives of any of the foregoing, and their biological intermediates and precursors, which may include, for example, cholesterol, lanosterol, stigmastanol, dihydrolanosterol, zymosterol, zymostenol, desmosterol, 7-dehydrocholesterol, and mixtures and derivatives thereof.

In certain embodiments, $R^2$, $R^N$, $R^3$ and $R^4$ may independently, for each occurrence, be derived from fatty acid-like tails such as tails from myristic acid (C14:0)alkenyl, palmitic acid (C16:0)alkenyl, stearic acid (C18:0)alkenyl, oleic acid (C18:1, double bond at carbon 9)alkenyl, linoleic acid (C18:2, double bond at carbon 9 or 12)alkenyl, linonenic acid (C18:3, double bond at carbon 9, 12, or 15)alkenyl, arachidonic acid (C20:4, double bond at carbon 5, 8, 11, or 14)alkenyl, and eicosapentaenoic acid (C20:5, double bond at carbon 5, 8, 11, 14, or 17)alkenyl. Other examples of fatty acid-like tails are found at Donald Voet and Judith Voet, *Biochemistry*, 3rd Edition (2005), p. 383.

In some embodiments, $R^2$, $R^N$, $R^3$ and $R^4$ may independently, for each occurrence, be derived from an isoprenoid.

In some embodiments, $R^3$ may be a lipophilic group, as described above, and $R^2$, $R^N$, and $R^4$ may be hydrogen.

In some embodiments, $R^4$ may be a lipophilic group, as described above, and $R^2$, $R^N$, and $R^3$ may be hydrogen.

In some embodiments, $R^3$ and $R^4$ may be a lipophilic group, as described above, and $R^2$ and $R^N$ may be hydrogen.

In some embodiments, $R^3$, $R^4$, $R^2$ may be a lipophilic group, as described above, and $R^N$ may be hydrogen.

In some embodiments, $R^3$, $R^4$, $R^N$ may be a lipophilic group, as described above, and $R^2$ may be hydrogen.

In some embodiments, $R^3$ and $R^N$ may be a lipophilic group, as described above, and $R^2$ and $R^4$ may be hydrogen.

In some embodiments, $R^N$ and $R^4$ may be a lipophilic group, as described above, and $R^2$ and $R^3$ may be hydrogen.

In some embodiments, $R^N$ and $R^2$ may be a lipophilic group, as described above, and $R^3$ and $R^4$ may be hydrogen.

In some embodiments, $R^4$ and $R^2$ may be a lipophilic group, as described above, and $R^3$ and $R^N$ may be hydrogen.

In some embodiments, $R^3$ and $R^2$ may be a lipophilic group, as described above, and $R^4$ and $R^N$ may be hydrogen.

In some embodiments, a lipophilic group may be linked to the alpha-carbon of any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 sequential amino acid residues. In some embodiments, a lipophilic group may be linked to the alpha-carbon of every other amino acid residue of the central peptide. In some embodiments, a lipophilic group may be linked to the alpha-carbon of any two sequential amino acid residues of the central peptide where the two sequential amino acid residues are each adjacent to an amino acid residue within the central peptide that do not have a lipophilic group linked to its alpha-carbon.

In some embodiments, a lipophilic group may be linked to the amine group of any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 sequential amino acid residues where the amine groups is adjacent to the alpha-carbon of the amino acid residue of the central peptide. In some embodiments, a lipophilic group may be linked to the amine group of every other amino acid residue of the central peptide. In some embodiments, a lipophilic group may be linked to the amine group of any two sequential amino acid residues of the central peptide where the two sequential amino acid residues are each adjacent to an amino acid residue within the central peptide that do not have a lipophilic group linked to its amine group where the amine group is adjacent to the alpha-carbon of the amino acid residue of the central peptide.

In some embodiments, a range of lipopeptides corresponding to Formula I are represented by Structure 2, where z is from 0 to 20 (or 0, 1, 2, 3, 4, 5, 6, 7, 8, 9, 10, 11, 12, 13, 14, 15, 16, 17, 18, 19, or 20), X is independently, for each occurrence, any amino acid, $R^1$ is defined above, and n is from 0 to 98 (or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, or 98).

Structure 2

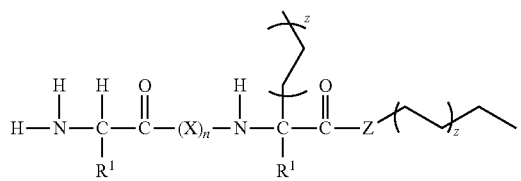

In some embodiments, a range of lipopeptides corresponding to Formula I are represented by Structure 3, where z is from 0 to 20, X is independently, for each occurrence, any amino acid, $R^1$ is defined above, and n is from 0 to 98.

Structure 3

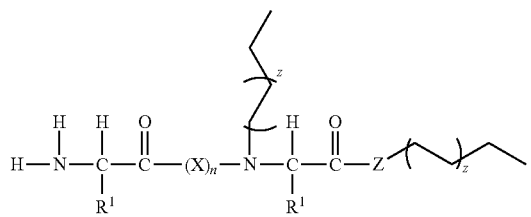

In some embodiments, a range of lipopeptides corresponding to Formula I are represented by Structure 4, where z is from 0 to 20, X is independently, for each occurrence, any amino acid, $R^1$ is defined above, and n is from 0 to 98.

Structure 4

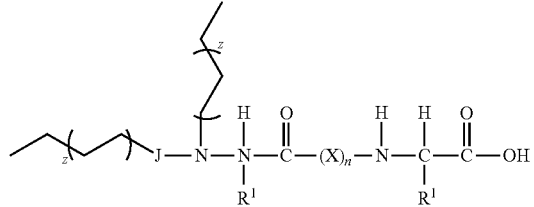

In some embodiments, a range of lipopeptides corresponding to Formula I are represented by Structure 5, where z is from 0 to 20, X is independently, for each occurrence, any amino acid, $R^1$ is defined above, and n is from 0 to 98.

Structure 5

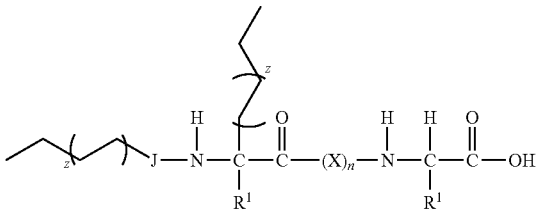

In some embodiments, a range of lipopeptides corresponding to Formula I are represented by Structure 6, where z is from 0 to 20, X is independently, for each occurrence, any amino acid, $R^1$ is defined above, and n is from 0 to 98.

Structure 6

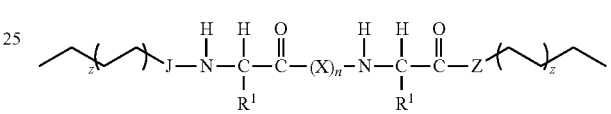

In some embodiments, a range of lipopeptides corresponding to Formula I are represented by Structure 7, where z is from 0 to 20, X is independently, for each occurrence, any amino acid, $R^1$ is defined above, and n is from 0 to 98.

Structure 7

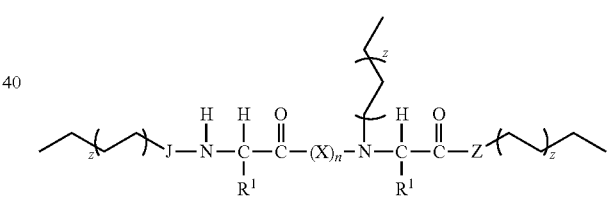

In some embodiments, a range of lipopeptides corresponding to Formula I are represented by Structure 8, where z is from 0 to 20, X is independently, for each occurrence, any amino acid, $R^1$ is defined above, and n is from 0 to 98.

Structure 8

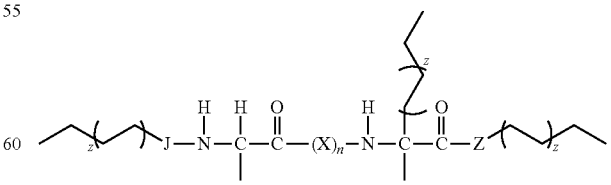

In some embodiments, a range of lipopeptides corresponding to Formula I are represented by Structure 9, where z is from 0 to 20, X is independently, for each occurrence, any amino acid, $R^1$ is defined above, and n is from 0 to 98.

Structure 9

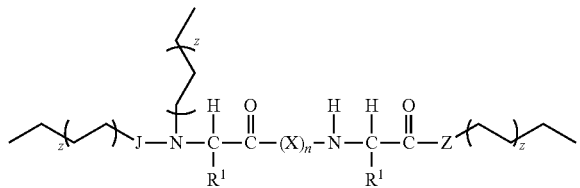

In some embodiments, a range of lipopeptides corresponding to Formula I are represented by Structure 10, where z is from 0 to 20, X is independently, for each occurrence, any amino acid, $R^1$ is defined above, and n is from 0 to 98.

Structure 10

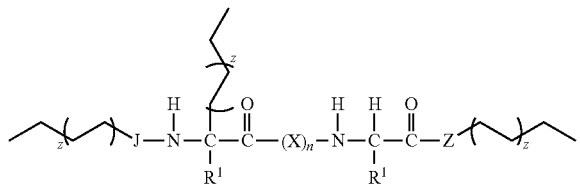

In some embodiments, a range of lipopeptides corresponding to Formula I are represented by Structure 11, where z is from 0 to 20, X is independently, for each occurrence, any amino acid, $R^1$ is defined above, and n is from 0 to 98.

Structure 11

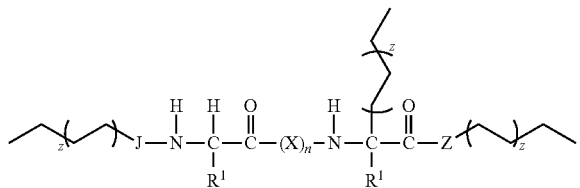

In some embodiments, a range of lipopeptides corresponding to Formula I are represented by Structure 12, where z is from 0 to 20, X is independently, for each occurrence, any amino acid, $R^1$ is defined above, and n is from 0 to 98.

Structure 12

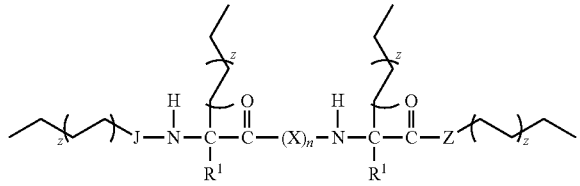

In some embodiments, a range of lipopeptides corresponding to Formula I are represented by Structure 13, where z is from 0 to 20, X is independently, for each occurrence, any amino acid, $R^1$ is defined above, and n is from 0 to 98.

Structure 13

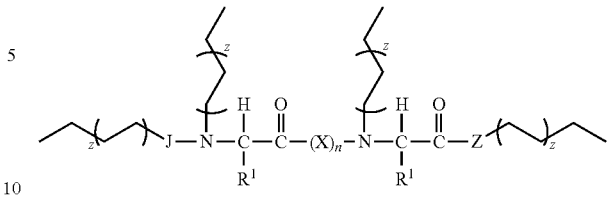

In some embodiments, a range of lipopeptides corresponding to Formula I are represented by Structure 14, where z is from 0 to 20, X is independently, for each occurrence, any amino acid, $R^1$ is defined above, and n is from 0 to 98.

Structure 14

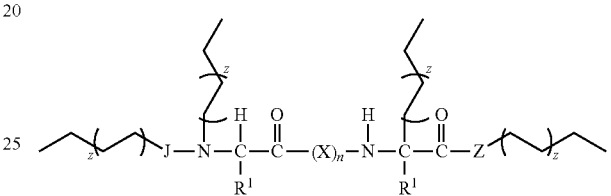

In some embodiments, a range of lipopeptides corresponding to Formula I are represented by Structure 15, where z is from 0 to 20, X is independently, for each occurrence, any amino acid, $R^1$ is defined above, and n is from 0 to 98.

Structure 15

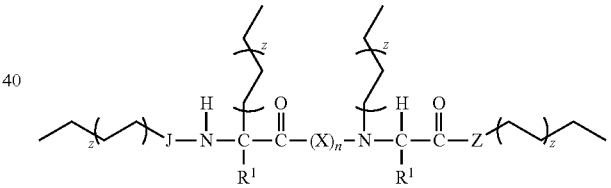

As used herein, the term "amino acid" includes naturally-occurring and non-naturally occurring amino acids. Examples of amino acids include Ala, Arg, Asn, Asp, Cys, Gln, Glu, Gly, His, Ile, Leu, Lys, Met, Phe, Pro, Ser, Thr, Trp, Tyr, and Val. Thus, a lipopeptide of this invention can be made from a genetically encoded amino acid, a naturally occurring non-genetically encoded amino acid, or a synthetic amino acid. Some examples of amino acids include 2-aminoadipic acid, 3-aminoadipic acid, 2,3-diaminopropionic acid, 2-aminobutyric acid, 4-aminobutyric acid, 2,3-diaminobutyric acid, 2,4-diaminobutyric acid, 2-aminoisobutyric acid, 4-aminoisobutyric acid, 2-aminopimelic acid, 2,2'-diaminopimelic acid, 6-aminohexanoic acid, 6-aminocaproic acid, 2-aminoheptanoic acid, desmosine, ornithine, citrulline, N-methylisoleucine, norleucine, tert-leucine, phenylglycine, t-butylglycine, N-methylglycine, sarcosine, N-ethylglycine, cyclohexylglycine, 4-oxo-cyclohexylglycine, N-ethylasparagine, cyclohexylalanine, t-butylalanine, naphthylalanine, pyridylalanine, 3-chloroalanine, 3-benzothienylalanine, 4-halophenylalanine, 4-chlorophenylalanine, 2-fluorophenylalanine, 3-fluorophenylalanine, 4-fluorophenylalanine, penicillamine, 2-thienylalanine, methionine, methionine sulfoxide, homoarginine, norarginine, nor-norarginine, N-acetyllysine, N-aminophenylalanine, N-methylvaline, homocysteine, homoserine, hydroxylysine, allo-hydroxylysine, 3-hydroxyproline, 4-hydroxyproline, isodesmosine, allo-isoleucine, 6-N-methyllysine, norvaline, 0-allyl-serine, 0-allyl-threonine, alpha-aminohexanoic acid, alpha-aminovaleric acid, and pyroglutamic acid.

As used herein, the term "amino acid" includes alpha- and beta-amino acids.

Other amino acid residues can be found in Fasman, *CRC Practical Handbook of Biochemistry and Molecular Biology*, CRC Press, Inc. (1989).

In general, a compound may contain one or more chiral centers. Compounds containing one or more chiral centers may include those described as an "isomer," a "stereoisomer," a "diastereomer," an "enantiomer," an "optical isomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, for example, Michael B. Smith and Jerry March "March's Advanced Organic Chemistry", 5th edition, 2001. The compounds and structures of this disclosure are meant to encompass all possible isomers, stereoisomers, diastereomers, enantiomers, and/or optical isomers that would be understood to exist for the specified compound or structure, including any mixture, racemic or otherwise, thereof.

The term "lipophilic group" or "lipoid group" or "lipid-like tail" or "lipophilic tail" as used herein refers to an alkyl, cycloalkyl, alkenyl, alkynyl, alkoxy, alkanoyl, alkylamino, aryl, acyl, heteroaryl, heterocycle, heterocyclyl, alkanoyloxy, alkylamino, alkylaminoalkyl, aroyl, and aralkyl group including substituted variations thereof.

The term "alkyl" as used herein refers to a saturated, branched or unbranched, substituted or unsubstituted aliphatic group containing from 1-22 carbon atoms. This definition applies to the alkyl portion of other groups such as, for example, alkoxy, alkanoyl, aralkyl, and other groups defined below. The term "cycloalkyl" as used herein refers to a saturated, substituted or unsubstituted cyclic alkyl ring containing from 3 to 12 carbon atoms. The term "alkenyl" as used herein refers to an unsaturated, branched or unbranched, substituted or unsubstituted alkyl or cycloalkyl having 2 to 22 carbon atoms and at least one carbon-carbon double bond. The term "alkynyl" as used herein refers to an unsaturated, branched or unbranched, substituted or unsubstituted alkyl or cycloalkyl having 2 to 22 carbon atoms and at least one carbon-carbon triple bond.

The term "alkoxy" as used herein refers to an alkyl, cycloalkyl, alkenyl, or alkynyl group covalently bonded to an oxygen atom. The term "alkanoyl" as used herein refers to —C(=O)-alkyl, which may alternatively be referred to as "acyl." The term "alkanoyloxy" as used herein refers to —O—C(=O)-alkyl groups. The term "alkylamino" as used herein refers to the group —NRR', where R and R' are each either hydrogen or alkyl, and at least one of R and R' is alkyl. Alkylamino includes groups such as piperidino wherein R and R' form a ring. The term "alkylaminoalkyl" refers to -alkyl-NRR'.

The term "aryl" as used herein refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

The term "heteroaryl" as used herein refers to any stable monocyclic, bicyclic, or polycyclic carbon ring system of from 4 to 12 atoms in each ring, wherein at least one ring is aromatic and contains from 1 to 4 heteroatoms selected from oxygen, nitrogen and sulfur. Some examples of a heteroaryl include acridinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, and tetrahydroquinolinyl. A heteroaryl includes the N-oxide derivative of a nitrogen-containing heteroaryl.

The term "heterocycle" or "heterocyclyl" as used herein refers to an aromatic or nonaromatic ring system of from five to twenty-two atoms, wherein from 1 to 4 of the ring atoms are heteroatoms selected from oxygen, nitrogen, and sulfur. Thus, a heterocycle may be a heteroaryl or a dihydro or tetrahydro version thereof.

The term "aroyl" as used herein refers to an aryl radical derived from an aromatic carboxylic acid, such as a substituted benzoic acid. The term "aralkyl" as used herein refers to an aryl group bonded to an alkyl group, for example, a benzyl group.

The term "carboxyl" as used herein represents a group of the formula —C(=O)OH or —C(=O)O⁻. The terms "carbonyl" and "acyl" as used herein refer to a group in which an oxygen atom is double-bonded to a carbon atom >C=O. The term "hydroxyl" as used herein refers to —OH or —O⁻. The term "nitrile" or "cyano" as used herein refers to —CN. The term "halogen" or "halo" refers to fluoro (—F), chloro (—Cl), bromo (—Br), and iodo (—I).

The term "substituted" as used herein refers to an atom having one or more substitutions or substituents which can be the same or different and may include a hydrogen substituent. Thus, the terms alkyl, cycloalkyl, alkenyl, alkynyl, alkoxy, alkanoyl, alkanoyloxy, alkylamino, alkylaminoalkyl, aryl, heteroaryl, heterocycle, aroyl, and aralkyl as used herein refer to groups which include substituted variations. Substituted variations include linear, branched, and cyclic variations, and groups having a substituent or substituents replacing one or more hydrogens attached to any carbon atom of the group. Substituents that may be attached to a carbon atom of the group include alkyl, cycloalkyl, alkenyl, alkynyl, alkoxy, alkanoyl, alkanoyloxy, alkylamino, alkylaminoalkyl, aryl, heteroaryl, heterocycle, aroyl, aralkyl, acyl, hydroxyl, cyano, halo, haloalkyl, amino, aminoacyl, alkylaminoacyl, acyloxy, aryloxy, aryloxyalkyl, mercapto, nitro, carbamyl, carbamoyl, and heterocycle. For example, the term ethyl includes without limitation —CH₂CH₃, —CHFCH₃, —CF₂CH₃, —CHFCH₂F, —CHFCHF₂, —CHFCF₃, —CF₂CH₂F, —CF₂CHF₂, —CF₂CF₃, and other variations as described above.

A pharmaceutically acceptable salt of a peptide or protein composition of this invention which is sufficiently basic may be an acid-addition salt with, for example, an inorganic or organic acid such as hydrochloric, hydrobromic, sulfuric, nitric, phosphoric, chlorosulfonic, trifluoroacetic, citric, maleic, acetic, propionic, oxalic, malic, maleic, malonic, fumaric, or tartaric acids, and alkane- or arenesulfonic acids such as methanesulfonic, ethanesulfonic, benzenesulfonic, chlorobenzenesulfonic, toluenesulfonic, naphthalenesulfonic, naphthalenedisulfonic, and camphorsulfonic acids.

A pharmaceutically acceptable salt of a peptide or protein composition of this invention which is sufficiently acidic may be an alkali metal salt, for example, a sodium or potassium salt, or an alkaline earth metal salt, for example, a calcium or magnesium salt, or an ammonium salt or a salt with an organic base which provides a physiologically-acceptable cation, for example, a salt with methylamine, dimethylamine, trimethylamine, triethylamine, ethanolamine, diethanolamine, triethanolamine, ethylenediamine, tromethamine, N-methylglucamine, piperidine, morpholine or tris-(2-hydroxyethyl)amine. See, for example, Berge et al., *J. Pharm. Sci.* 66:1, 1971.

Some compounds, peptides and/or protein compositions of this invention may have one or more chiral centers and/or geometric isomeric centers (E- and Z-isomers), and it is to be understood that the invention encompasses all such optical isomers, diastereoisomers and geometric isomers.

This invention encompasses any and all tautomeric, solvated or unsolvated, and hydrated or unhydrated forms of the compounds, peptides and/or protein compositions disclosed herein.

Embodiments of this invention include compounds described above, wherein a functional group is linked to a side chain of the central peptide, wherein the functional group is selected from the side chain of 3,5-diiodo-tyrosine, 1-methylhistidine, and 2-methylbutanoic acid, or is selected from 2-o-anisylpropanoic acid, meso-tartaric acid, 4,6-dimethylpyrimidinamine, p-phthalic acid, creatinine, butanoic acid, N,N-dimethyl-1-naphthylamine, pentanoic acid, 4-methylpentanoic acid, N-methylaniline, 1,10-phenanthroline, 3-pyridinecarboxylic acid, hexanoic acid, propanoic acid, 4-animobenzoic acid, 2-methylpropanoic acid, heptanoic acid, octanoic acid, cyclohexanecarboxylic acid, quinoline, 3-quinolinamine, 2-aminobenzoic acid, 4-pyridinecarboxylic acid, nonanoic acid, melamine, 8-quinolinol, trimethylacetic acid, 6-methoxyquinoline, 4-(methylamino) benzoic acid, p-methylaniline, 3-(methylamino)benzoic acid, malic acid, N-ethylaniline, 2-benzylpyridine, 3,6-dinitrophenol, N,N-dimethylaniline, 2,5-dimethylpiperazine, p-phenetidine, 5-methylquinoline, 2-phenylbenzimidazole, pyridine, picolinic acid, p-anisidine, 2-(methylamino)benzoic acid, 2-thiazolamine, glutaric acid, adipic acid, isoquinoline, itaconic acid, o-phthalic acid, benzimidazole, piperazine, heptanedioic acid, acridine, phenanthridine, succinic acid, methylsuccinic acid, 4-methylquinoline, 3-methylpyridine, 7-isoquinolinol, malonic acid, methylmalonic acid, 2-methylquinoline, 2-ethylpyridine, 2-methylpyridine, 4-methylpyridine, histamine, histidine, maleic acid, cis-1,2-cyclohexanediamine, 3,5-dimethylpyridine, 2-ethylbenzimidazole, 2-methylbenzimidazole, cacodylic acid, perimidine, citric acid, isocitric acid, 2,5-dimethylpyridine, papaverine, 6-hydroxy-4-methylpteridine, L-thyroxine, 3,4-dimethylpyridine, methoxypyridine, trans-1,2-cyclohexanediamine, 2,5-pyridinediamine, 1-1-methylhistidine, 1-3-methylhistidine, 2,3-dimethylpyridine, xanthopterin, 1,2-propanediamine, N,N-diethylaniline, alloxanic acid, 2,6-dimethylpyridine, L-carnosine, 2-pyridinamine, N-b-alanylhistidine, pilocarpine, 1-methylimidazol, 1H-imidazole, 2,4-dimethylpyridine, 4-nitrophenol, 2-nitrophenol, tyrosineamide, 5-hydoxyquinazoline, 1,1-cyclopropanedicarboxylic acid, 2,4,6-trimethylpyridine, 2,3-dichlorophenol, 1,2-ethanediamine, 1-isoquinolinamine, and combinations thereof. Embodiments of this invention include a pharmaceutical composition comprising a nucleic acid agent and one or more compounds described above, and pharmaceutically acceptable salts thereof.

Uses for Regulatory RNA and RNA Interference

In some aspects, this disclosure relates generally to the fields of regulatory RNA and RNA interference, antisense therapeutics, and delivery of RNA therapeutics. More particularly, this invention relates to compositions and formulations for ribonucleic acids, and their uses for medicaments and for delivery as therapeutics. This invention relates generally to methods of using ribonucleic acids in RNA interference for gene-specific inhibition of gene expression in cells, or in mammals to alter a disease state or a phenotype.

RNA interference refers to methods of sequence-specific post-transcriptional gene silencing which is mediated by a double-stranded RNA (dsRNA) called a short interfering RNA (siRNA). See Fire, et al., *Nature* 391:806, 1998, and Hamilton, et al., *Science* 286:950-951, 1999. RNAi is shared by diverse flora and phyla and is believed to be an evolutionarily-conserved cellular defense mechanism against the expression of foreign genes. See Fire, et al., *Trends Genet.* 15:358, 1999.

RNAi is therefore a ubiquitous, endogenous mechanism that uses small noncoding RNAs to silence gene expression. See Dykxhoorn, D. M. and J. Lieberman, *Annu. Rev. Biomed. Eng.* 8:377-402, 2006. RNAi can regulate important genes involved in cell death, differentiation, and development. RNAi may also protect the genome from invading genetic elements, encoded by transposons and viruses. When a siRNA is introduced into a cell, it binds to the endogenous RNAi machinery to disrupt the expression of mRNA containing complementary sequences with high specificity. Any disease-causing gene and any cell type or tissue can potentially be targeted. This technique has been rapidly utilized for gene-function analysis and drug-target discovery and validation. Harnessing RNAi also holds great promise for therapy, although introducing siRNAs into cells in vivo remains an important obstacle.

The mechanism of RNAi, although not yet fully characterized, is through cleavage of a target mRNA. The RNAi response involves an endonuclease complex known as the RNA-induced silencing complex (RISC), which mediates cleavage of a single-stranded RNA complementary to the antisense strand of the siRNA duplex. Cleavage of the target RNA takes place in the middle of the region complementary to the antisense strand of the siRNA duplex (Elbashir, et al., *Genes Dev.* 15:188, 2001).

One way to carry out RNAi is to introduce or express a siRNA in cells. Another way is to make use of an endogenous ribonuclease III enzyme called dicer. One activity of dicer is to process a long dsRNA into siRNAs. See Hamilton, et al., *Science* 286:950-951, 1999; Berstein, et al., *Nature* 409:363, 2001. A siRNA derived from dicer is typically about 21-23 nucleotides in overall length with about 19 base pairs duplexed. See Hamilton, et al., supra; Elbashir, et al., *Genes Dev.* 15:188, 2001. In essence, a long dsRNA can be introduced in a cell as a precursor of a siRNA.

This invention provides a range of compositions, formulations and methods which include a regulatory RNA, an interfering nucleic acid or a precursor thereof in combination with various components including lipids, amino acid lipids, and natural or synthetic polymers.

The term "dsRNA" as used herein refers to any nucleic acid molecule comprising at least one ribonucleotide molecule and capable of inhibiting or down regulating gene expression, for example, by promoting RNA interference ("RNAi") or gene silencing in a sequence-specific manner. The dsRNAs of this disclosure may be suitable substrates for Dicer or for association with RISC to mediate gene silencing by RNAi. One or both strands of the dsRNA can further comprise a terminal phosphate group, such as a 5'-phosphate or 5',3'-diphosphate. As used herein, dsRNA molecules, in addition to at least one ribonucleotide, can further include substitutions, chemically-modified nucleotides, and non-nucleotides. In certain embodiments, dsRNA molecules comprise ribonucleotides up to about 100% of the nucleotide positions.

Examples of dsRNA molecules can be found in, for example, U.S. patent application Ser. No. 11/681,725, U.S. Pat. Nos. 7,022,828 and 7,034,009, and PCT International Application Publication No. WO/2003/070897.

In addition, as used herein, the term "dsRNA" is meant to be synonymous with other terms used to describe nucleic acid molecules that are capable of mediating sequence specific RNAi, for example, meroduplex RNA (mdRNA), nicked dsRNA (ndsRNA), gapped dsRNA (gdsRNA), short interfering nucleic acid (siNA), siRNA, micro-RNA (miRNA), short hairpin RNA (shRNA), short interfering oligonucleotide, short interfering substituted oligonucleotide, short interfering modified oligonucleotide, chemically-modified dsRNA, post-transcriptional gene silencing RNA (ptgsRNA), among others. The term "large double-stranded (ds) RNA" refers to any double-stranded RNA longer than about 40 base pairs (bp) to about 100 bp or more, particularly up to about 300 bp to about 500 bp. The sequence of a large dsRNA may represent a segment of an mRNA or an entire mRNA. A double-stranded structure may be formed by self-complementary nucleic acid molecule or by annealing of two or more distinct complementary nucleic acid molecule strands.

In some aspects, a dsRNA comprises two separate oligonucleotides, comprising a first strand (antisense) and a second strand (sense), wherein the antisense and sense strands are self-complementary (i.e., each strand comprises a nucleotide sequence that is complementary to a nucleotide sequence in the other strand and the two separate strands form a duplex or double-stranded structure, for example, wherein the double-stranded region is about 15 to about 24 base pairs or about 26 to about 40 base pairs); the antisense strand comprises a nucleotide sequence that is complementary to a nucleotide sequence in a target nucleic acid molecule or a portion thereof (e.g., a human mRNA); and the sense strand comprises a nucleotide sequence corresponding (i.e., homologous) to the target nucleic acid sequence or a portion thereof (e.g., a sense strand of about 15 to about 25 nucleotides or about 26 to about 40 nucleotides corresponds to the target nucleic acid or a portion thereof).

In some aspects, the dsRNA may be assembled from a single oligonucleotide in which the self-complementary sense and antisense strands of the dsRNA are linked by together by a nucleic acid based-linker or a non-nucleic acid-based linker. In some embodiments, the first (antisense) and second (sense) strands of the dsRNA molecule are covalently linked by a nucleotide or non-nucleotide linker as described herein and known in the art. In some embodiments, a first dsRNA molecule is covalently linked to at least one second dsRNA molecule by a nucleotide or non-nucleotide linker known in the art, wherein the first dsRNA molecule can be linked to a plurality of other dsRNA molecules that can be the same or different, or any combination thereof. In some embodiments, the linked dsRNA may include a third strand that forms a meroduplex with the linked dsRNA.

In some respects, dsRNA molecules described herein form a meroduplex RNA (mdRNA) having three or more strands, for example, an 'A' (first or antisense) strand, 'S1' (second) strand, and 'S2' (third) strand in which the 'S1' and 'S2' strands are complementary to and form base pairs (bp) with non-overlapping regions of the 'A' strand (e.g., an mdRNA can have the form of A:S1S2). The S1, S2, or more strands together essentially comprise a sense strand to the 'A' strand. The double-stranded region formed by the annealing of the 'S1' and 'A' strands is distinct from and non-overlapping with the double-stranded region formed by the annealing of the 'S2' and 'A' strands. An mdRNA molecule is a "gapped" molecule, meaning a "gap" ranging from 0 nucleotides up to about 10 nucleotides. In some embodiments, the A:S1 duplex is separated from the A:S2 duplex by a gap resulting from at least one unpaired nucleotide (up to about 10 unpaired nucleotides) in the 'A' strand that is positioned between the A:S1 duplex and the A:S2 duplex and that is distinct from any one or more unpaired nucleotide at the 3'-end of one or more of the 'A', 'S1', or 'S2' strands. In some embodiments, the A:S1 duplex is separated from the A:B2 duplex by a gap of zero nucleotides (i.e., a nick in which only a phosphodiester bond between two nucleotides is broken or missing in the polynucleotide molecule) between the A:S1 duplex and the A:S2 duplex— which can also be referred to as nicked dsRNA (ndsRNA). For example, A:S1S2 may be comprised of a dsRNA having at least two double-stranded regions that combined total about 14 base pairs to about 40 base pairs and the double-stranded regions are separated by a gap of about 0 to about 10 nucleotides, optionally having blunt ends, or A:S1S2 may comprise a dsRNA having at least two double-stranded regions separated by a gap of up to 10 nucleotides wherein at least one of the double-stranded regions comprises between about 5 base pairs and 13 base pairs.

As described herein, a dsRNA molecule which contains three or more strands may be referred to as a "meroduplex" RNA (mdRNA). Examples of mdRNA molecules can be found in U.S. Provisional Patent Application Nos. 60/934,930 and 60/973,398.

A dsRNA or large dsRNA may include a substitution or modification in which the substitution or modification may be in a phosphate backbone bond, a sugar, a base, or a nucleoside. Such nucleoside substitutions can include natural non-standard nucleosides (e.g., 5-methyluridine or 5-methylcytidine or a 2-thioribothymidine), and such backbone, sugar, or nucleoside modifications can include an alkyl or heteroatom substitution or addition, such as a methyl, alkoxyalkyl, halogen, nitrogen or sulfur, or other modifications known in the art.

The term "pyrimidine" as used herein refers to conventional pyrimidine bases, including standard pyrimidine bases uracil and cytosine. In addition, the term pyrimidine is contemplated to embrace natural non-standard pyrimidine bases or acids, such as 5-methyluracil, 4-thiouracil, pseudouracil, dihydrouracil, orotate, 5-methylcytosine, or the like, as well as a chemically-modified bases or "universal bases," which can be used to substitute for a standard pyrimidine within nucleic acid molecules of this disclosure. Examples of pyrimidines suitable for use within a dsRNA of this disclosure include those disclosed in U.S. Pat. No. 6,846,827, hereby incorporated by reference.

The term "purine" as used herein refers to conventional purine bases, including standard purine bases adenine and guanine. In addition, the term purine is contemplated to embrace natural non-standard purine bases or acids, such as N2-methylguanine, inosine, 2,6-aminopurine, or the like, as well as a chemically-modified bases or "universal bases," which can be used to substitute for a standard purine within nucleic acid molecules of this disclosure.

In yet another embodiment, the mdRNA or dsRNA comprises one or more nucleotides having the formula:

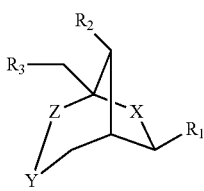

wherein, X is O or $CH_2$, Y is O, and Z is $CH_2$; $R_1$ is selected from the group consisting of adenine, cytosine, guanine, hypoxanthine, uracil, thymine, 2,6-diaminopurine, C-phenyl, C-naphthyl, inosine, azole carboxamide, 1-β-D-ribofuranosyl-4-nitroindole, 1-β-D-ribofuranosyl-5-nitroindole, 1-β-D-ribofuranosyl-6-nitroindole, or 1-β-D-ribofuranosyl-3-nitropyrrole, and a heterocycle wherein the heterocycle is selected from the group consisting of a substituted 1,3-diazine, unsubstituted 1,3-diazine, and an unsubstituted 7H imidazo[4,5]1,3 diazine; and $R_2$, $R_3$ are independently selected from a group consisting of H, OH, DMTO, TBDMSO, BnO, THPO, AcO, BzO, $OP(NiPr_2)O(CH_2)_2CN$, $OPO_3H$, diphosphate, and triphosphate, wherein $R_2$ and $R_3$ together may be $PhCHO_2$, $TIPDSO_2$ or $DTBSO_2$.

In yet another embodiment, the mdRNA or dsRNA comprises one or more are universal-binding nucleotide. Non-limiting examples of universal-binding nucleotide include C-phenyl, C-naphthyl, inosine, azole carboxamide, 1-β-D-ribofuranosyl-4-nitroindole, 1-β-D-ribofuranosyl-5-nitroindole, 1-β-D-ribofuranosyl-6-nitroindole, or 1-β-D-ribofuranosyl-3-nitropyrrole. Within certain aspects, the present disclosure provides methods of using mdRNA or dsRNA that decreases expression of a target gene by RNAi, and compositions comprising one or more mdRNA or dsRNA, wherein at least one mdRNA or dsRNA comprises one or more universal-binding nucleotide(s) in the first, second or third position in the anti-codon of the antisense strand of the mdRNA or dsRNA duplex and wherein the mdRNA or dsRNA is capable of specifically binding to a target sequence, such as an RNA expressed by a cell. In cases wherein the sequence of the target RNA includes one or more single nucleotide substitutions, mdRNA or dsRNA comprising a universal-binding nucleotide retains its capacity to specifically bind a target RNA, thereby mediating gene silencing and, as a consequence, overcoming escape of the target from mdRNA or dsRNA-mediated gene silencing.

Non-limiting examples for the above compositions includes modifying the anti-codons for tyrosine (AUA) or phenylalanine (AAA or GAA), cysteine (ACA or GCA), histidine (AUG or GUG), asparagine (AUU or GUU), isoleucine (UAU) and aspartate (AUC or GUC) within the anti-codon of the antisense strand of the mdRNA or dsRNA molecule.

For example, within certain embodiments, the isoleucine anti-codon UAU, for which AUA is the cognate codon, may be modified such that the third-position uridine (U) nucleotide is substituted with the universal-binding nucleotide inosine (I) to create the anti-codon UAI. Inosine is an exemplary universal-binding nucleotide that can nucleotide-pair with an adenosine (A), uridine (U), and cytidine (C) nucleotide, but not guanosine (G). This modified anti-codon UAI increases the specific-binding capacity of the mdRNA or dsRNA molecule and thus permits the mdRNA or dsRNA to pair with mRNAs having any one of AUA, UUA, and CUA in the corresponding position of the coding strand thereby expanding the number of available RNA degradation targets to which the mdRNA or dsRNA may specifically bind.

Alternatively, the anti-codon AUA may also or alternatively be modified by substituting a universal-binding nucleotide in the third or second position of the anti-codon such that the anti-codon(s) represented by UAI (third position substitution) or UIU (second position substitution) to generate mdRNA or dsRNA that are capable of specifically binding to AUA, CUA and UUA and AAA, ACA and AUA.

In certain aspects, mdRNA or dsRNA disclosed herein can include between about 1 universal-binding nucleotide and about 10 universal-binding nucleotides. Within certain aspects, the presently disclosed mdRNA or dsRNA may comprise a sense strand that is homologous to a sequence of a target gene and an antisense strand that is complementary to the sense strand, with the proviso that at least one nucleotide of the antisense strand of the otherwise complementary mdRNA or dsRNA duplex is replaced by one or more universal-binding nucleotide.

It will be understood that, regardless of the position at which the one or more universal-binding nucleotide is substituted, the mdRNA or dsRNA molecule is capable of binding to a target gene and one or more variant(s) thereof thereby facilitating the degradation of the target gene or variant thereof via Dicer or a RISC complex. Thus, the mdRNA or dsRNA of the present disclosure are suitable for introduction into cells to mediate targeted post-transcriptional gene silencing of a TNF gene or variants thereof. When a mdRNA or dsRNA is inserted into a cell, the mdRNA or dsRNA duplex is then unwound, and the antisense strand anneals with mRNA to form a Dicer substrate or the antisense strand is loaded into an assembly of proteins to form the RNA-induced silencing complex (RISC).

In yet another embodiment, the mdRNA or dsRNA comprises one or more have a 2'-sugar substitution. Non-limiting examples of a 2'-sugar substitution include 2'-O-methyl, 2'-O-methoxyethyl, 2'-O-2-methoxyethyl, wherein the 2'-sugar substitution is a halogen, or wherein the 2'-sugar substitution is a 2'-fluoro, or wherein the 2'-sugar substitution is a 2'-O-allyl.

In yet another embodiment, the mdRNA or dsRNA comprising at least one, two, three, four, five, or more base pairs (including 6, 7, 8, 9, 10, 11, 12, 13, 14, 15, 16, 17, 18, 19, 20 or more base pairs), each base pair comprising a 5-methyluridine base paired with a 2,6-diaminopurine, and wherein the 5-methyluridine of each base pair is in the guide strand (antisense strand) or wherein the 5-methyluridine of each base pair is in the passenger strand (sense strand).

In any one embodiment of the disclosure, a base pair comprising a 5-methyluridine base paired with a 2,6-diaminopurine in a double-stranded region of the RNA may be as follows:

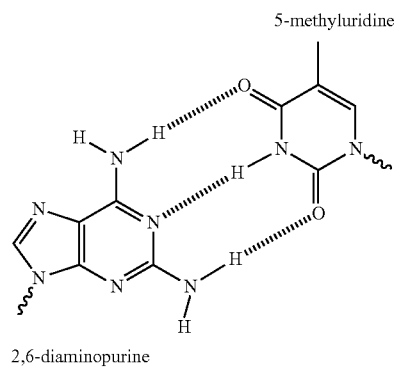

In this schematic, the 5-methyluridne:2,6-diaminopurine base pair has three hydrogen bonds (a hashed line represents a hydrogen bond). The base pair may have 1, 2 or 3 hydrogen bonds, preferably the base pair has 1 hydrogen bond, more preferably two hydrogen bonds and most preferably three hydrogen bonds.

In anyone embodiment of the disclosure, the double-stranded region of an RNA comprises at least one non-standard base pair comprising:

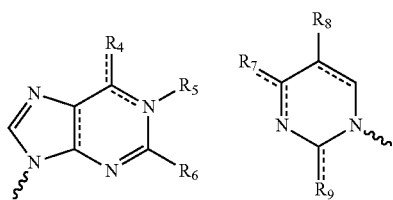

In this schematic, $R_4$, $R_5$, $R_6$, $R_7$, and $R_8$ are independently any one or more organic group consisting of one to twenty (1, 2, 3, 4, 5, 6, 7, 8, 9, 10, 11, 12, 13, 14, 15, 16, 17, 18, 19, or 20) atoms selected from carbon, oxygen, nitrogen, sulfur, hydrogen, selenium, silicon, halogen, chlorine, fluorine, and bromine. A dashed line indicates an optional bond that is either present or absent within the structures above. In this schematic, hydrogen bonds are not indicated in the above structures; however, such hydrogen bonds would form between the hydrogen bond donor and hydrogen bond acceptor groups of $R_4$ and $R_7$, between the hydrogen bond donor group of $R_5$ and the nitrogen (a hydrogen bond acceptor) in the third position of the pyrimidine structure above, and between the hydrogen bond donor and hydrogen bond acceptor group of $R_6$ and $R_9$. In an embodiment of this disclosure, R4 has a hydrogen bond donor group and R7 has a hydrogen bond acceptor group, R5 has a hydrogen bond donor group, and R6 has a hydrogen bond donor group and R9 has an hydrogen bond acceptor group. In another embodiment, R4 has an hydrogen bond acceptor group and R7 has a hydrogen bond donor group, R5 has a hydrogen bond donor group, and R6 has a hydrogen bond donor group and R9 has an hydrogen bond acceptor group. In another embodiment, R4 has an hydrogen bond acceptor group and R7 has a hydrogen bond donor group, R5 has a hydrogen bond donor group, and R6 has an hydrogen bond acceptor group and R9 has a hydrogen bond donor group.

In anyone embodiment of the disclosure, the double-stranded region of an RNA comprises at least one non-standard base pair comprising:

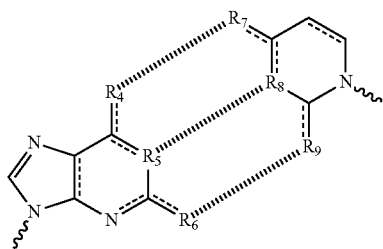

In this schematic, $R_4$, $R_5$, $R_6$, $R_7$, $R_8$, and $R_9$ are independently any one or more organic group consisting of one to twenty (1, 2, 3, 4, 5, 6, 7, 8, 9, 10, 11, 12, 13, 14, 15, 16, 17, 18, 19, or 20) atoms selected from carbon, oxygen, nitrogen, sulfur, hydrogen, selenium, silicon, halogen, chlorine, fluorine, and bromine. A dashed line indicates an optional bond that is either present or absent within the structures above. A hashed line between the substituent groups of the two structures above indicates the presence of a hydrogen bond (three hydrogen bonds are shown in this schematic). In another embodiment, R4 has a donor group and R7 has an acceptor group. In another embodiment, R4 has an acceptor group and R7 has an acceptor group. In another embodiment, R5 has a donor group and R8 has an acceptor group. In another embodiment, R5 has an acceptor group and R8 has an acceptor group. In another embodiment, R6 has a donor group and R9 has an acceptor group. In another embodiment, R6 has an acceptor group and R9 has an acceptor group.

Another aspect of the disclosure is a mdRNA or dsRNA comprising an acyclic nucleotide monomer. In a preferred embodiment, the acyclic nucleotide monomer is a 2'-3'-seco-nucleotide monomer. Preferably, the acyclic nucleotide monomer is selected from the group consisting of monomer E, F, G, H, I or J (see below).

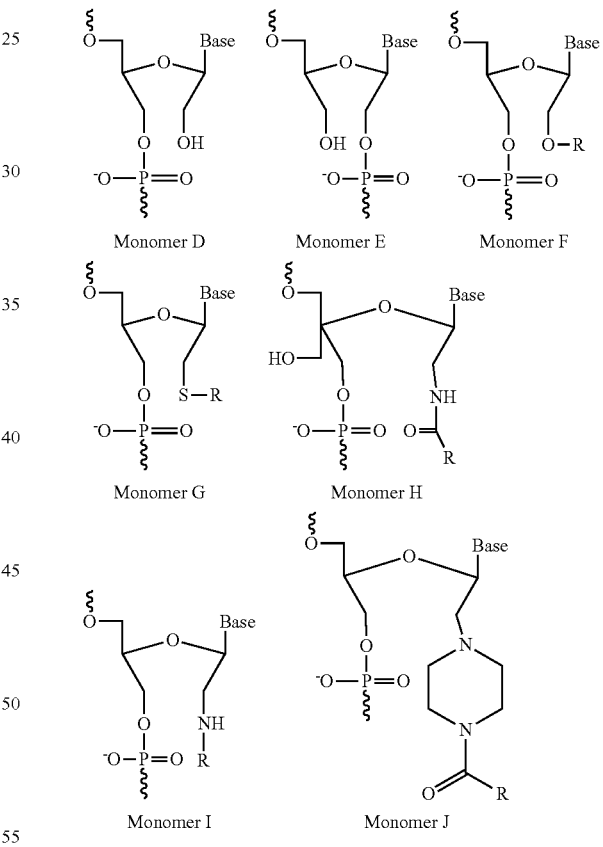

Other examples of acyclic nucleotide monomers are described, for example, in PCT patent application PCT/US2008/64417, hereby incorporated by reference in their entirety.

In addition, as used herein, the term "RNAi" is meant to be equivalent to other terms used to describe sequence specific RNA interference, such as post transcriptional gene silencing, translational inhibition, or epigenetics. For example, dsRNA molecules of this disclosure can be used to epigenetically silence genes at the post-transcriptional level or the pre-transcriptional level or any combination thereof.

In some aspects, this invention provides compositions containing one or more RNAi-inducing agents which are targeted to one or more target transcripts, along with one or more delivery components. Examples of delivery components include lipopeptides, lipids, peptides with attached lipid moieties or attached natural or synthetic polymers, and polymeric lipids.

The compositions and formulations of this invention may be used for delivery of RNAi-inducing entities such as dsRNA, siRNA, mdRNA, miRNA, shRNA, or RNAi-inducing vectors to cells in intact mammalian subjects, and may also be used for delivery of these agents to cells in culture.

This invention also provides methods for the delivery of one or more RNAi-inducing entities to organs and tissues within the body of a mammal. In some embodiments, compositions containing an RNAi-inducing entity and one or more lipopeptide components are introduced by various routes to be transported within the body and taken up by cells in one or more organs or tissues, where expression of a target transcript is modulated.

This invention provides pharmaceutically-acceptable nucleic acid compositions with various lipopeptides, lipids, or peptides having attached lipid moieties or natural or synthetic polymers which are useful for therapeutic delivery of nucleic acids and gene-silencing RNAs. In particular, this invention provides compositions and methods for in vitro and in vivo delivery of dsRNAs for decreasing, downregulating, or silencing the translation of a target nucleic acid sequence or expression of a gene. These compositions and methods may be used for prevention and/or treatment of diseases in a mammal.

In exemplary methods of this invention, a ribonucleic acid molecule such as a dsRNA, siRNA, mdRNA, or shRNA is contacted with a lipopeptide to formulate a composition which can be administered to cells or subjects such as mammals. In some embodiments, this invention provides methods for delivering an interfering-RNA agent such as a dsRNA, siRNA, mdRNA, or shRNA intracellularly by contacting a nucleic acid-containing composition with a cell.

In exemplary embodiments, this invention includes compositions containing a nucleic acid molecule, such as a double-stranded ribonucleic acid (dsRNA), a short interfering RNA (siRNA), a meroduplex RNA (mdRNA), or a short hairpin RNA (shRNA), admixed or complexed with a lipopeptide to form a composition that enhances intracellular delivery of the nucleic acid molecule. In some embodiments, a delivery composition of this invention may contain an interfering-RNA agent and one, two, or more lipopeptides, as well as one or more polymeric lipids.

In certain embodiments, the N/P ratio of the lipopeptide and nucleic acid is from about 0.5 to about 8, from about 1 to about 4, or about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9 or about 4.

The compositions of this invention can form stable particles which may incorporate an interfering RNA agent. Compositions and formulations of this invention may include further delivery-enhancing components or excipients.

In some embodiments, compositions of this invention contain stable RNA-lipid particles having diameters from about 5 nm to about 400 nm. In some embodiments, the particles may have a uniform diameter of from about 10 nm to about 300 nm. In some embodiments, the particles may have a uniform diameter of from about 50 nm to about 150 nm.

Within exemplary compositions of this invention, an interfering-RNA agent may be admixed or complexed with lipopeptides to form a composition that enhances intracellular delivery of the dsRNA as compared to contacting target cells with naked dsRNA.

Lipids for RNA Delivery and Administration

In some aspects of this invention, lipopeptides and additional lipids are employed for delivery and administration of RNA components. More particularly, a composition of this invention may include one or more lipopeptides, which may be cationic, along with other cationic lipids and non-cationic lipids.

Cationic lipids may be monocationic or polycationic. Non-cationic lipids include neutral lipids and lipids having approximately zero net charge at a particular pH, for example, a zwitterionic lipid. Non-cationic lipids also include anionic lipids.

In some embodiments, a composition is a mixture or complex of an RNA component with a lipopeptide and a (non-lipopeptide) cationic lipid. In some embodiments, a composition may be a mixture or complex of one or more interfering RNA agents with one or more lipopeptides and one or more cationic lipids.

Examples of cationic lipids include N-[1-(2,3-dioleoyloxy)propyl]-N,N,N-trimethylammonium chloride (DOTMA); 1,2-bis(oleoyloxy)-3-3-(trimethylammonium) propane (DOTAP), 1,2-bis(dimyristoyloxy)-3-3-(trimethylammonia)propane (DMTAP); 1,2-dimyristoyloxypropyl-3-dimethylhydroxyethylammonium bromide (DMRIE); dimethyldioctadecylammonium bromide (DDAB); 3-(N—(N',N'-dimethylaminoethane)carbamoyl)cholesterol (DC-Chol); 3β-[N',N'-diguanidinoethyl-aminoethane)carbamoyl cholesterol (BGTC); 2-(2-(3-(bis(3-aminopropyl)amino) propylamino)acetamido)-N,N-ditetradecylacetamide (RPR209120); pharmaceutically acceptable salts thereof, and mixtures thereof.

Examples of cationic lipids include 1,2-dialkenoyl-sn-glycero-3-ethylphosphocholines (EPCs), such as 1,2-dioleoyl-sn-glycero-3-ethylphosphocholine, 1,2-distearoyl-sn-glycero-3-ethylphosphocholine, 1,2-dipalmitoyl-sn-glycero-3-ethylphosphocholine, pharmaceutically acceptable salts thereof, and mixtures thereof.

Examples of polycationic lipids include tetramethyltetrapalmitoyl spermine (TMTPS), tetramethyltetraoleyl spermine (TMTOS), tetramethlytetralauryl spermine (TMTLS), tetramethyltetramyristyl spermine (TMTMS), tetramethyldioleyl spermine (TMDOS), pharmaceutically acceptable salts thereof, and mixtures thereof.

Examples of polycationic lipids include 2,5-bis(3-aminopropylamino)-N-(2-(dioctadecylamino)-2-oxoethyl)pentanamide (DOGS); 2,5-bis(3-aminopropylamino)-N-(2-(di (Z)-octadeca-9-dienylamino)-2-oxoethyl)pentanamide (DOGS-9-en); 2,5-bis(3-aminopropylamino)-N-(2-(di(9Z,12Z)-octadeca-9,12-dienylamino)-2-oxoethyl)pentanamide (DLinGS); 3-β($N^4$—$N^1$,$N^8$-dicarbobenzoxyspermidine) carbamoyl)cholesterol (GL-67); (9Z,9'Z)-2-(2,5-bis(3-aminopropylamino)pentanamido)propane-1,3-diyl-dioctadec-9-enoate (DOSPER); 2,3-dioleyloxy-N-[2 (sperminecarboxamido)ethyl]-N,N-dimethyl-1-propanaminium trifluoro-acetate (DOSPA); pharmaceutically acceptable salts thereof, and mixtures thereof.

Examples of cationic lipids include those shown in Table 3.

TABLE 3

Examples of Cationic Lipids

| Compound Name | FA Chains | M.W. | CAS registry # |
| --- | --- | --- | --- |
| DS404-28 BGTC | Cholesterol | 642.96 | 182056-06-0 |
| DOSPER | C18:1 | 848.34 | 178532-92-8 |
| GL-67 | Cholesterol | 615.00 | 179075-30-0 |
| RPR209120 | Myristoyl C14 | 695.16 | 433292-13-8 |
| DOGS | C18:0 | 807.37 | 12050-77-7 |
| DOGS (9-en) | C18:1 | 803.34 | |
| DLinGS | C18:2 | 799.31 | |
| DOTMA | C18:1 | 712.57 | 104162-48-3 |

Examples of cationic lipids are described in U.S. Pat. Nos. 4,897,355; 5,279,833; 6,733,777; 6,376,248; 5,736,392; 5,334,761; 5,459,127; 5,208,036; 5,264,618; 5,283,185; 5,753,613; 5,785,992; and U.S. Patent Publication No. 2005/0064595.

In some embodiments, the composition is a mixture or complex of an RNA component with a lipopeptide and a non-cationic lipid. In some embodiments, the composition is a mixture or complex of one or more RNA components with one or more lipopeptides and one or more non-cationic lipids. Non-cationic lipids include neutral, zwitterionic, and anionic lipids.

In some embodiments, a composition is a mixture or complex of an RNA component with a cationic lipopeptide and a (non-lipopeptide) non-cationic or neutral lipid.

In some embodiments, a composition is a mixture or complex of one or more RNA components with one or more cationic lipopeptides, one or more (non-lipopeptide) cationic lipids, and one or more (non-lipopeptide) non-cationic or neutral lipids.

Examples of non-cationic lipids include 1,2-Dilauroyl-sn-glycerol (DLG); 1,2-Dimyristoyl-sn-glycerol (DMG); 1,2-Dipalmitoyl-sn-glycerol (DPG); 1,2-Distearoyl-sn-glycerol (DSG); 1,2-Dilauroyl-sn-glycero-3-phosphatidic acid (sodium salt; DLPA); 1,2-Dimyristoyl-sn-glycero-3-phosphatidic acid (sodium salt; DMPA); 1,2-Dipalmitoyl-sn-glycero-3-phosphatidic acid (sodium salt; DPPA); 1,2-Distearoyl-sn-glycero-3-phosphatidic acid (sodium salt; DSPA); 1,2-Diarachidoyl-sn-glycero-3-phosphocholine (DAPC); 1,2-Dilauroyl-sn-glycero-3-phosphocholine (DLPC); 1,2-Dimyristoyl-sn-glycero-3-phosphocholine (DMPC); 1,2-Dipalmitoyl-sn-glycero-0-ethyl-3-phosphocholine (chloride or triflate; DPePC); 1,2-Dipalmitoyl-sn-glycero-3-phosphocholine (DPPC); 1,2-Distearoyl-sn-glycero-3-phosphocholine (DSPC); 1,2-Dilauroyl-sn-glycero-3-phosphoethanolamine (DLPE); 1,2-Dimyristoyl-sn-glycero-3-phosphoethanolamine (DMPE); 1,2-Dipalmitoyl-sn-glycero-3-phosphoethanolamine (DPPE); 1,2-Distearoyl-sn-glycero-3-phosphoethanolamine (DSPE); 1,2-Dilauroyl-sn-glycero-3-phosphoglycerol (sodium salt; DLPG); 1,2-Dimyristoyl-sn-glycero-3-phosphoglycerol (sodium salt; DMPG); 1,2-Dimyristoyl-sn-glycero-3-phospho-sn-1-glycerol (ammonium salt; DMP-sn-1-G); 1,2-Dipalmitoyl-sn-glycero-3-phosphoglycerol (sodium salt; DPPG); 1,2-Distearoyl-sn-glycero-3-phosphoglycero (sodium salt; DSPG); 1,2-Distearoyl-sn-glycero-3-phospho-sn-1-glycerol (sodium salt; DSP-sn-1-G); 1,2-Dipalmitoyl-sn-glycero-3-phospho-L-serine (sodium salt; DPPS); 1-Palmitoyl-2-linoleoyl-sn-glycero-3-phosphocholine (PLinoPC); 1-Palmitoyl-2-oleoyl-sn-glycero-3-phosphocholine (POPC); 1-Palmitoyl-2-oleoyl-sn-glycero-3-phosphoglycerol (sodium salt; POPG); 1-Palmitoyl-2-oleoyl-sn-glycero-3-phosphoglycerol (sodium salt; POPG); 1-Palmitoyl-2-oleoyl-sn-glycero-3-phosphoglycerol (ammonium salt; POPG); 1-Palmitoyl-2-4o-sn-glycero-3-phosphocholine (P-lyso-PC); 1-Stearoyl-2-lyso-sn-glycero-3-phosphocholine (S-lyso-PC); and mixtures thereof.

Examples of non-cationic lipids include polymeric compounds and polymer-lipid conjugates or polymeric lipids, such as pegylated lipids having PEG regions of 300, 500, 1000, 1500, 2000, 3500, 5000, or 10,000 molecular weight, including polyethyleneglycols, N-(Carbonyl-methoxypolyethyleneglycol-2000)-1,2-dimyristoyl-sn-glycero-3-phosphoethanolamine (sodium salt; DMPE-MPEG-2000); N-(Carbonyl-methoxypolyethyleneglycol-5000)-1,2-dimyristoyl-sn-glycero-3-phosphoethanolamine (sodium salt; DMPE-MPEG-5000); N-(Carbonyl-methoxypolyethyleneglycol 2000)-1,2-dipalmitoyl-sn-glycero-3-phosphoethanolamine (sodium salt; DPPE-MPEG-2000); N-(Carbonyl-methoxypolyethyleneglycol 5000)-1,2-dipalmitoyl-sn-glycero-3-phosphoethanolamine (sodium salt; DPPE-MPEG-5000); N-(Carbonyl-methoxypolyethyleneglycol 750)-1,2-distearoyl-sn-glycero-3-phosphoethanolamine (sodium salt; DSPE-MPEG-750); N-(Carbonyl-methoxypolyethyleneglycol 2000)-1,2-distearoyl-sn-glycero-3-phosphoethanolamine (sodium salt; DSPE-MPEG-2000); N-(Carbonyl-methoxypolyethyleneglycol 5000)-1,2-distearoyl-sn-glycero-3-phosphoethanolamine (sodium salt; DSPE-MPEG-5000); sodium cholesteryl sulfate (SCS); pharmaceutically acceptable salts thereof, and mixtures thereof.

Examples of non-cationic lipids include polymeric lipids such as DOPE-PEG, DLPE-PEG, DDPE-PEG DLinPE-PEG, and diacylglycerol-PEG-2000, -5000 or -10,000.

Examples of non-cationic lipids include polymeric lipids such as multi-branched pegylated compounds, for example DSPE-PTE020 and DSPE-AM0530K.

Examples of non-cationic lipids include polymeric lipids such as DSPE-PG8G polyglycerine lipids.

Examples of non-cationic lipids include dioleoylphosphatidylethanolamine (DOPE), didecanoylphosphatidylcholine (DDPC), diphytanoylphosphatidylethanolamine (DPhPE), 1,2-Dioleoyl-sn-Glycero-3-Phosphocholine (DOPC), and 1,2-Diphytanoyl-sn-Glycero-3-Phosphocholine (DPhPC).

Examples of non-cationic lipids include cholesterols, sterols, and steroids such as gonanes, estranes, androstanes, pregnanes, cholanes, cholestanes, ergostanes, campestanes, poriferastanes, stigmastanes, gorgostanes, lanostanes, cycloartanes, as well as sterol or zoosterol derivatives of any of the foregoing, and their biological intermediates and precursors, which may include, for example, cholesterol, lanosterol, stigmastanol, dihydrolanosterol, zymosterol, zymostenol, desmosterol, 7-dehydrocholesterol, and mixtures and derivatives thereof.

Examples of non-cationic lipids include pegylated cholesterols, and cholestane 3-oxo(C1-22acyl) derivatives such as cholesteryl acetate, cholesteryl arachidonate, cholesteryl butyrate, cholesteryl hexanoate, cholesteryl caprylate, cholesteryl n-decanoate, cholesteryl dodecanoate, cholesteryl myristate, cholesteryl palmitate, cholesteryl behenate, cholesteryl stearate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, cholesteryl linoleate, and mixtures and derivatives thereof.

Examples of non-cationic lipids include compounds derived from plant sterols including phytosterols, beta-sitosterol, campesterol, ergosterol, brassicasterol, delta-7-stigmasterol, delta-7-avenasterol, and mixtures and derivatives thereof.

Examples of non-cationic lipids include bile acids, cholic acid, chenodeoxycholic acid, glycocholic acid, taurocholic acid, deoxycholic acid, lithocholic acid, methyl-lithocholic acid, and mixtures and derivatives thereof.

Examples of non-cationic lipids include compounds derived from steroids including glucocorticoids, cortisol, hydrocortisone, corticosterone, $\Delta^5$-pregnenolone, progesterone, deoxycorticosterone, 17-OH-pregnenolone, 17-OH-progesterone, 11-dioxycortisol, dehydroepiandrosterone, dehydroepiandrosterone sulfate, androstenedione, aldosterone, 18-hydroxycorticosterone, tetrahydrocortisol, tetrahydrocortisone, cortisone, prednisone, 6α-methylpredisone, 9α-fluoro-16α-hydroxyprednisolone, 9α-fluoro-16α-methylprednisolone, 9α-fluorocortisol, and mixtures and derivatives thereof.

Examples of non-cationic lipids include compounds derived from steroids including androgens, testosterone, dihydrotestosterone, androstenediol, androstenedione, androstenedione, 3α,5α-androstanediol, and mixtures and derivatives thereof.

Examples of non-cationic lipids include compounds derived from steroids including estrogens, estriols, estrones, estradiols, and mixtures and derivatives thereof.

Examples of non-cationic lipids include compounds derived from lumisterol and vitamin D compounds.

Examples of non-cationic lipids include lipids ranging from C10:0 to C22:6 phosphoethanolamine as shown in Table 4.

TABLE 4

Examples of Non-cationic Lipids

| Name | FA chains | M.W. | CAS Registry # |
|---|---|---|---|
| DDPE | C10:0 | 523.64 | 253685-27-7 |
| DLPE | C12:0 | 579.76 | 59752-57-7 |
| DSPE | C18:0 | 748.08 | 1069-79-0 |
| DOPE | C18:1 | 744.05 | 4004-05-1 |
| DLinPE | C18:2 | 740.01 | 20707-71-5 |
| DLenPE | C18:3 | 735.98 | 34813-40-6 |
| DARAPE | C20:4 | 788.06 | 5634-86-6 |
| DDHAPE | C22:6 | 836.10 | 123284-81-1 |
| DPhPE | 16:0[(CH3)4] | 804.19 | 201036-16-0 |

Examples of anionic lipids include phosphatidylserine, phosphatidic acid, phosphatidylcholine, platelet-activation factor (PAF), phosphatidylethanolamine, phosphatidyl-DL-glycerol, phosphatidylinositol, phosphatidylinositol (pi(4)p, pi(4,5)p2), cardiolipin (sodium salt), lysophosphatides, hydrogenated phospholipids, sphingoplipids, gangliosides, phytosphingosine, sphinganines, pharmaceutically acceptable salts thereof, and mixtures thereof.

In certain aspects, the lipopeptide is about from 10% to about 100% mole percentage of delivery components, not including the nucleic acid (e.g., RNA). In other embodiments, the lipopeptide is from about 20% to about 80%, or from about 30% to about 70%, or from about 40% to about 60% mole percentage of delivery components, or about 20%, 30%, 35%, 40%, 45%, 50%, 55%, 60%, 65%, 70%, 75%, 80%, 85%, 90%, or 95% mole percentage of delivery components.

Additional Delivery Lipids

In some aspects of this invention, amino acid lipids and additional non-amino acid lipids may be employed for delivery and administration of regulatory RNA components, RNA antagonists, interfering RNA, or nucleic acids. More particularly, a composition of this invention may include one or more amino acid lipids along with non-amino acid cationic lipids and non-amino acid non-cationic lipids.

Non-amino acid cationic lipids may be monocationic or polycationic. Some non-amino acid cationic lipids include neutral lipids and lipids having approximately zero net charge at a particular pH, for example, a zwitterionic lipid. Non-amino acid non-cationic lipids also include anionic lipids.

In some embodiments, a composition is a mixture or complex of an RNA component with an amino acid lipid and a non-amino acid cationic lipid. In some embodiments, a composition may be a mixture or complex of one or more regulatory or interfering RNA agents with one or more amino acid lipids and one or more non-amino acid cationic lipids.

The compounds and compositions of this disclosure can be admixed with, or attached to various targeting ligands or agents to deliver an active agent to a cell, tissue, organ or region of an organism. Examples of targeting agents include antibodies, ligands for receptors, peptides, proteins, lectins, (poly)saccharides, galactose, mannose, cyclodextrins, nucleic acids, DNA, RNA, aptamers, and polyamino acids.

Examples of non-amino acid cationic lipids include N-[1-(2,3-dioleoyloxy)propyl]-N,N,N-trimethylammonium chloride (DOTMA); 1,2-bis(oleoyloxy)-3-3-(trimethylammonium)propane (DOTAP), 1,2-bis(dimyristoyloxy)-3-3-(trimethylammonia)propane (DMTAP); 1,2-dimyristoyloxypropyl-3-dimethylhydroxyethylammonium bromide (DMRIE); dimethyldioctadecylammonium bromide (DDAB); 3-(N—(N',N'-dimethylaminoethane)carbamoyl)cholesterol (DC-Chol); 3β-[N',N'-diguanidinoethyl-aminoethane)carbamoyl cholesterol (BGTC); 2-(2-(3-(bis(3-aminopropyl)amino)propylamino)acetamido)-N,N-ditetradecylacetamide (RPR209120); pharmaceutically acceptable salts thereof, and mixtures thereof.

Examples of non-amino acid cationic lipids include 1,2-dialkenoyl-sn-glycero-3-ethylphosphocholines (EPCs), such as 1,2-dioleoyl-sn-glycero-3-ethylphosphocholine, 1,2-distearoyl-sn-glycero-3-ethylphosphocholine, 1,2-dipalmitoyl-sn-glycero-3-ethylphosphocholine, pharmaceutically acceptable salts thereof, and mixtures thereof.

Examples of non-amino acid cationic lipids include 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), and 1,2-dilinolenyloxy-N,N-dimethyl-3-aminopropane (DLenDMA).

Examples of non-amino acid polycationic lipids include tetramethyltetrapalmitoyl spermine (TMTPS), tetramethyltetraoleyl spermine (TMTOS), tetramethyltetralauryl spermine (TMTLS), tetramethyltetramyristyl spermine (TMTMS), tetramethyldioleyl spermine (TMDOS), pharmaceutically acceptable salts thereof, and mixtures thereof.

Examples of non-amino acid polycationic lipids include 2,5-bis(3-aminopropylamino)-N-(2-(dioctadecylamino)-2-oxoethyl)pentanamide (DOGS); 2,5-bis(3-aminopropylamino)-N-(2-(di(Z)-octadeca-9-dienylamino)-2-oxoethyl) pentanamide (DOGS-9-en); 2,5-bis(3-aminopropylamino)-N-(2-(di(9Z,12Z)-octadeca-9,12-dienylamino)-2-oxoethyl) pentanamide (DLinGS); 3-beta-($N^4$—($N^1,N^8$-dicarbobenzoxyspermidine)carbamoyl)cholesterol (GL-67); (9Z,9'Z)-2-(2,5-bis(3-aminopropylamino)pentanamido)propane-1,3-diyl-dioctadec-9-enoate (DOSPER); 2,3-dioleyloxy-N-[2(sperminecarboxamido)ethyl]-N,N-dimethyl-1-propanaminium trifluoro-acetate (DOSPA); pharmaceutically acceptable salts thereof, and mixtures thereof.

Examples of non-amino acid cationic lipids include DS404-28 BGTC (CAS 182056-06-0), DOSPER (CAS 178532-92-8), GL-67 (179075-30-0), RPR209120 (CAS 433292-13-8), DOGS (12050-77-7), DOGS (9-en, C18:1), DLinGS (C18:2), and DOTMA (104162-48-3).

Examples of non-amino acid cationic lipids are described in U.S. Pat. Nos. 4,897,355; 5,279,833; 6,733,777; 6,376,248; 5,736,392; 5,334,761; 5,459,127; 2005/0064595; 5,208,036; 5,264,618; 5,279,833; 5,283,185; 5,753,613; and 5,785,992.

In some embodiments, the composition is a mixture or complex of an RNA component with an amino acid lipid and a non-amino acid non-cationic lipid. In some embodiments, the composition is a mixture or complex of one or more RNA components with one or more amino acid lipids and one or more non-amino acid non-cationic lipids.

Non-amino acid non-cationic lipids include neutral, zwitterionic, and anionic lipids. Thus, a non-cationic zwitterionic lipid may contain a cationic head group.

Examples of non-amino acid non-cationic lipids include 1,2-Dilauroyl-sn-glycerol (DLG); 1,2-Dimyristoyl-sn-glycerol (DMG); 1,2-Dipalmitoyl-sn-glycerol (DPG); 1,2-Distearoyl-sn-glycerol (DSG); 1,2-Dilauroyl-sn-glycero-3-phosphatidic acid (sodium salt; DLPA); 1,2-Dimyristoyl-sn-glycero-3-phosphatidic acid (sodium salt; DMPA); 1,2-Dipalmitoyl-sn-glycero-3-phosphatidic acid (sodium salt; DPPA); 1,2-Distearoyl-sn-glycero-3-phosphatidic acid (sodium salt; DSPA); 1,2-Diarachidoyl-sn-glycero-3-phosphocholine (DAPC); 1,2-Dilauroyl-sn-glycero-3-phosphocholine (DLPC); 1,2-Dimyristoyl-sn-glycero-3-phosphocholine (DMPC); 1,2-Dipalmitoyl-sn-glycero-0-ethyl-3-phosphocholine (chloride or triflate; DPePC); 1,2-Dipalmitoyl-sn-glycero-3-phosphocholine (DPPC); 1,2-Distearoyl-sn-glycero-3-phosphocholine (DSPC); 1,2-Dilauroyl-sn-glycero-3-phosphoethanolamine (DLPE); 1,2-Dimyristoyl-sn-glycero-3-phosphoethanolamine (DMPE); 1,2-Dipalmitoyl-sn-glycero-3-phosphoethanolamine (DPPE); 1,2-Distearoyl-sn-glycero-3-phosphoethanolamine (DSPE); 1,2-Dilauroyl-sn-glycero-3-phosphoglycerol (sodium salt; DLPG); 1,2-Dimyristoyl-sn-glycero-3-phosphoglycerol (sodium salt; DMPG); 1,2-Dimyristoyl-sn-glycero-3-phospho-sn-1-glycerol (ammonium salt; DMP-sn-1-G); 1,2-Dipalmitoyl-sn-glycero-3-phosphoglycerol (sodium salt; DPPG); 1,2-Distearoyl-sn-glycero-3-phosphoglycero (sodium salt; DSPG); 1,2-Distearoyl-sn-glycero-3-phospho-sn-1-glycerol (sodium salt; DSP-sn-1-G); 1,2-Dipalmitoyl-sn-glycero-3-phospho-L-serine (sodium salt; DPPS); 1-Palmitoyl-2-linoleoyl-sn-glycero-3-phosphocholine (PLinoPC); 1-Palmitoyl-2-oleoyl-sn-glycero-3-phosphocholine (POPC); 1-Palmitoyl-2-oleoyl-sn-glycero-3-phosphoglycerol (sodium salt; POPG); 1-Palmitoyl-2-oleoyl-sn-glycero-3-phosphoglycerol (sodium salt; POPG); 1-Palmitoyl-2-oleoyl-sn-glycero-3-phosphoglycerol (ammonium salt; POPG); 1-Palmitoyl-2-4o-sn-glycero-3-phosphocholine (P-lyso-PC); 1-Stearoyl-2-lyso-sn-glycero-3-phosphocholine (S-lyso-PC); and mixtures thereof.

Examples of non-amino acid non-cationic lipids include polymeric compounds and polymer-lipid conjugates or polymeric lipids, such as pegylated lipids having PEG regions of 300, 500, 1000, 1500, 2000, 3500, or 5000 molecular weight, including polyethyleneglycols, N-(Carbonyl-methoxypolyethyleneglycol-2000)-1,2-dimyristoyl-sn-glycero-3-phosphoethanolamine (sodium salt; DMPE-MPEG-2000); N-(Carbonyl-methoxypolyethyleneglycol-5000)-1,2-dimyristoyl-sn-glycero-3-phosphoethanolamine (sodium salt; DMPE-MPEG-5000); N-(Carbonyl-methoxypolyethyleneglycol 2000)-1,2-dipalmitoyl-sn-glycero-3-phosphoethanolamine (sodium salt; DPPE-MPEG-2000); N-(Carbonyl-methoxypolyethyleneglycol 5000)-1,2-dipalmitoyl-sn-glycero-3-phosphoethanolamine (sodium salt; DPPE-MPEG-5000); N-(Carbonyl-methoxypolyethyleneglycol 750)-1,2-distearoyl-sn-glycero-3-phosphoethanolamine (sodium salt; DSPE-MPEG-750); N-(Carbonyl-methoxypolyethyleneglycol 2000)-1,2-distearoyl-sn-glycero-3-phosphoethanolamine (sodium salt; DSPE-MPEG-2000); N-(Carbonyl-methoxypolyethyleneglycol 5000)-1,2-distearoyl-sn-glycero-3-phosphoethanolamine (sodium salt; DSPE-MPEG-5000); sodium cholesteryl sulfate (SCS); pharmaceutically acceptable salts thereof, and mixtures thereof.

Examples of non-amino acid non-cationic lipids include polymeric lipids such as DOPE-PEG, DLPE-PEG, DDPE-PEG DLinPE-PEG, and diacylglycerol-PEG-2000 or -5000.

Examples of non-amino acid non-cationic lipids include polymeric lipids such as multi-branched pegylated compounds, for example DSPE-PTE020 and DSPE-AM0530K.

Examples of non-amino acid non-cationic lipids include polymeric lipids such as DSPE-PG8G polyglycerine lipids.

Examples of non-amino acid non-cationic lipids include dioleoylphosphatidylethanolamine (DOPE), diphytanoylphosphatidylethanolamine (DPhPE), 1,2-Dioleoyl-sn-Glycero-3-Phosphocholine (DOPC), and 1,2-Diphytanoyl-sn-Glycero-3-Phosphocholine (DPhPC).

Examples of non-amino acid non-cationic lipids include cholesterols, sterols, and steroids such as gonanes, estranes, androstanes, pregnanes, cholanes, cholestanes, ergostanes, campestanes, poriferastanes, stigmastanes, gorgostanes, lanostanes, cycloartanes, as well as sterol or zoosterol derivatives of any of the foregoing, and their biological intermediates and precursors, which may include, for example, cholesterol, lanosterol, stigmastanol, dihydrolanosterol, zymosterol, zymostenol, desmosterol, 7-dehydrocholesterol, and mixtures and derivatives thereof.

Examples of non-amino acid non-cationic lipids include pegylated cholesterols, and cholestane 3-oxo(C1-22acyl) derivatives such as cholesteryl acetate, cholesteryl arachidonate, cholesteryl butyrate, cholesteryl hexanoate, cholesteryl caprylate, cholesteryl n-decanoate, cholesteryl dodecanoate, cholesteryl myristate, cholesteryl palmitate, cholesteryl behenate, cholesteryl stearate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, cholesteryl linoleate, and mixtures and derivatives thereof.

Examples of non-amino acid non-cationic lipids include compounds derived from plant sterols including phytosterols, beta-sitosterol, campesterol, ergosterol, brassicasterol, delta-7-stigmasterol, delta-7-avenasterol, and mixtures and derivatives thereof.

Examples of non-amino acid non-cationic lipids include bile acids, cholic acid, chenodeoxycholic acid, glycocholic acid, taurocholic acid, deoxycholic acid, lithocholic acid, methyl-lithocholic acid, and mixtures and derivatives thereof.

Examples of non-amino acid non-cationic lipids include compounds derived from steroids including glucocorticoids, cortisol, hydrocortisone, corticosterone, $\Delta^5$-pregnenolone, progesterone, deoxycorticosterone, 17-OH-pregnenolone, 17-OH-progesterone, 11-dioxycortisol, dehydroepiandrosterone, dehydroepiandrosterone sulfate, androstenedione, aldosterone, 18-hydroxycorticosterone, tetrahydrocortisol, tetrahydrocortisone, cortisone, prednisone, 6α-methylpredisone, 9α-fluoro-16α-hydroxyprednisolone, 9α-fluoro-16α-methylprednisolone, 9α-fluorocortisol, and mixtures and derivatives thereof.

Examples of non-amino acid non-cationic lipids include compounds derived from steroids including androgens, testosterone, dihydrotestosterone, androstenediol, androstenedione, androstenedione, 3α,5α-androstanediol, and mixtures and derivatives thereof.

Examples of non-amino acid non-cationic lipids include compounds derived from steroids including estrogens, estriols, estrones, estradiols, and mixtures and derivatives thereof.

Examples of non-amino acid non-cationic lipids include compounds derived from lumisterol and vitamin D compounds.

Examples of non-amino acid non-cationic lipids include lipids having tails ranging from C10:0 to C22:6, for example, DDPE (C10:0) (CAS 253685-27-7), DLPE (C12:0) (CAS 59752-57-7), DSPE (C18:0) (CAS 1069-79-0), DOPE (C18:1) (CAS 4004-05-1), DLinPE (C18:2) (CAS 20707-71-5), DLenPE (C18:3) (CAS 34813-40-6), DARAPE (C20:4) (CAS 5634-86-6), DDHAPE (C22:6) (CAS 123284-81-1), DPhPE (16:0[(CH$_3$)$_4$]) (CAS 201036-16-0).

Examples of non-amino acid anionic lipids include phosphatidylserine, phosphatidic acid, phosphatidylcholine, platelet-activation factor (PAF), phosphatidylethanolamine, phosphatidyl-DL-glycerol, phosphatidylinositol, phosphatidylinositol (pi(4)p, pi(4,5)p2), cardiolipin (sodium salt), lysophosphatides, hydrogenated phospholipids, sphingolipids, gangliosides, phytosphingosine, sphinganines, pharmaceutically acceptable salts thereof, and mixtures thereof.

Compositions and Formulations for Administration

The nucleic acid compositions and formulations of this invention may be administered by various routes, for example, to effect systemic delivery via intravenous, parenteral, or intraperitoneal routes. In some embodiments, an siRNA may be delivered intracellularly, for example, in cells of a target tissue such as lung or liver, or in inflamed tissues. Included within this disclosure are compositions and methods for delivery of an siRNA agent by removing cells of a subject, delivering an siRNA agent to the removed cells, and reintroducing the cells into a subject. In some embodiments, this invention provides a method for delivery of siRNA in vivo. A nucleic acid composition may be administered intravenously, subcutaneously, or intraperitoneally to a subject. In some embodiments, the invention provides methods for in vivo delivery of interfering RNA to the lung of a mammalian subject.

In some embodiments, this invention provides a method of treating a disease or disorder in a mammalian subject. A therapeutically effective amount of a composition of this invention containing an interfering RNA, a lipopeptide, and optionally a non-cationic lipid, a polymeric lipid, and one or more delivery-enhancing components or excipients may be administered to a subject having a disease or disorder associated with expression or overexpression of a gene that can be reduced, decreased, downregulated, or silenced by the composition.

This invention encompasses methods for treating a disease of the lung such as respiratory distress, asthma, cystic fibrosis, pulmonary fibrosis, chronic obstructive pulmonary disease, bronchitis, or emphysema, by administering to the subject a therapeutically effective amount of a composition.

This invention encompasses methods for treating rheumatoid arthritis, liver disease, encephalitis, bone fracture, heart disease, viral disease including hepatitis and influenza, or cancer.

Compositions and formulations of this disclosure may be used for delivery of drug agents or biologically active agents to a variety of cells in vitro. Examples of cells for which in vitro delivery is encompassed include epithelial cells such as A549, immortal cell lines such as HeLa, hepatoma cells such as HepG2, rat gliosarcoma cells such as 9L/LacZ, human monocyte cells such as THP-1, Madin-Darby canine kidney cells (MDCK), various fibroblast cell lines, and primary cells in culture in the presence or absence of various sera, among others.

Compositions and formulations of this disclosure may be used for delivery of drug agents or biologically active agents to a variety of cells, tissues or organs in vivo. Modalities for delivering an agent in vivo include topical, enteral, and parenteral routes. Examples of modalities for delivering an agent in vivo include inhalation of particles or droplets, delivery of nasal or nasal-pharngyl drops, particles, or suspensions, transdermal and transmucosal routes, as well as injection or infusion by intramuscular, subcutaneous, intravenous, intraarterial, intracardiac, intrathecal, intraosseus, intraperitoneal, and epidural routes.

In some embodiments, an agent can be administered ex vivo by direct exposure to cells, tissues or organs originating from a mammalian subject.

A drug agent or biologically active agent to be delivered using a composition or formulation of this disclosure may be found in any form including, for example, a pure form, a crystalline form, a solid form, a nanoparticle, a condensed form, a complexed form, or a conjugated form.

This invention also provides methods for the delivery of one or more RNAi-inducing entities to organs and tissues within the body of a mammal. In some embodiments, compositions containing an RNAi-inducing entity, one or more amino acid lipids, and one or more additional lipid components are introduced by various routes to be transported within the body and taken up by cells in one or more organs or tissues, where expression of a target transcript is modulated.

Ribonucleic acid agents useful for this invention may be targeted to various genes. Examples of human genes suitable as targets include TNF, PLK1, BIRC5, APOB, FLT1, the VEGF family, the ERBB family, the PDGFR family, BCR-ABL, and the MAPK family, among others. Examples of human genes suitable as targets and nucleic acid sequences thereto include those disclosed in PCT/US08/55333, PCT/US08/55339, PCT/US08/55340, PCT/US08/55341, PCT/US08/55350, PCT/US08/55353, PCT/US08/55356, PCT/US08/55357, PCT/US08/55360, PCT/US08/55362, PCT/US08/55365, PCT/US08/55366, PCT/US08/55369, PCT/US08/55370, PCT/US08/55371, PCT/US08/55372, PCT/US08/55373, PCT/US08/55374, PCT/US08/55375, PCT/US08/55376, PCT/US08/55377, PCT/US08/55378, PCT/US08/55380, PCT/US08/55381, PCT/US08/55382, PCT/US08/55383, PCT/US08/55385, PCT/US08/55386, PCT/US08/55505, PCT/US08/55511, PCT/US08/55515, PCT/US08/55516, PCT/US08/55519, PCT/US08/55524, PCT/US08/55526, PCT/US08/55527, PCT/US08/55532, PCT/US08/55533, PCT/US08/55542, PCT/US08/55548, PCT/US08/55550, PCT/US08/55551, PCT/US08/55554, PCT/US08/55556, PCT/US08/55560, PCT/US08/55563, PCT/US08/55597, PCT/US08/55599, PCT/US08/55601, PCT/US08/55603, PCT/US08/55604, PCT/US08/55606, PCT/US08/55608, PCT/US08/55611, PCT/US08/55612, PCT/

US08/55615, PCT/US08/55618, PCT/US08/55622, PCT/US08/55625, PCT/US08/55627, PCT/US08/55631, PCT/US08/55635, PCT/US08/55644, PCT/US08/55649, PCT/US08/55651, PCT/US08/55662, PCT/US08/55672, PCT/US08/55676, PCT/US08/55678, PCT/US08/55695, PCT/US08/55697, PCT/US08/55698, PCT/US08/55701, PCT/US08/55704, PCT/US08/55708, PCT/US08/55709, PCT/US08/55711, U.S. Patent Application No. 61/086,435, and U.S. Patent Application No. 61/086,445.

The compositions and methods of the invention may be administered to subjects by a variety of mucosal administration modes, including by oral, rectal, vaginal, intranasal, intrapulmonary, or transdermal delivery, or by topical delivery to the eyes, ears, skin or other mucosal surfaces. In some aspects of this invention, the mucosal tissue layer includes an epithelial cell layer. The epithelial cell can be pulmonary, tracheal, bronchial, alveolar, nasal, buccal, epidermal, or gastrointestinal. Compositions of this invention can be administered using conventional actuators such as mechanical spray devices, as well as pressurized, electrically activated, or other types of actuators.

Compositions of this invention may be administered in an aqueous solution as a nasal or pulmonary spray and may be dispensed in spray form by a variety of methods known to those skilled in the art. Pulmonary delivery of a composition of this invention may be achieved by administering the composition in the form of drops, particles, or spray, which can be, for example, aerosolized, atomized, or nebulized. Pulmonary delivery may be performed by administering the composition in the form of drops, particles, or spray, via the nasal or bronchial passages. Particles of the composition, spray, or aerosol can be in a either liquid or solid form. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering said solution sterile. The formulations may be presented in multi-dose containers, for example in the sealed dispensing system disclosed in U.S. Pat. No. 4,511,069. Other suitable nasal spray delivery systems have been described in *Transdermal Systemic Medication*, Y. W. Chien ed., Elsevier Publishers, New York, 1985; and in U.S. Pat. No. 4,778,810. Additional aerosol delivery forms may include, for example, compressed air-, jet-, ultrasonic-, and piezoelectric nebulizers, which deliver the biologically active agent dissolved or suspended in a pharmaceutical solvent, for example, water, ethanol, or mixtures thereof.

Nasal and pulmonary spray solutions of the present invention typically comprise the drug or drug to be delivered, optionally formulated with a surface active agent, such as a nonionic surfactant (e.g., polysorbate-80), and one or more buffers. In some embodiments of the present invention, the nasal spray solution further comprises a propellant. The pH of the nasal spray solution may be from about pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, this invention is a pharmaceutical product which includes a solution containing a composition of this invention and an actuator for a pulmonary, mucosal, or intranasal spray or aerosol.

A dosage form of the composition of this invention can be liquid, in the form of droplets or an emulsion, or in the form of an aerosol.

A dosage form of the composition of this invention can be solid, which can be reconstituted in a liquid prior to administration. The solid can be administered as a powder. The solid can be in the form of a capsule, tablet or gel.

To formulate compositions for pulmonary delivery within the present invention, the biologically active agent can be combined with various pharmaceutically acceptable additives or delivery-enhancing components, as well as a base or carrier for dispersion of the active agent(s). Examples of additives or delivery-enhancing components include pH control agents such as arginine, sodium hydroxide, glycine, hydrochloric acid, citric acid, and mixtures thereof. Other additives or delivery-enhancing components include local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of about ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl (meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. A biodegradable polymer may be selected as a base or carrier, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, cross-linking and the like. The carrier can be provided in a variety of forms, including, fluid or viscous solutions, gels, pastes, powders, microspheres and films for direct application to the nasal mucosa. The use of a selected carrier in this context may result in promotion of absorption of the biologically active agent.

The biologically active agent can be combined with the base or carrier according to a variety of methods, and release of the active agent may be by diffusion, disintegration of the carrier, or associated formulation of water channels. In some circumstances, the active agent is dispersed in microcapsules (microspheres) or nanocapsules (nanospheres) prepared from a suitable polymer, for example, isobutyl 2-cyanoacrylate (see, e.g., Michael, et al., *J. Pharmacy Pharmacol.* 43:1-5, 1991), and dispersed in a biocompatible dispersing medium applied to the nasal mucosa, which yields sustained delivery and biological activity over a protracted time.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3,000. Examples of hydrophilic low molecular weight compounds include polyol compounds, such as oligo-, di- and monosaccarides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this invention may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the invention, the biologically active agent may be administered in a time release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the invention can be brought about by including in the composition agents that delay absorption, for example, aluminum monosterate hydrogels and gelatin.

Within certain embodiments of this invention, the siNA composition may contain one or more natural or synthetic surfactants. Certain natural surfactants are found in human lung (pulmonary surfactant), and are a complex mixture of phospholipids and proteins that form a monolayer at the alveolar air-liquid interface and reduces surface tension to near zero at expiration and prevents alveolar collapse. Over 90% (by weight) of pulmonary surfactant is composed of phospholipids with approximately 40-80% being DPPC and the remainder being unsaturated phosphatidylcholines POPG, POPC and phosphatidylglycerols. The remaining 10% (by weight) of surfactant is composed of plasma proteins and apoproteins, such as surface proteins (SP)-A, SP-B, SP-C and SP-D.

Examples of natural surfactants that may be used in this invention include SURVANTA™ (beractant), CUROSURF™ (poractant alfa) and INFASURF™ (calfactant), and mixtures thereof.

Examples of synthetic surfactants include sinapultide; a combination of dipalmitoylphosphatidylcholine, palmitoyloleoyl phosphatidylglycerol and palmitic acid; SUR-FAXIN™ (lucinactant); and EXOSURF™ (colfosceril); components which may contain tyloxapol, DPPC, and hexadecanol; and mixtures thereof.

Compositions of this invention can be prepared by methods known in the art. Methods of making the lipid compositions include ethanol injection methods and extrusion methods using a Northern Lipids Lipex Extruder system with stacked polycarbonate membrane filters of defined pore size. Sonication using probe tip and bath sonicators can be employed to produce lipid particles of uniform size. Homogenous and monodisperse particle sizes can be obtained without the addition of the nucleic acid component. For in vitro transfection compositions, the nucleic acid component can be added after the transfection agent is made and stabilized by additional buffer components. For in vivo delivery compositions, the nucleic acid component is part of the formulation.

A mixing procedure involving the graded substitution of ethanol for buffer can be used to create a narrow homodisperse particle size distribution. The lipid components and lipopeptides can be dissolved in USP absolute ethanol and the RNA component can be dissolved in an aqueous buffer, for example, at 0.9 mg/mL. Both mixtures can be injected through an HPLC mixing tee into a 20 mM citrate buffer at pH 7.2. The initial concentration of ethanol may be 90% for the lipids and 0% for the RNA component. After mixing into a 45% ethanol mixture, the RNA-lipid particles can be immediately diluted into citrate buffer with a final concentration of ethanol at 30%. The ethanol and citrate buffer can be exchanged for PBS, pH 7.2 by overnight dialysis in a Pierce dialysis cassette with a 2K MWCO membrane. Particle sizing and PAGE gel analysis of each siRNA lipid particle can be performed to confirm successful entrapment. PAGE gel results can confirm that an siRNA is intact after exposure to multiple processing steps.

The nucleic acid component, lipopeptides, and any additional components may be mixed together first in a suitable medium such as a cell culture medium, after which one or more additional lipids or compounds may be added to the mixture. Alternatively, the lipopeptides can be mixed together first in a suitable medium such as a cell culture medium, after which the nucleic acid component can be added.

Within certain embodiments of the invention, a dsRNA is admixed with one or more lipopeptides, or a combination of one or more lipopeptides and non-cationic lipids.

The interfering RNA agent may also be complexed with, or conjugated to a lipopeptide or a polymeric lipid, and admixed with one or more non-cationic lipids, or a combination of one or more non-cationic and cationic lipids.

An interfering RNA agent and a lipopeptide may be mixed together first, followed by the addition of one or more non-cationic lipids, or a combination of non-cationic and cationic lipids added in a suitable medium such as a cell culture medium. Alternatively, the lipopeptides and lipid components may be mixed first, followed by the addition of the RNA agent in a suitable medium.

RNA Therapeutics and RNA Interference

This invention provides compositions and methods for modulating gene expression by RNA interference. A composition of this invention can deliver a ribonucleic acid agent to a cell which can produce the response of RNAi. Examples of nucleic acid agents useful for this invention include double-stranded nucleic acids, modified or degradation-resistant nucleic acids, RNA, siRNA, siNA, mdRNA, shRNA, single-stranded nucleic acids, DNA-RNA chimeras, antisense nucleic acids, and ribozymes. As used herein, the terms siRNA, siNA, and shRNA include precursors of siRNA, siNA, and shRNA, respectively. For example, the term siRNA includes an RNA or double-stranded RNA that is suitable as a dicer substrate.

Meroduplex RNA (mdRNA) is described in U.S. Provisional Application No. 60/934,930, as well as International Publication No. WO/2007/056153.

Ribonucleic acid agents useful for this invention may be targeted to various genes. For example, a siRNA agent of this invention may have a sequence that is complementary to a region of a TNF-alpha gene. In some embodiments of this invention, compounds and compositions are useful to regulate expression of tumor necrosis factor-α (TNF-α). TNF-α can be linked, for example, to inflammatory processes which occur in pulmonary diseases, and can have anti-inflammatory effects. Blocking TNF-α by delivery of a composition of this invention can be useful to treat or prevent the signs and/or symptoms of rheumatoid arthritis. This invention provides compositions and methods for modulating expression and activity of TNF-α by RNA interference.

Expression and/or activity of TNF-α can be modulated by delivering to a cell, for example, the siRNA molecule Inm-4. Inm-4 is a double stranded 21-nt siRNA molecule with sequence homology to the mouse TNF-α gene. Inm-4 has a 3' dTdT overhang on the sense strand and a 3' dAdT overhang on the antisense strand. The primary structure of Inm-4 is:

```
                                    (SEQ ID NO: 301)
sense
5'-CCGUCAGCCGAUUUGCUAUdTdT (SEQ ID NO: 302)
antisense
5'-AUAGCAAAUCGGCUGACGGdTdT
```

Expression and/or activity of TNF-α can be modulated by delivering to a cell, for example, the siRNA molecule LC20. LC20 is a double stranded 21-nt siRNA molecule with sequence homology to the human TNF-α gene. LC20 is directed against the 3'-UTR region of human TNF-α. LC 20 has 19 base pairs with a 3' dTdT overhang on the sense strand and a 3' dAdT overhang on the antisense strand. The molecular weight of the sodium salt form is 14,298. The primary structure of LC20 is:

```
                                    (SEQ ID NO: 303)
sense
(5') GGGUCGGAACCCAAGCUUAdTdT (SEQ ID NO: 304)
antisense
(5') UAAGCUUGGGUUCCGACCCdTdA
```

A β-galactoside reporter cell line was used to assay the RNAi activity of various formulations. The structure of Lac-Z is:

```
Sense: CN2938.
                                    (SEQ ID NO: 305)
5'-CUACACAAAUCAGCGAUUUdTdT-3'

Antisense: CN2939.
                                    (SEQ ID NO: 306)
5'-AAAUCGCUGAUUUGUGUAGdTdC-3'
```

A siRNA of this invention may have a sequence that is complementary to a region of a viral gene. For example, some compositions and methods of this invention are useful to regulate expression of the viral genome of an influenza.

In this context, this invention provides compositions and methods for modulating expression and infectious activity of an influenza by RNA interference. Expression and/or activity of an influenza can be modulated by delivering to a cell, for example, a short interfering RNA molecule having a sequence that is complementary to a region of a RNA polymerase subunit of an influenza. For example, in Table 5 are shown double-stranded siRNA molecules with sequence homology to an RNA polymerase subunit of an influenza.

TABLE 5

Double-Stranded siRNA Molecules Targeted to Influenza

| siRNA | Subunit | SEQUENCE |
|---|---|---|
| G3789 | PB2 | (SEQ ID NO 307) CGGGACUCUAGCAUACUUAdTdT (SEQ ID NO 308) UAAGUAUGCUAGAGUCCCGdTdT |
| G3807 | PB2 | (SEQ ID NO 309) ACUGACAGCCAGACAGCGAdTdT (SEQ ID NO 310) UCGCUGUCUGGCUGUCAGUdTdT |
| G3817 | PB2 | (SEQ ID NO 311) AGACAGCGACCAAAAGAAUdTdT (SEQ ID NO 312) AUUCUUUUGGUCGCUGUCUdTdT |
| G6124 | PB1 | (SEQ ID NO 313) AUGAAGAUCUGUUCCACCAdTdT (SEQ ID NO 314) UGGUGGAACAGAUCUUCAUdTdT |
| G6129 | PB1 | (SEQ ID NO 315) GAUCUGUUCCACCAUUGAAdTdT (SEQ ID NO 316) UUCAAUGGUGGAACAGAUCdTdT |
| G8282 | PA | (SEQ ID NO 317) GCAAUUGAGGAGUGCCUGAdTdT (SEQ ID NO 318) UCAGGCACUCCUCAAUUGCdTdT |
| G8286 | PA | (SEQ ID NO 319) UUGAGGAGUGCCUGAUUAAdTdT (SEQ ID NO 320) UUAAUCAGGCACUCCUCAAdTdT |
| G1498 | NP | (SEQ ID NO 321) GGAUCUUAUUUCUUCGGAGdTdT (SEQ ID NO 322) CUCCGAAGAAAUAAGAUCCdTdT |

A siRNA of this invention may have a sequence that is complementary to a region of a RNA polymerase subunit of an influenza.

This invention provides compositions and methods to administer siNAs directed against a mRNA of an influenza, which effectively down-regulates an influenza RNA and thereby reduces, prevents, or ameliorates an influenza infection.

In some embodiments, this invention provides compositions and methods for inhibiting expression of a target transcript in a subject by administering to the subject a composition containing an effective amount of an RNAi-inducing compound such as a short interfering oligonucleotide molecule, or a precursor thereof. RNAi uses small interfering RNAs (siRNAs) to target messenger RNA (mRNAs) and attenuate translation. A siRNA as used in this invention may be a precursor for dicer processing such as, for example, a long dsRNA processed into a siRNA. This invention provides methods of treating or preventing diseases or conditions associated with expression of a target transcript or activity of a peptide or protein encoded by the target transcript.

A therapeutic strategy based on RNAi can be used to treat a wide range of diseases by shutting down the growth or function of a virus or microorganism, as well as by shutting down the function of an endogenous gene product in the pathway of the disease.

In some embodiments, this invention provides novel compositions and methods for delivery of RNAi-inducing entities such as short interfering oligonucleotide molecules, and precursors thereof. In particular, this invention provides compositions containing an RNAi-inducing entity which is targeted to one or more transcripts of a cell, tissue, and/or organ of a subject.

A siRNA can be two RNA strands having a region of complementarity about 19 nucleotides in length. A siRNA optionally includes one or two single-stranded overhangs or loops.

A shRNA can be a single RNA strand having a region of self-complementarity. The single RNA strand may form a hairpin structure with a stem and loop and, optionally, one or more unpaired portions at the 5' and/or 3' portion of the RNA.

The active therapeutic agent can be a chemically-modified siNA with improved resistance to nuclease degradation in vivo, and/or improved cellular uptake, which retains RNAi activity.

A siRNA agent of this invention may have a sequence that is complementary to a region of a target gene. A siRNA of this invention may have 29-50 base pairs, for example, a dsRNA having a sequence that is complementary to a region of a target gene. Alternately, the double-stranded nucleic acid can be a dsDNA.

In some embodiments, the active agent can be a short interfering nucleic acid (siNA), short interfering RNA (siRNA), double-stranded RNA (dsRNA), micro-RNA, or short hairpin RNA (shRNA) that can modulate expression of a gene product.

Comparable methods and compositions are provided that target expression of one or more different genes associated with a particular disease condition in a subject, including any of a large number of genes whose expression is known to be aberrantly increased as a causal or contributing factor associated with the selected disease condition.

The RNAi-inducing compound of this invention can be administered in conjunction with other known treatments for a disease condition.

In some embodiments, this invention features compositions containing a small nucleic acid molecule, such as short interfering nucleic acid, a short interfering RNA, a double-stranded RNA, a micro-RNA, or a short hairpin RNA, admixed or complexed with, or conjugated to, a delivery-enhancing compound.

As used herein, the terms "short interfering nucleic acid," "siNA," "short interfering RNA," "siRNA," "short interfering nucleic acid molecule," "short interfering oligonucleotide molecule," and "chemically-modified short interfering nucleic acid molecule," refer to any nucleic acid molecule capable of inhibiting or down regulating gene expression or viral replication, for example, by mediating RNA interference (RNAi) or gene silencing in a sequence-specific manner.

In some embodiments, the siNA is a double-stranded polynucleotide molecule comprising self-complementary sense and antisense regions, wherein the antisense region comprises a nucleotide sequence that is complementary to a nucleotide sequence in a target ribonucleic acid molecule for down regulating expression, or a portion thereof, and the sense region comprises a nucleotide sequence corresponding to (i.e., which is substantially identical in sequence to) the target ribonucleic acid sequence or portion thereof.

"siNA" means a small interfering nucleic acid, for example a siRNA, that is a short-length double-stranded nucleic acid, or optionally a longer precursor thereof. The length of useful siNAs within this invention will in some embodiments be preferred at a length of approximately 20 to 50 bp. However, there is no particular limitation to the length of useful siNAs, including siRNAs. For example, siNAs can initially be presented to cells in a precursor form that is substantially different than a final or processed form of the siNA that will exist and exert gene silencing activity upon delivery, or after delivery, to the target cell. Precursor forms of siNAs may, for example, include precursor sequence elements that are processed, degraded, altered, or cleaved at or after the time of delivery to yield a siNA that is active within the cell to mediate gene silencing. In some embodiments, useful siNAs will have a precursor length, for example, of approximately 100-200 base pairs, or 50-100 base pairs, or less than about 50 base pairs, which will yield an active, processed siNA within the target cell. In other embodiments, a useful siNA or siNA precursor will be approximately 10 to 49 bp, or 15 to 35 bp, or about 21 to 30 bp in length.

In some embodiments of this invention, polynucleotide delivery-enhancing polypeptides are used to facilitate delivery of larger nucleic acid molecules than conventional siNAs, including large nucleic acid precursors of siNAs. For example, the methods and compositions herein may be employed for enhancing delivery of larger nucleic acids that represent "precursors" to desired siNAs, wherein the precursor amino acids may be cleaved or otherwise processed before, during or after delivery to a target cell to form an active siNA for modulating gene expression within the target cell.

For example, a siNA precursor polynucleotide may be selected as a circular, single-stranded polynucleotide, having two or more loop structures and a stem comprising self-complementary sense and antisense regions, wherein the antisense region comprises a nucleotide sequence that is complementary to a nucleotide sequence in a target nucleic acid molecule or a portion thereof, and the sense region having nucleotide sequence corresponding to the target nucleic acid sequence or a portion thereof, and wherein the circular polynucleotide can be processed either in vivo or in vitro to generate an active siNA molecule capable of mediating RNAi.

siNA molecules of this invention, particularly non-precursor forms, can be less than 30 base pairs, or about 17-19 bp, or 19-21 bp, or 21-23 bp.

siRNAs can mediate selective gene silencing in the mammalian system. Hairpin RNAs, with a short loop and 19 to 27 base pairs in the stem, also selectively silence expression of genes that are homologous to the sequence in the double-stranded stem. Mammalian cells can convert short hairpin RNA into siRNA to mediate selective gene silencing.

RISC mediates cleavage of single stranded RNA having sequence complementary to the antisense strand of the siRNA duplex. Cleavage of the target RNA takes place within the region complementary to the antisense strand of the siRNA duplex. siRNA duplexes of 21 nucleotides are typically most active when containing two-nucleotide 3'-overhangs.

Replacing the 3'-overhanging segments of a 21-mer siRNA duplex having 2-nucleotide 3' overhangs with deoxyribonucleotides may not have an adverse effect on RNAi activity. Replacing up to 4 nucleotides on each end of the siRNA with deoxyribonucleotides can be tolerated whereas complete substitution with deoxyribonucleotides may result in no RNAi activity.

Alternatively, the siNAs can be delivered as single or multiple transcription products expressed by a polynucleotide vector encoding the single or multiple siNAs and directing their expression within target cells. In these embodiments the double-stranded portion of a final transcription product of the siRNAs to be expressed within the target cell can be, for example, 15 to 49 bp, 15 to 35 bp, or about 21 to 30 bp long.

In some embodiments of this invention, the double-stranded region of siNAs in which two strands are paired may contain bulge or mismatched portions, or both. Double-stranded portions of siNAs in which two strands are paired are not limited to completely paired nucleotide segments, and may contain nonpairing portions due to, for example, mismatch (the corresponding nucleotides not being complementary), bulge (lacking in the corresponding complementary nucleotide on one strand), or overhang. Nonpairing portions can be contained to the extent that they do not interfere with siNA formation. In some embodiments, a "bulge" may be 1 to 2 nonpairing nucleotides, and the double-stranded region of siNAs in which two strands pair up may contain from about 1 to 7, or about 1 to 5 bulges. In addition, "mismatch" portions contained in the double-stranded region of siNAs may be present in numbers from about 1 to 7, or about 1 to 5. Most often in the case of mismatches, one of the nucleotides is guanine, and the other is uracil. Such mismatching may be attributable, for example, to a mutation from C to T, G to A, or mixtures thereof, in a corresponding DNA coding for sense RNA, but other causes are also contemplated.

The terminal structure of siNAs of this invention may be either blunt or cohesive (overhanging) as long as the siNA retains its activity to silence expression of target genes. The cohesive (overhanging) end structure is not limited to the 3' overhang, but includes the 5' overhanging structure as long as it retains activity for inducing gene silencing. In addition, the number of overhanging nucleotides is not limited to 2 or 3 nucleotides, but can be any number of nucleotides as long as it retains activity for inducing gene silencing. For example, overhangs may comprise from 1 to about 8 nucleotides, or from 2 to 4 nucleotides.

The length of siNAs having cohesive (overhanging) end structure may be expressed in terms of the paired duplex portion and any overhanging portion at each end. For example, a 25/27-mer siNA duplex with a 2-bp 3' antisense overhang has a 25-mer sense strand and a 27-mer antisense strand, where the paired portion has a length of 25 bp.

Any overhang sequence may have low specificity to a target gene, and may not be complementary (antisense) or identical (sense) to the target gene sequence. As long as the siNA retains activity for gene silencing, it may contain in the overhang portion a low molecular weight structure, for example, a natural RNA molecule such as a tRNA, an rRNA, a viral RNA, or an artificial RNA molecule.

The terminal structure of the siNAs may have a stem-loop structure in which ends of one side of the double-stranded nucleic acid are connected by a linker nucleic acid, for example, a linker RNA. The length of the double-stranded region (stem portion) can be, for example, 15 to 49 bp, or 15 to 35 bp, or about 21 to 30 bp long. Alternatively, the length of the double-stranded region that is a final transcription product of siNAs to be expressed in a target cell may be, for example, approximately 15 to 49 bp, or 15 to 35 bp, or about 21 to 30 bp long.

The siNA can contain a single stranded polynucleotide having a nucleotide sequence complementary to a nucleotide sequence in a target nucleic acid molecule, or a portion thereof, wherein the single stranded polynucleotide can contain a terminal phosphate group, such as a 5'-phosphate (see e.g. Martinez, et al., *Cell*. 110:563-574, 2002, and Schwarz, et al., *Molecular Cell* 10:537-568, 2002, or 5',3'-diphosphate.

As used herein, the term siNA molecule is not limited to molecules containing only naturally-occurring RNA or DNA, but also encompasses chemically-modified nucleotides and non-nucleotides. In some embodiments, the short interfering nucleic acid molecules of the invention lack 2'-hydroxy (2'-OH) containing nucleotides. In some embodiments, short interfering nucleic acids do not require the presence of nucleotides having a 2'-hydroxy group for mediating RNAi and as such, short interfering nucleic acid molecules of this invention optionally do not include any ribonucleotides (e.g., nucleotides having a 2'-OH group). siNA molecules that do not require the presence of ribonucleotides within the siNA molecule to support RNAi can, however, have an attached linker or linkers or other attached or associated groups, moieties, or chains containing one or more nucleotides with 2'-OH groups. siNA molecules can comprise ribonucleotides in at least about 5, 10, 20, 30, 40, or 50% of the nucleotide positions.

As used herein, the term siNA encompasses nucleic acid molecules that are capable of mediating sequence specific RNAi such as, for example, short interfering RNA (siRNA) molecules, double-stranded RNA (dsRNA) molecules, micro-RNA molecules, short hairpin RNA (shRNA) molecules, short interfering oligonucleotide molecules, short interfering nucleic acid molecules, short interfering modified oligonucleotide molecules, chemically-modified siRNA molecules, and post-transcriptional gene silencing RNA (ptgsRNA) molecules, among others.

In some embodiments, siNA molecules comprise separate sense and antisense sequences or regions, wherein the sense and antisense regions are covalently linked by nucleotide or non-nucleotide linker molecules, or are non-covalently linked by ionic interactions, hydrogen bonding, van der waals interactions, hydrophobic interactions, and/or stacking interactions.

"Antisense RNA" is an RNA strand having a sequence complementary to a target gene mRNA, that can induce RNAi by binding to the target gene mRNA.

"Sense RNA" is an RNA strand having a sequence complementary to an antisense RNA, and anneals to its complementary antisense RNA to form a siRNA.

As used herein, the term "RNAi construct" or "RNAi precursor" refers to an RNAi-inducing compound such as small interfering RNAs (siRNAs), hairpin RNAs, and other RNA species which can be cleaved in vivo to form a siRNA. RNAi precursors herein also include expression vectors (also referred to as RNAi expression vectors) capable of giving rise to transcripts which form dsRNAs or hairpin RNAs in cells, and/or transcripts which can produce siRNAs in vivo.

A siHybrid molecule is a double-stranded nucleic acid that has a similar function to siRNA. Instead of a double-stranded RNA molecule, a siHybrid is comprised of an RNA strand and a DNA strand. Preferably, the RNA strand is the antisense strand which binds to a target mRNA. The siHybrid created by the hybridization of the DNA and RNA strands have a hybridized complementary portion and preferably at least one 3' overhanging end.

siNAs for use within the invention can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 19 base pairs). The antisense strand may comprise a nucleotide sequence that is complementary to a nucleotide sequence in a target nucleic acid molecule or a portion thereof, and the sense strand may comprise a nucleotide sequence corresponding to the target nucleic acid sequence or a portion thereof. Alternatively, the siNA can be assembled from a single oligonucleotide, where the self-complementary sense and antisense regions of the siNA are linked by means of a nucleic acid-based or non-nucleic acid-based linker(s).

In some embodiments, siNAs for intracellular delivery can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof, and the sense region comprises a nucleotide sequence corresponding to the target nucleic acid sequence or a portion thereof.

Examples of chemical modifications that can be made in an siNA include phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation.

The antisense region of a siNA molecule can include a phosphorothioate internucleotide linkage at the 3'-end of said antisense region. The antisense region can comprise about one to about five phosphorothioate internucleotide linkages at the 5'-end of said antisense region. The 3'-terminal nucleotide overhangs of a siNA molecule can include ribonucleotides or deoxyribonucleotides that are chemically-modified at a nucleic acid sugar, base, or backbone. The 3'-terminal nucleotide overhangs can include one or more universal base ribonucleotides. The 3'-terminal nucleotide overhangs can comprise one or more acyclic nucleotides.

For example, a chemically-modified siNA can have 1, 2, 3, 4, 5, 6, 7, 8, or more phosphorothioate internucleotide linkages in one strand, or can have 1 to 8 or more phosphorothioate internucleotide linkages in each strand. The phosphorothioate internucleotide linkages can be present in one or both oligonucleotide strands of the siNA duplex, for example in the sense strand, the antisense strand, or both strands.

siNA molecules can comprise one or more phosphorothioate internucleotide linkages at the 3'-end, the 5'-end, or both of the 3'- and 5'-ends of the sense strand, the antisense strand, or in both strands. For example, an exemplary siNA molecule can include 1, 2, 3, 4, 5, or more consecutive phosphorothioate internucleotide linkages at the 5'-end of the sense strand, the antisense strand, or both strands.

In some embodiments, a siNA molecule includes 1, 2, 3, 4, 5, 6, 7, 8, 9, 10, or more pyrimidine phosphorothioate internucleotide linkages in the sense strand, the antisense strand, or in both strands.

In some embodiments, a siNA molecule includes 1, 2, 3, 4, 5, 6, 7, 8, 9, 10, or more purine phosphorothioate internucleotide linkages in the sense strand, the antisense strand, or in both strands.

A siNA molecule can include a circular nucleic acid molecule, wherein the siNA is about 38 to about 70, for example, about 38, 40, 45, 50, 55, 60, 65, or 70 nucleotides in length, having about 18 to about 23, for example, about 18, 19, 20, 21, 22, or 23 base pairs, wherein the circular oligonucleotide forms a dumbbell-shaped structure having about 19 base pairs and 2 loops.

A circular siNA molecule can contain two loop motifs, wherein one or both loop portions of the siNA molecule is biodegradable. For example, the loop portions of a circular siNA molecule may be transformed in vivo to generate a double-stranded siNA molecule with 3'-terminal overhangs, such as 3'-terminal nucleotide overhangs comprising about 2 nucleotides.

Modified nucleotides in a siNA molecule can be in the antisense strand, the sense strand, or both. For example, modified nucleotides can have a Northern conformation (e.g., Northern pseudorotation cycle; see e.g., Saenger, *Principles of Nucleic Acid Structure*, Springer-Verlag ed., 1984). Examples of nucleotides having a Northern configuration include locked nucleic acid (LNA) nucleotides (e.g., 2'-O, 4'-C-methylene-(D-ribofuranosyl) nucleotides), 2'-methoxyethoxy (MOE) nucleotides, 2'-methyl-thio-ethyl, 2'-deoxy-2'-fluoro nucleotides, 2'-deoxy-2'-chloro nucleotides, 2'-azido nucleotides, and 2'-O-methyl nucleotides.

Chemically modified nucleotides can be resistant to nuclease degradation while at the same time maintaining the capacity to mediate RNAi.

The sense strand of a double stranded siNA molecule may have a terminal cap moiety such as an inverted deoxyabasic moiety, at the 3'-end, 5'-end, or both 3' and 5'-ends of the sense strand.

Examples of conjugates include conjugates and ligands described in Vargeese, et al., U.S. application Ser. No. 10/427,160, filed Apr. 30, 2003, incorporated by reference herein in its entirety, including the drawings.

In some embodiments of this invention, the conjugate may be covalently attached to the chemically-modified siNA molecule via a biodegradable linker. For example, the conjugate molecule may be attached at the 3'-end of either the sense strand, the antisense strand, or both strands of the chemically-modified siNA molecule.

In some embodiments, the conjugate molecule is attached at the 5'-end of either the sense strand, the antisense strand, or both strands of the chemically-modified siNA molecule. In some embodiments, the conjugate molecule is attached both the 3'-end and 5'-end of either the sense strand, the antisense strand, or both strands of the chemically-modified siNA molecule, or any combination thereof.

In some embodiments, a conjugate molecule comprises a molecule that facilitates delivery of a chemically-modified siNA molecule into a biological system, such as a cell.

In some embodiments, a conjugate molecule attached to the chemically-modified siNA molecule is a polyethylene glycol, human serum albumin, or a ligand for a cellular receptor that can mediate cellular uptake. Examples of specific conjugate molecules contemplated by the instant invention that can be attached to chemically-modified siNA molecules are described in Vargeese, et al., U.S. Patent Publication Nos. 2003/0130186 and 2004/0110296.

A siNA may be contain a nucleotide, non-nucleotide, or mixed nucleotide/non-nucleotide linker that joins the sense region of the siNA to the antisense region of the siNA. In some embodiments, a nucleotide linker can be 3, 4, 5, 6, 7, 8, 9, or 10 nucleotides in length. In some embodiments, the nucleotide linker can be a nucleic acid aptamer. As used herein, the terms "aptamer" or "nucleic acid aptamer" encompass a nucleic acid molecule that binds specifically to a target molecule, wherein the nucleic acid molecule contains a sequence that is recognized by the target molecule in its natural setting. Alternately, an aptamer can be a nucleic acid molecule that binds to a target molecule where the target molecule does not naturally bind to a nucleic acid.

For example, the aptamer can be used to bind to a ligand-binding domain of a protein, thereby preventing interaction of the naturally occurring ligand with the protein. See, for example, Gold, et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287:820, 2000; and Jayasena, *Clinical Chemistry* 45:1628, 1999.

A non-nucleotide linker can be an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, *Nucleic Acids Res.* 18:6353, 1990, and *Nucleic Acids Res.* 15:3113, 1987; Cload and Schepartz, *J. Am. Chem. Soc.* 113:6324, 1991; Richardson and Schepartz, *J. Am. Chem. Soc.* 113:5109, 1991; Ma, et al., *Nucleic Acids Res.* 21:2585, 1993, and *Biochemistry* 32:1751, 1993; Durand, et al., *Nucleic Acids Res.* 18:6353, 1990; McCurdy, et al., *Nucleosides & Nucleotides* 10:287, 1991; Jaschke, et al., *Tetrahedron Lett.* 34:301-304, 1993; Ono, et al., *Biochemistry* 30:9914, 1991; Arnold, et al., International Publication No. WO/1989/02439; Usman, et al., International Publication No. WO/1995/06731; Dudycz, et al., International Publication No. WO/1995/11910, and Ferentz and Verdine, *J. Am. Chem. Soc.* 113:4000, 1991.

A "non-nucleotide linker" refers to a group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In some embodiments, modified siNA molecule can have phosphate backbone modifications including one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl substitutions. Examples of oligonucleotide backbone modifications are given in Hunziker and Leumann, *Nucleic Acid Analogues: Synthesis and Properties, in Modern Synthetic Methods*, VCH, pp. 331-417, 1995, and Mesmaeker, et al., *Novel Backbone Replacements for Oligonucleotides, in Carbohydrate Modifications in Antisense Research*, ACS, pp. 24-39, 1994.

siNA molecules, which can be chemically-modified, can be synthesized by: (a) synthesis of two complementary strands of the siNA molecule; and (b) annealing the two complementary strands together under conditions suitable to obtain a double-stranded siNA molecule. In some embodiments, synthesis of the complementary portions of the siNA molecule is by solid phase oligonucleotide synthesis, or by solid phase tandem oligonucleotide synthesis.

Oligonucleotides (e.g., certain modified oligonucleotides or portions of oligonucleotides lacking ribonucleotides) are synthesized using protocols known in the art, for example, as described in Caruthers, et al., *Methods in Enzymology* 211:3-19, 1992; Thompson, et al., International Publication No. WO/1999/54459; Wincott, et al., *Nucleic Acids Res.* 23:2677-2684, 1995; Wincott, et al., *Methods Mol. Bio.* 74:59, 1997; Brennan, et al., *Biotechnol Bioeng.* 61:33-45, 1998; and Brennan, U.S. Pat. No. 6,001,311. Synthesis of RNA, including certain siNA molecules of the invention, follows general procedures as described, for example, in Usman, et al., *J. Am. Chem. Soc.* 109:7845, 1987; Scaringe, et al., *Nucleic Acids Res.* 18:5433, 1990; and Wincott, et al., *Nucleic Acids Res.* 23:2677-2684, 1995; Wincott, et al., *Methods Mol. Bio.* 74:59, 1997.

An "asymmetric hairpin" as used herein is a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop.

An "asymmetric duplex" as used herein is a siNA molecule having two separate strands comprising a sense region and an antisense region, wherein the sense region comprises fewer nucleotides than the antisense region to the extent that the sense region has enough complementary nucleotides to base pair with the antisense region and form a duplex.

To "modulate gene expression" as used herein is to upregulate or downregulate expression of a target gene, which can include upregulation or downregulation of mRNA levels present in a cell, or of mRNA translation, or of synthesis of protein or protein subunits, encoded by the target gene.

The terms "inhibit," "down-regulate," or "reduce expression" as used herein mean that the expression of the gene, or level of RNA molecules or equivalent RNA molecules encoding one or more proteins or protein subunits, or level or activity of one or more proteins or protein subunits encoded by a target gene, is reduced below that observed in the absence of the nucleic acid molecules (e.g., siNA) of the invention.

"Gene silencing" as used herein refers to partial or complete inhibition of gene expression in a cell and may also be referred to as "gene knockdown." The extent of gene silencing may be determined by methods known in the art, some of which are summarized in International Publication No. WO/1999/32619.

As used herein, the terms "ribonucleic acid" and "RNA" refer to a molecule containing at least one ribonucleotide residue. A ribonucleotide is a nucleotide with a hydroxyl group at the 2' position of a β-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of a siNA or internally, for example at one or more nucleotides of an RNA.

Nucleotides in an RNA molecule include non-standard nucleotides, such as non-naturally occurring nucleotides or chemically synthesized nucleotides or deoxynucleotides. These altered RNAs can be referred to as analogs.

By "highly conserved sequence region" is meant, a nucleotide sequence of one or more regions in a target gene does not vary significantly from one generation to the other or from one biological system to the other.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" is meant a nucleotide sequence of a siNA molecule having complementarity to a target nucleic acid sequence. In addition, the antisense region of a siNA molecule can include a nucleic acid sequence having complementarity to a sense region of the siNA molecule.

By "target nucleic acid" is meant any nucleic acid sequence whose expression or activity is to be modulated. A target nucleic acid can be DNA or RNA.

By "complementarity" is meant that a nucleic acid can form hydrogen bond(s) with another nucleic acid sequence either by traditional Watson-Crick or by other non-traditional modes of binding.

The term "biodegradable linker" as used herein, refers to a nucleic acid or non-nucleic acid linker molecule that is designed as a biodegradable linker to connect one molecule to another molecule, for example, a biologically active molecule to a siNA molecule or the sense and antisense strands of a siNA molecule. The biodegradable linker is designed such that its stability can be modulated for a particular purpose, such as delivery to a particular tissue or cell type. The stability of a nucleic acid-based biodegradable linker molecule can be variously modulated, for example, by combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

In connection with 2'-modified nucleotides as described herein, by "amino" is meant 2'-NH$_2$ or 2'-O—NH$_2$, which can be modified or unmodified. Such modified groups are described, for example, in Eckstein, et al., U.S. Pat. No. 5,672,695 and Matulic-Adamic, et al., U.S. Pat. No. 6,248,878.

Supplemental or complementary methods for delivery of nucleic acid molecules for use within then invention are described, for example, in Akhtar et al., *Trends Cell Bio.* 2:139, 1992; "Delivery Strategies for Antisense Oligonucleotide Therapeutics," ed Akhtar, 1995, Maurer et al., *Mol. Membr. Biol.* 16:129-140, 1999; Hofland and Huang, *Handb. Exp. Pharmacol.* 137:165-192, 1999; and Lee et al., *ACS Symp. Ser.* 752:184-192, 2000. Sullivan, et al., International Publication No. WO/1994/02595, further describes general methods for delivery of enzymatic nucleic acid molecules.

Nucleic acid molecules can be administered within formulations that include one or more additional components, such as a pharmaceutically acceptable carrier, diluent, excipient, adjuvant, emulsifier, buffer, stabilizer, or preservative.

As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. Examples of ingredients of the above categories can be found in the *U.S. Pharmacopeia National Formulary,* 1990, pp. 1857-1859, as well as in Raymond C. Rowe, et al., *Handbook of Pharmaceutical Excipients,* 5th ed., 2006, and "Remington: The Science and Practice of Pharmacy," 21st ed., 2006, editor David B. Troy.

Examples of preservatives include phenol, methyl paraben, paraben, m-cresol, thiomersal, benzylalkonium chloride, and mixtures thereof.

Examples of surfactants include oleic acid, sorbitan trioleate, polysorbates, lecithin, phosphatidylcholines, various long chain diglycerides and phospholipids, and mixtures thereof.

Examples of phospholipids include phosphatidylcholine, lecithin, phosphatidylglycerol, phosphatidylinositol, phosphatidylserine, and phosphatidylethanolamine, and mixtures thereof.

Examples of dispersants include ethylenediaminetetraacetic acid.

Examples of gases include nitrogen, helium, chlorofluorocarbons (CFCs), hydrofluorocarbons (HFCs), carbon dioxide, air, and mixtures thereof.

In certain embodiments, the siNA and/or the polypeptide can be encapsulated in liposomes, or reside either internal or external to a liposome, or exist within liposome layers, or be administered by iontophoresis, or incorporated into other vehicles, such as hydrogels, cyclodextrins, biodegradable nanocapsules, bioadhesive microspheres, or proteinaceous vectors. See, for example, O'Hare and Normand, International Publication No. WO/2000/53722. Alternatively, a nucleic acid composition can be locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., *Clin. Cancer Res.* 5:2330-2337, 1999, and Barry et al., International Publication No. WO/1999/31262.

The compositions of this invention can be effectively employed as pharmaceutical agents. Pharmaceutical agents prevent, modulate the occurrence or severity of, or treat (alleviate one or more symptom(s) to a detectable or measurable extent) of a disease state or other adverse condition in a patient.

In some embodiments, this invention provides pharmaceutical compositions and methods featuring the presence or administration of one or more polynucleic acid(s), typically one or more siNAs, combined, complexed, or conjugated with a lipid, which may further be formulated with a pharmaceutically-acceptable carrier, such as a diluent, stabilizer, or buffer.

Typically, the siNA will target a gene that is expressed at an elevated level as a causal or contributing factor associated with the subject disease state or adverse condition. In this context, the siNA will effectively downregulate expression of the gene to levels that prevent, alleviate, or reduce the severity or recurrence of one or more associated disease symptoms. Alternatively, for various distinct disease models where expression of the target gene is not necessarily elevated as a consequence or sequel of disease or other adverse condition, down regulation of the target gene will nonetheless result in a therapeutic result by lowering gene expression (i.e., to reduce levels of a selected mRNA and/or protein product of the target gene). Alternatively, siNAs of the invention may be targeted to lower expression of one gene, which can result in upregulation of a "downstream" gene whose expression is negatively regulated by a product or activity of the target gene.

This siNAs of the present invention may be administered in any form, for example transdermally or by local injection (e.g., local injection at sites of psoriatic plaques to treat psoriasis, or into the joints of patients afflicted with psoriatic arthritis or RA). In more detailed embodiments, the invention provides formulations and methods to administer therapeutically effective amounts of siNAs directed against of a mRNA of TNF-α, which effectively down-regulate the TNF-α RNA and thereby reduce or prevent one or more TNF-α-associated inflammatory condition(s). Comparable methods and compositions are provided that target expression of one or more different genes associated with a selected disease condition in animal subjects, including any of a large number of genes whose expression is known to be aberrantly increased as a causal or contributing factor associated with the selected disease condition.

The compositions of the present invention may also be formulated and used as tablets, capsules or elixirs for oral administration, suppositories for rectal administration, sterile solutions, suspensions for injectable administration, and the other forms known in the art.

A pharmacological composition or formulation refers to a composition or formulation in a form suitable for administration, for example, systemic administration, into a cell or patient, including for example a human. Suitable forms, in part, depend upon the use or the route of entry, for example oral, transdermal, transepithelial, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity.

By "systemic administration" is meant in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular.

Examples of agents suitable for formulation with the nucleic acid molecules of this invention include: P-glycoprotein inhibitors (such as Pluronic P85), which can enhance entry of drugs into the CNS (Jolliet-Riant and Tillement, *Fundam. Clin. Pharmacol.* 13:16-26, 1999); biodegradable polymers, such as poly (DL-lactide-coglycolide) microspheres for sustained release delivery after intracerebral implantation (Emerich, D. F., et al., *Cell Transplant* 8:47-58, 1999, Alkermes, Inc., Cambridge, Mass.); and loaded nanoparticles, such as those made of polybutylcyanoacrylate, which can deliver drugs across the blood brain barrier and can alter neuronal uptake mechanisms (*Prog. Neuropsychopharmacol Biol. Psychiatry* 23:941-949, 1999). Other examples of delivery strategies for the nucleic acid molecules of the instant invention include material described in Boado, et al., *J. Pharm. Sci.* 87:1308-1315, 1998; Tyler, et al., *FEBS Lett.* 421:280-284, 1999; Pardridge, et al., *PNAS USA*. 92:5592-5596, 1995; Boado, *Adv. Drug Delivery Rev.* 15:73-107, 1995; Aldrian-Herrada et al., *Nucleic Acids Res.* 26:4910-4916, 1998; and Tyler, et al., *PNAS USA*. 96:7053-7058, 1999.

The present invention also includes compositions prepared for storage or administration, which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro ed. 1985). For example, preservatives, stabilizers, dyes and flavoring agents may be provided. These include sodium benzoate, sorbic acid and esters of p-hydroxybenzoic acid. In addition, antioxidants and suspending agents may be used.

A pharmaceutically effective dose is that dose required to prevent, inhibit the occurrence of, treat, or alleviate a symptom to some extent of a disease state. An amount of from 0.01 mg/kg to 50 mg/kg body weight/day of active nucleic acid should be administered.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The siNAs can also be administered in the form of suppositories, for example, for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

The siNAs can be modified extensively to enhance stability by modification with nuclease resistant groups, for example, 2'-amino, 2'-C-allyl, 2'-fluoro, 2'-O-methyl, 2'-H. For a review see Usman and Cedergren, *TIBS* 17:34, 1992; Usman, et al., *Nucleic Acids Symp. Ser.* 31:163, 1994. SiNA constructs can be purified by gel electrophoresis using general methods or can be purified by high pressure liquid chromatography and re-suspended in water.

Chemically synthesizing nucleic acid molecules with modifications (base, sugar and/or phosphate) can prevent their degradation by serum ribonucleases, which can increase their potency. See for example, Eckstein, et al., International Publication No. WO/1992/07065; Perrault et al., *Nature* 344:565, 1990; Pieken, et al., *Science* 253, 314, 1991; Usman and Cedergren, *Trends in Biochem. Sci.* 17:334, 1992; Usman, et al., International Publication No. WO/1993/15187; and Rossi et al., International Publication No. WO/1991/03162; Sproat, U.S. Pat. No. 5,334,711; and Gold, et al., U.S. Pat. No. 6,300,074. All of the above references describe various chemical modifications that can be made to the base, phosphate and/or sugar moieties of the nucleic acid molecules described herein.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications. For a review, see Usman and Cedergren, *TIBS* 17:34, 1992; Usman, et al., *Nucleic Acids Symp. Ser.* 31:163, 1994; Burgin, et al., *Biochemistry* 35:14090, 1996. Sugar modification of nucleic acid molecules have been extensively described in the art. See Eckstein et al., International Publication No. WO/1992/07065; Perrault, et al. *Nature* 344: 565-568, 1990; Pieken, et al. *Science* 253:314-317, 1991; Usman and Cedergren, *Trends in Biochem. Sci.* 17:334-339, 1992; Usman et al. International Publication No. WO/1993/15187; Sproat, U.S. Pat. No. 5,334,711 and Beigelman, et al., *J. Biol. Chem.* 270:25702, 1995; Beigelman, et al., International Publication No. WO/1997/26270; Beigelman, et al., U.S. Pat. No. 5,716,824; Usman, et al., U.S. Pat. No. 5,627,053; Woolf, et al., International Publication No. WO/1998/13526; Thompson, et al., Karpeisky, et al., *Tetrahedron Lett.* 39:1131, 1998; Earnshaw and Gait, *Biopolymers (Nucleic Acid Sciences)* 48:39-55, 1998; Verma and Eckstein, *Annu. Rev. Biochem.* 67:99-134, 1998; and Burlina, et al., *Bioorg. Med. Chem.* 5:1999-2010, 1997. Such publications describe general methods and strategies to determine the location of incorporation of sugar, base and/or phosphate modifications and the like into nucleic acid molecules without modulating catalysis. In view of such teachings, similar modifications can be used as described herein to modify the siNA nucleic acid molecules of the instant invention so long as the ability of siNA to promote RNAi in cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

In one embodiment, the invention features modified siNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, *Nucleic Acid Analogues: Synthesis and Properties, in Modern Synthetic Methods, VCH,* 1995, pp. 331-417, and Mesmaeker, et al., "Novel Backbone Replacements for Oligonucleotides, in Carbohydrate Modifications in Antisense Research," *ACS,* 1994, pp. 24-39.

Methods for the delivery of nucleic acid molecules are described in Akhtar, et al., *Trends Cell Bio.* 2:139, 1992; "Delivery Strategies for Antisense Oligonucleotide Therapeutics," ed. Akhtar, 1995; Maurer, et al., *Mol. Membr. Biol.* 16:129-140, 1999; Hofland and Huang, *Handb. Exp. Pharmacol.* 137:165-192, 1999; and Lee, et al., *ACS Symp. Ser.* 752:184-192, 2000. Beigelman, et al., U.S. Pat. No. 6,395,713, and Sullivan et al., International Publication No. WO/1994/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation internally or externally by liposomes, by iontophoresis, or by incorporation into other vehicles, such as biodegradable polymers, hydrogels, cyclodextrins (see e.g. Gonzalez, et al., *Bioconjugate Chem.* 10:1068-1074, 1999; Wang, et al., International Publication Nos. WO/2003/47518 and WO/2003/46185), poly(lactic-co-glycolic)acid (PLGA) and PLCA microspheres (see e.g. U.S. Pat. No. 6,447,796 and U.S. Patent Application Publication No. US 2002/130430), biodegradable nanocapsules, and bioadhesive microspheres, or by proteinaceous vectors (O'Hare and Normand, International Publication No. WO/2000/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry, et al., *Clin. Cancer Res.* 5:2330-2337, 1999, and Barry, et al., International Publication No. WO/1999/31262. The molecules of the instant invention can be used as pharmaceutical agents. Pharmaceutical agents prevent, modulate the occurrence, or treat (alleviate a symptom to some extent, preferably all of the symptoms) of a disease state in a subject.

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example, at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "cap structure" is meant chemical modifications, which have been incorporated at either terminus of the oligonucleotide (see, e.g. Adamic, et al., U.S. Pat. No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(β-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Examples of the 3'-cap include, but are not limited to, glyceryl, inverted deoxy abasic residue (moiety), 4',5'-methylene nucleotide; 1-(β-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, *Tetrahedron* 49:1925, 1993; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g. Usman and McSwiggen, supra; Eckstein, et al., International Publication No. WO/1992/07065; Usman, et al, International Publication No. WO/1993/15187; Uhlman & Peyman, supra, all are hereby incorporated by reference herein). There are several examples of modified nucleic acid bases known in the art as summarized by Limbach, et al., *Nucleic Acids Res.* 22:2183, 1994. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., *Biochemistry* 35:14090, 1996; Uhlman & Peyman, supra). By "modified bases" in this aspect is meant nucleotide bases other than adenine, guanine, cytosine and uracil at l' position or their equivalents.

By "target site" or "target sequence" or "targeted sequence" is meant a sequence within a target nucleic acid (e.g., RNA) that is "targeted" for cleavage mediated by a siNA construct which contains sequences within its antisense region that are complementary to the target sequence.

The siNA molecules can be complexed with cationic lipids, packaged within liposomes, or otherwise delivered to target cells or tissues. The nucleic acid or nucleic acid complexes can be locally administered to through injection, infusion pump or stent, with or without their incorporation in biopolymers. In another embodiment, polyethylene glycol (PEG) can be covalently attached to siNA compounds of the present invention, to the polypeptide, or both. The attached PEG can be any molecular weight, preferably from about 2,000 to about 50,000 daltons (Da).

The sense region can be connected to the antisense region via a linker molecule, such as a polynucleotide linker or a non-nucleotide linker.

"Inverted repeat" refers to a nucleic acid sequence comprising a sense and an antisense element positioned so that they are able to form a double stranded siRNA when the repeat is transcribed. The inverted repeat may optionally include a linker or a heterologous sequence such as a self-cleaving ribozyme between the two elements of the repeat. The elements of the inverted repeat have a length sufficient to form a double stranded RNA. Typically, each element of the inverted repeat is about 15 to about 100 nucleotides in length, preferably about 20-30 base nucleotides, preferably about 20-25 nucleotides in length, e.g., 20, 21, 22, 23, 24, 25, 26, 27, 28, 29, or 30 nucleotides in length.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

"Large double-stranded RNA" refers to any double-stranded RNA having a size greater than about 40 bp for example, larger than 100 bp or more particularly larger than 300 bp. The sequence of a large dsRNA may represent a segment of a mRNA or the entire mRNA. The maximum size of the large dsRNA is not limited herein. The double-stranded RNA may include modified bases where the modification may be to the phosphate sugar backbone or to the nucleoside. Such modifications may include a nitrogen or sulfur heteroatom or any other modification known in the art.

The double-stranded structure may be formed by self-complementary RNA strand such as occurs for a hairpin or a micro RNA or by annealing of two distinct complementary RNA strands.

"Overlapping" refers to when two RNA fragments have sequences which overlap by a plurality of nucleotides on one strand, for example, where the plurality of nucleotides (nt) numbers as few as 2-5 nucleotides or by 5-10 nucleotides or more.

"One or more dsRNAs" refers to dsRNAs that differ from each other on the basis of primary sequence.

"Target gene or mRNA" refers to any gene or mRNA of interest. Indeed any of the genes previously identified by genetics or by sequencing may represent a target. Target genes or mRNA may include developmental genes and regulatory genes as well as metabolic or structural genes or genes encoding enzymes. The target gene may be expressed in those cells in which a phenotype is being investigated or in an organism in a manner that directly or indirectly impacts a phenotypic characteristic. The target gene may be endogenous or exogenous. Such cells include any cell in the body of an adult or embryonic animal or plant including gamete or any isolated cell such as occurs in an immortal cell line or primary cell culture.

All publications, references, patents, patent publications and patent applications cited herein are each hereby specifically incorporated by reference in entirety.

While this invention has been described in relation to certain embodiments, and many details have been set forth for purposes of illustration, it will be apparent to those skilled in the art that this invention includes additional embodiments, and that some of the details described herein may be varied considerably without departing from this invention. This invention includes such additional embodiments, modifications and equivalents. In particular, this invention includes any combination of the features, terms, or elements of the various illustrative components and examples.

The use herein of the terms "a," "an," "the" and similar terms in describing the invention, and in the claims, are to be construed to include both the singular and the plural. The terms "comprising," "having," "including" and "containing" are to be construed as open-ended terms which mean, for example, "including, but not limited to." Recitation of a range of values herein refers individually to each and any separate value falling within the range as if it were individually recited herein, whether or not some of the values within the range are expressly recited. For example, the range "4 to 12" includes without limitation the values 5, 5.1, 5.35 and any other whole, integer, fractional, or rational value greater than or equal to 4 and less than or equal to 12. Specific values employed herein will be understood as exemplary and not to limit the scope of the invention.

Definitions of technical terms provided herein should be construed to include without recitation those meanings associated with these terms known to those skilled in the art, and are not intended to limit the scope of the invention. Definitions of technical terms provided herein shall be construed to dominate over alternative definitions in the art or definitions which become incorporated herein by reference to the extent that the alternative definitions conflict with the definition provided herein.

The examples given herein, and the exemplary language used herein are solely for the purpose of illustration, and are not intended to limit the scope of the invention.

When a list of examples is given, such as a list of compounds or molecules suitable for this invention, it will be apparent to those skilled in the art that mixtures of the listed compounds or molecules are also suitable.

Example 1

In Vitro Assay for LacZ Gene Expression Knockdown in 9L Cells

9L/LacZ is a rat gliosarcoma cell line stably expressing the LacZ gene that encodes bacterial galactosidase. LacZ gene knockdown measurements can be used as a primary activity-based in vitro assay for interfering RNA delivery formulations.

For LacZ gene knockdown measurements, 9L/LacZ cells were transfected with an RNAi formulation, and a β-galactosidase assay was performed on cells harvested at day 3 post transfection. An additional assay was performed to quantify protein concentration.

9L/LacZ cells were plated at 8000 cells/well (96-well) and incubated overnight in medium. Confluency was about 15-20% at the time of transfection. Transfection complex was prepared by adding an interfering RNA to OptiMEM™ medium and vortexing, separately adding a delivery formulation to OptiMEM™ medium and vortexing, and finally mixing the interfering RNA in medium with the delivery formulation in medium to make the transfection complex. The medium for incubated cells was replaced with fresh no-serum media (OptiMEM™ without serum) and transfection complex was added to each well. Cells were incubated 5 hrs, then after the addition of 100 microliters complete medium (DMEM plus 10% fetal bovine serum) were incubated overnight at 37° C. and 5% $CO_2$. The next day, 24 hours after transfection, the medium was changed to fresh complete medium and the cells were incubated another 48 hrs at 37° C. and 5% $CO_2$.

For LacZ gene knockdown, the harvested 9L/LacZ cells were washed in PBS, lysed in M-PER™ Reagent (Pierce), and incubated at room temperature for 15 minutes. Lysate was taken from each well for protein assay with a Micro BCA kit (Pierce, Thermo Fisher Scientific) and β-gal assay with All-in-One™ β-Galactosidase Assay Reagent (Pierce).

In Vitro Assay for PPIB Gene Expression Knockdown in A549 Cells

Cyclophilin B (PPIB) gene knockdown measurements can be used as a primary activity-based in vitro assay for interfering RNA delivery formulations. Cyclophilin B (PPIB) gene expression knockdown was measured in A549 human alveolar basal epithelial cells. For PPIB gene knockdown measurements, A549 cells were transfected with an interfering RNA formulation, total RNA prepared 24 hours after transfection, and PPIB mRNA assayed by RT-PCR. QRT-PCR of 36B4 (acidic ribosomal phosphoprotein PO) mRNA expression was performed for normalization.

A549 cells were seeded at 7,500 cells/well (96-well) and incubated overnight in medium. Confluency was about 50% at the time of transfection. Transfection complex was prepared by adding an interfering RNA to medium (OptiMEM™) and vortexing, separately adding a delivery formulation to medium (OptiMEM™) and vortexing, and finally mixing the interfering RNA in medium with the delivery formulation in medium and incubating 20 minutes at room temperature to make the transfection complex. The medium for incubated cells was replaced with fresh OptiMEM™ and transfection complex was added to each well. Cells were incubated for 5 hrs at 37° C. and 5% $CO_2$, then complete medium was added (to a final fetal bovine serum concentration 10%) and incubation continued until 24 hours post-transfection.

For PPIB gene knockdown cells were lysed and RNA prepared (Invisorb RNA Cell HTS 96-Kit/C, Invitek, Berlin, or RNeasy 96 Kit, Qiagen). Quantitative RT-PCR was performed using One-Step qRT-PCR kit (Invitrogen) on a DNA Engine Opticon2 thermal cycler (BioRad).

```
Primers used for PPIB were:
                            (SEQ ID NO: 323)
5'-GGCTCCCAGTTCTTCATCAC-3' (forward)
and (SEQ ID NO: 324)
5'-CCTTCCGCACCACCTC-3' (reverse) with (SEQ ID NO: 325)
5'-FAM-CTAGATGGCAAGCATGTGGTGTTTGG-TAMRA-3'
for the probe.

For 36B4, primers were:
                            (SEQ ID NO: 326)
5'-TCTATCATCAACGGGTACAAACGA-3' (forward)
and (SEQ ID NO: 327)
5'-CTTTTCAGCAAGTGGGAAGGTG-3' (reverse) with (SEQ ID NO: 328)
5'-FAM-CCTGGCCTTGTCTGTGGAGACGGATTA-TAMRA-3'
for the probe.
```

In Vivo Assay for Influenza Viral Titer Knockdown in Mouse

Influenza viral titer knockdown measurements in mice can be used as an in vivo gauge of efficacy for interfering RNA lipopeptide delivery formulations.

In this assay, typically 50 uL of a interfering RNA lipopeptide formulation, or PBS for a control group, was administered intranasally in 7-9 week old Balb/C mice anesthetized with ketamine/xylazine. Daily dosing was performed for 3 consecutive days on days −2, −1, and 0. Infection was induced 4 hours after the last dosing.

Influenza infection was induced with Influenza A/Puerto Rico/8/34 (PR8, subtype H1N1). For infection, 50 µl of 20 pfu PR8 diluted in 0.3% BSA/1×PBS/PS was administered intranasally into mice anesthetized with ketamine/xylazine. 48 hours after infection, the lungs were harvested and homogenized in 600 uL 0.3% BSA/1×PBS/PS. The homogenates were frozen and thawed twice to release the virus. A TCID50 assay (Tissue-Culture Infectious Dose 50) was performed to titer virus in lung homogenates. Flat-bottom, 96-well plates were seeded with $2\times10^4$ MDCK cells per well, and 24 hours later, the serum-containing medium was removed. 30 uL of lung homogenates, either undiluted or diluted from 10- to $10^7$-fold (in 10-fold steps), was added into quadruplicate wells. After incubation for 1 hr, 170 µl of infection medium (DMEM/0.3% BSA/10 mM HEPES/PS) containing 4 µg/ml trypsin was added to each well. After incubation for 48 hours at 37° C., the presence or absence of virus in the culture supernatants was determined by hemagglutination of chicken red blood cells. The virus titers were estimated using the Spearman and Karber formula.

SYBR™ Gold Assay for siRNA Concentrations

The concentration of dsRNA in a formulation can be determined by SYBR™ Gold assay as follows: 10 ul of dsRNA formulation is added to 100 ul MeOH and incubated for 5 minutes at 55° C. 50 ul Heparin (200 mg/ml) is added, and the solution is incubated for 5 minutes at 55° C. 790 ul PBS (phosphate buffered saline) is added, and the sample is spun down in microfuge to pelletize. A 90 ul sample of the pellet is incubated with 10 ul SYBR™ Gold reagent (Molecular Probes, Eugene, Oreg.). Fluorescence is read at Em 535 nm with excitation at 495 nm.

Example 2

The structure of some double-stranded RNAs of this disclosure are shown in Table 6.

TABLE 6

| Double-stranded RNAs | |
|---|---|
| DX3030 Influenza | (SEQ ID NO: 329) Sense 5'-GGAUCUUAUUUCUUCGGAGACAAdTdG-3' (SEQ ID NO: 330) Antisense 5'-CAUUGUCUCCGAAGAAAUAAGAUCCUU-3' |
| DX2816 Non target Qneg | (SEQ ID NO: 331) Sense 5'-UUCUCCGAACGUGUCACGUdTdT-3' (SEQ ID NO: 332) Antisense 5'-ACGUGACACGUUCGGAGAAdTdT-3' |
| DX2940 LacZ | (SEQ ID NO: 333) Sense 5'-CUACACAAAUCAGCGAUUUdTdT-3' (SEQ ID NO: 334) Antisense 5'-AAAUCGCUGAUUUGUGUAGdTdC-3' |

TABLE 6-continued

Double-stranded RNAs

| | | |
|---|---|---|
| DX2742 PPIB MoCypB | (SEQ ID NO: 335) Sense 5'-GGAAAGACUGUUCCAAAAAUU-3' (SEQ ID NO: 336) Antisense 5'-UUUUUGGAACAGUCUUUCCUU-3' | |
| DX2744 G1498 influenza | (SEQ ID NO: 337) Sense 5'-GGAUCUUAUUUCUUCGGAGdTdT-3' (SEQ ID NO: 338) Antisense 5'-CUCCGAAGAAAUAAGAUCCdTdT-3' | |
| DX2918 Inm4 TNFa modified | (SEQ ID NO: 339) Sense 5'-CCGTCAGCCGATTTGCTATTT-3' (SEQ ID NO: 340) Antisense 5'-p-AUAGCAAATCGGCTGACGGTT-3' | |

Example 3

Active RNA formulations of this disclosure can be prepared by dissolving an interfering RNA in buffer or cell culture medium and vortexing, separately admixing a delivery formulation with buffer or cell culture medium and vortexing, and finally admixing the interfering RNA mixture with the delivery formulation mixture to make an active RNAi transfection formulation.

To prepare a delivery formulation, lipopeptides along with other lipids and/or excipients can be solubilized in $CHCl_3$/MeOH, dried down under $N_2$, and hydrated in 10 mM HEPES with 5% dextrose at pH 7.4. The mixture can be sonicated, or extruded, dialyzed, and/or tangential flow filtered.

An exemplary interfering RNA formulation of this disclosure is shown in Table 7. In this example, the lipopeptide provides its own formulation for intracellular delivery of an interfering siRNA therapeutic. The amount of lipopeptide is given as the mole percentage of delivery components, not including the active RNA agent.

TABLE 7 siRNA Formulation

| Component | Amount |
|---|---|
| siRNA | 50 nM |
| lipopeptide | 100 mole % |

An exemplary interfering RNA formulation of this disclosure is shown in Table 8. In this example, the lipopeptide provides its own formulation for intracellular delivery of an interfering siRNA therapeutic. The amount of lipopeptide is given as the mole percentage of delivery components, not including the active RNA agent. The length of the lipophilic group for each peptide on the proceeding tables is represented by "(CX)" where "X" represents the number of carbons in the lipophilic group. For example, C20 represents a lipophilic group with a 20 carbon chain length.

TABLE 8 dsRNA Formulation

| Component | Amount |
|---|---|
| dsRNA | 50 nM |
| (C16)—(H)$_8$(R)$_8$(H)$_8$K—NH—(C16) (SEQ ID NO: 13) | 100 mole % |

An exemplary RNAi formulation of this disclosure is shown in Table 9. In this example, the lipopeptide is combined with a non-cationic lipid in a co-delivery formulation.

TABLE 9

DX3030 Formulation

| Component | Amount |
|---|---|
| siRNA DX3030 | 50 nM |
| (C20)—(H)$_8$(R)$_8$(H)$_8$K—NH—(C20) (SEQ ID NO: 13) | 50 mole % |
| 1,2-Distearoyl-sn-glycero-3-phosphoethanolamine (DSPE) | 50 mole % |

An exemplary RNAi formulation of this disclosure is shown in Table 10. In this example, a lipopeptide is combined with a cationic lipid, a non-cationic lipid, and a pegylated lipid in a multicomponent delivery formulation.

TABLE 10 dsRNA Formulation

| Component | Amount |
|---|---|
| dsRNA | 25 nM |
| (C20)—(H)$_8$(R)$_8$(H)$_8$K—NH—(C20) (SEQ ID NO: 13) | 50 mole % |
| DSPC | 49 mole % |
| DSPE-PEG2000 | 1 mole % |

Examples of additional lipids for RNAi formulations of this disclosure are shown in Table 11.

TABLE 11

Lipids for Delivery Formulations

| Material | MW |
|---|---|
| DOTAP Avanti 890890C | 698.55 |
| DOPE Avanti 850725C | 744.04 |
| DPhyPE Avanti 850402P | 804.18 |

Example 4

The knockdown activities of example formulations of interfering RNA compositions of this disclosure are shown in Table 12.

TABLE 12

Knockdown for Delivery Formulations

| N:P Ratio | SEQ ID NO: | Lipopeptide | % KD (vs QNeg) A549/PPIB | % KD (vs QNeg) L/91acZ |
|---|---|---|---|---|
| 2 | — | RNAiMAX ™ | 73.4 | 82.4 |
| 2 | 350 | (C18)-HHHHRRRRRRRR-Cysteamide | 15.3 | -0.8 |
| 2 | 351 | (C18)-PEG27-HHHHHHHHRRRRRRRR-amide | 30.6 | 9.2 |
| 2 | 352 | Ac-GALFLAFLAAALSLMGLWSQPKKKRKV-Cysteamide | 20.5 | 29.1 |
| 2 | 353 | Ac-GALFLAFLAAALSLMGLWSQPKSKRKV-Cysteamide | 15.5 | 29.5 |
| 2 | 296 | Ac-LIRLWSHLIHIWFQNRRLKWKKK-amide | 8.7 | -19.9 |
| 2 | 13 | (C20)-(H)$_8$(R)$_8$(H)$_8$K-NH-(C20) | 29.7 | 60.1 |
| 2 | 354 | (C16)-HHHHHKHHHKKKHKHKKK-Cysteamide | 14.7 | 12.0 |
| 2 | 355 | (C18)-HHHHHKHHHKKKHKHKKK-cysteamide | 25.5 | -11.3 |
| 2 | 356 | Ac-GALFLGFLGAAGSTMGAWSQPKSKRKV-amide | -8.1 | -0.4 |
| 4 | 10 | (C18)-PEG27-HHHHHHHHRRRRRRRR-amide | 7.4 | -16.1 |
| 4 | 353 | Ac-GALFLAFLAAALSLMGLWSQPKSKRKV-Cysteamide | 16.0 | -9.3 |
| 4 | 296 | Ac-LIRLWSHLIHIWFQNRRLKWKKK-amide | -28.8 | -4.5 |
| 4 | 13 | (C20)-(H)$_8$(R)$_8$(H)$_8$K-NH-(C20) | 65.8 | 57.5 |
| 4 | 354 | (C16)-HHHHHKHHHKKKHKHKKK-Cysteamide | -19.8 | 12.4 |
| 4 | 355 | (C18)-HHHHHKHHHKKKHKHKKK-cysteamide | 21.6 | -19.4 |
| 4 | 356 | Ac-GALFLGFLGAAGSTMGAWSQPKSKRKV-amide | -3.7 | -1.6 |

For the lipopeptides in Table 12, the results showed that at least two lipopeptides, (C20)-(H)$_8$(R)$_8$(H)$_8$K—NH—(C20) (SEQ ID NO: 13) and (C18)-HHHHHKHHHKKKH-KHKKK-cysteamide (SEQ ID NO: 355), exhibited significant knockdown in at least the A549/PPIB assay as compared to both Qneg and vehicle (data for vehicle not shown).

---

What is claimed is:

1. A compound having the structure shown in Formula I:

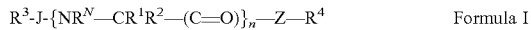

$$R^3\text{-J-}\{NR^N\text{—}CR^1R^2\text{—}(C\!=\!O)\}_n\text{—}Z\text{—}R^4 \qquad \text{Formula I}$$

wherein
{NR$^N$—CR$^1$R$^2$—(C=O)}$_n$ is central peptide HHHH-HKHHHKKKHKHKKK SEQ ID NO:15);
R$^3$ and R$^4$ are independently of one another, a lipophilic tail derived from a naturally-occurring or synthetic lipid, phospholipid, glycolipid, triacylglycerol, glycerophospholipid, sphingolipid, ceramide, sphingomyelin, cerebroside, or ganglioside, wherein the tail may contain a steroid, or an organic group consisting of carbon, oxygen, nitrogen, sulfur, and hydrogen atoms, and having from 1 to 20 carbon atoms, or a substituted or unsubstituted C(1-22)alkyl, C(6-12)cycloalkyl, C(6-12)cycloalkyl-alkyl, C(3-18)alkenyl, C(3-18)alkynyl, or C(1-5)alkoxy-C(1-5)alkyl, or a sphinganine, (2R,3R)-2-amino-1,3-octadecanediol, icosasphinganine, sphingosine, phytosphingosine, cis-4-sphingenine, or a ceramide;
Z is NH, O, or a linker comprising a maleimido, thioether, amide, cysteamide, cysteine, thiol, or a disulfide group, or a polyethyleneoxide or polypropyleneoxide group comprising 1-400 atoms, or a linker comprising 1-200 atoms selected from the group of C, H, F, Cl, Br, N, O, S, Si, and P;
J is (C=O), O, or a linker comprising a maleimido, thioether, amide, cysteamide, cysteine, thiol, or disulfide group, or a polyethyleneoxide or polypropyleneoxide group comprising 1-400 atoms, or a linker comprising 1-200 atoms selected from the group of C, H, F, Cl, Br, N, O, S, Si, and P
and pharmaceutically acceptable salts thereof.

2. The compound of claim 1, wherein a functional group is linked to a side chain of the central peptide HHHHHKH-HHKKKHKHKKK (SEQ ID NO:15), wherein the functional group is selected from the side chain of 3,5-diiodo-tyrosine, 1-methylhistidine, and 2-methylbutanoic acid, or is selected from 2-o-anisylpropanoic acid, meso-tartaric acid, 4,6-dimethylpyrimidinamine, p-phthalic acid, creatinine, butanoic acid, N,N-dimethyl-1-naphthylamine, pentanoic acid, 4-methylpentanoic acid, N-methylaniline, 1,10-phenanthroline, 3-pyridinecarboxylic acid, hexanoic acid, propanoic acid, 4-animobenzoic acid, 2-methylpropanoic acid, heptanoic acid, octanoic acid, cyclohexanecarboxylic acid, quinoline, 3-quinolinamine, 2-aminobenzoic acid, 4-pyridinecarboxylic acid, nonanoic acid, melamine, 8-quinolinol, trimethylacetic acid, 6-methoxyquinoline, 4-(methylamino)benzoic acid, p-methylaniline, 3-(methylamino)benzoic acid, malic acid, N-ethylaniline, 2-benzylpyridine, 3,6-dinitrophenol, N,N-dimethylaniline, 2,5-dimethylpiperazine, p-phenetidine, 5-methylquinoline, 2-phenylbenzimidazole, pyridine, picolinic acid, p-anisidine, 2-(methylamino)benzoic acid, 2-thiazolamine, glutaric acid, adipic acid, isoquinoline, itaconic acid, o-phthalic acid, benzimidazole, piperazine, heptanedioic acid, acridine, phenanthridine, succinic acid, methylsuccinic acid, 4-methylquinoline, 3-methylpyridine, 7-isoquinolinol, malonic acid, methylmalonic acid, 2-methylquinoline, 2-ethylpyridine, 2-methylpyridine, 4-methylpyridine, histamine, histidine, maleic acid, cis-1,2-cyclohexanediamine, 3,5-dimethylpyridine, 2-ethylbenzimidazole, 2-methylbenzimidazole, cacodylic acid, perimidine, citric acid, isocitric acid, 2,5-dimethylpyridine, papaverine, 6-hydroxy-4-methylpteridine, L-thyroxine, 3,4-dimethylpyridine, methoxypyridine, trans-1,2-cyclohexanediamine, 2,5-pyridinediamine, 1-1-methylhistidine, 1-3-methylhistidine, 2,3-dimethylpyridine, xanthopterin, 1,2-propanediamine, N,N-diethylaniline, alloxanic acid, 2,6-dimethylpyridine, L-carnosine, 2-pyridinamine, N-b-alanylhistidine, pilocarpine, 1-methylimidazol, 1H-imidazole, 2,4-dimethylpyridine, 4-nitrophenol, 2-nitrophenol, tyrosineamide, 5-hydoxyquinazoline, 1,1-cyclopropanedicarboxylic acid, 2,4,6-trimethylpyridine, 2,3-dichlorophenol, 1,2-ethanediamine, 1-isoquinolinamine, and combinations thereof.

3. A pharmaceutical composition comprising a nucleic acid agent and one or more compounds according to claim 1.

4. The composition of claim 3, wherein the nucleic acid agent is an mdRNA.

5. The composition of claim 3, wherein the nucleic acid agent is an siRNA.

6. The composition of claim 3, further comprising a non-cationic lipid.

7. The composition of claim 3, further comprising a polymeric lipid.

8. A method for delivering an interfering RNA agent to a cell comprising preparing a composition according to claim 3 and treating a cell with the composition.

9. A method for inhibiting expression of a gene in a cell comprising preparing a composition according to claim 3 and treating a cell with the composition.

10. A method for inhibiting expression of a gene in a mammal comprising preparing a composition according to claim 3 and administering the composition to the mammal.

11. A method for treating the signs and symptoms of a disease, disorder, or condition in a subject selected from cancer, a proliferative disease, disorder, or condition, a metabolic disease, disorder, or condition, an inflammatory disease, disorder, or condition, and a viral infection by providing a composition of claim 5 and administering the composition to the subject.

* * * * *